(12) United States Patent
Nagamine et al.

(10) Patent No.: US 10,437,147 B2
(45) Date of Patent: Oct. 8, 2019

(54) RESIST COMPOSITION AND METHOD FOR FORMING RESIST PATTERN

(71) Applicant: TOKYO OHKA KOGYO CO., LTD., Kawasaki-shi (JP)

(72) Inventors: Takashi Nagamine, Kawasaki (JP); Yuta Iwasawa, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 15/471,428

(22) Filed: Mar. 28, 2017

(65) Prior Publication Data

US 2017/0285469 A1 Oct. 5, 2017

(30) Foreign Application Priority Data

Mar. 31, 2016 (JP) ................... 2016-073723

(51) Int. Cl.
| | | |
|---|---|---|
| *G03F 7/004* | (2006.01) | |
| *G03F 7/26* | (2006.01) | |
| *H01L 21/027* | (2006.01) | |
| *C07C 381/12* | (2006.01) | |
| *C08F 224/00* | (2006.01) | |
| *G03F 7/038* | (2006.01) | |
| *G03F 7/039* | (2006.01) | |
| *G03F 7/09* | (2006.01) | |
| *G03F 7/16* | (2006.01) | |
| *G03F 7/20* | (2006.01) | |
| *G03F 7/32* | (2006.01) | |
| *G03F 7/38* | (2006.01) | |

(52) U.S. Cl.
CPC .......... *G03F 7/0045* (2013.01); *C07C 381/12* (2013.01); *C08F 224/00* (2013.01); *G03F 7/0382* (2013.01); *G03F 7/0397* (2013.01); *G03F 7/091* (2013.01); *G03F 7/16* (2013.01); *G03F 7/168* (2013.01); *G03F 7/2006* (2013.01); *G03F 7/2041* (2013.01); *G03F 7/26* (2013.01); *G03F 7/322* (2013.01); *G03F 7/38* (2013.01); *H01L 21/0274* (2013.01)

(58) Field of Classification Search
CPC . G03F 7/004; G03F 7/26; G03F 7/039; G03F 7/038; H01L 21/0274; C08F 224/00; C07C 381/12
USPC ................................ 430/270.1, 913
See application file for complete search history.

(56) References Cited

U.S. PATENT DOCUMENTS

| 6,949,325 | B2 | 9/2005 | Li et al. | |
|---|---|---|---|---|
| 8,802,349 | B2* | 8/2014 | Yoshidome | ........... G03F 7/0046 430/270.1 |
| 9,341,947 | B2* | 5/2016 | Komuro | ................... G03F 7/30 |
| 9,851,637 | B2* | 12/2017 | Nagamine | ............. G03F 7/0045 |
| 2001/0049073 | A1 | 12/2001 | Hada et al. | |
| 2004/0110085 | A1 | 6/2004 | Iwai et al. | |
| 2009/0197204 | A1 | 8/2009 | Shiono et al. | |
| 2009/0317743 | A1 | 12/2009 | Shiono et al. | |
| 2010/0297555 | A1* | 11/2010 | Koyama | .............. C07D 307/00 430/270.1 |
| 2010/0310985 | A1 | 12/2010 | Mori et al. | |
| 2011/0117499 | A1 | 5/2011 | Matsumiya et al. | |
| 2011/0311914 | A1* | 12/2011 | Kamimura | .............. C08F 20/28 430/270.1 |
| 2012/0009522 | A1* | 1/2012 | Kato | ..................... G03F 7/0046 430/283.1 |
| 2012/0129100 | A1* | 5/2012 | Shibuya | .................. C08F 20/10 430/281.1 |
| 2012/0149916 | A1 | 6/2012 | Utsumi et al. | |
| 2012/0321855 | A1* | 12/2012 | Iwato | .................... G03F 7/0045 428/156 |
| 2013/0011785 | A1* | 1/2013 | Kato | ..................... G03F 7/0397 430/270.1 |
| 2013/0049149 | A1* | 2/2013 | Kato | ..................... G03F 7/0045 257/431 |
| 2013/0084527 | A1* | 4/2013 | Hatakeyama | ......... C08F 220/68 430/283.1 |
| 2013/0101812 | A1* | 4/2013 | Kamimura | ................ G03F 7/32 428/195.1 |
| 2013/0115554 | A1* | 5/2013 | Takaki | .................. C07C 233/92 430/283.1 |
| 2013/0130178 | A1 | 5/2013 | Iizuka et al. | |
| 2013/0164676 | A1 | 6/2013 | Fukumoto et al. | |
| 2015/0140497 | A1* | 5/2015 | Arai | ....................... C08F 220/28 430/325 |
| 2016/0060374 | A1 | 3/2016 | Koyama et al. | |

FOREIGN PATENT DOCUMENTS

| JP | 2000-206694 A | 7/2000 |
|---|---|---|
| JP | 2003-241385 A | 8/2003 |
| JP | 2005-336452 A | 12/2005 |
| JP | 2006-259582 A | 9/2006 |
| JP | 2006-317803 A | 11/2006 |

(Continued)

OTHER PUBLICATIONS

Office Action issued in JP application No. 2014-172077, dated Jan. 30, 2018.
Notice of Allowance in U.S. Appl. No. 14/835,531, dated Feb. 11, 2016.

*Primary Examiner* — Amanda C. Walke
(74) *Attorney, Agent, or Firm* — Knobbe, Martens, Olson & Bear LLP

(57) ABSTRACT

A resist composition which includes a polymer compound including a structural unit which is derived from an acrylic ester in which the hydrogen atom bonded to an α-position carbon atom may be substituted with a substituent and which has a lactone-containing cyclic group containing other electron withdrawing groups such as a cyano group at a side chain terminal, and a compound whose a conjugate acid has an acid dissociation constant (pKa) of less than 3.

18 Claims, No Drawings

(56) References Cited

FOREIGN PATENT DOCUMENTS

| | | |
|---|---|---|
| JP | 2008-231059 A | 10/2008 |
| JP | A-2009-025723 | 2/2009 |
| JP | 2010-002870 A | 1/2010 |
| JP | 2010-032994 A | 2/2010 |
| JP | 2010-277043 A | 12/2010 |
| JP | 2011-013569 A | 1/2011 |
| JP | 2011-128226 A | 6/2011 |
| JP | 2012-062371 A | 3/2012 |
| JP | 2012-108480 A | 6/2012 |
| JP | A-2014-115386 | 6/2014 |
| JP | 2015-117288 A | 6/2015 |
| JP | 2016-044157 A | 4/2016 |
| JP | 2016-044158 A | 4/2016 |
| WO | WO 2009/107327 A1 | 9/2009 |

\* cited by examiner

RESIST COMPOSITION AND METHOD FOR FORMING RESIST PATTERN

RELATED APPLICATIONS

This application claims priority to Japanese Patent Application No. 2016-073723, filed Mar. 31, 2016, the entire content of which is hereby incorporated by reference.

BACKGROUND OF THE INVENTION

Field of the Invention

The present invention relates to a resist composition and a method for forming a resist pattern.

Background Art

A lithography technique includes steps of forming a resist film composed of a resist material on a substrate, selectively exposing the resist film with light, and subjecting a developing treatment, thereby forming a resist pattern having a predetermined shape on the resist film. A resist material in which an exposed area of the resist film is dissolved in a developing solution is referred to a positive-type resist material, and a resist material in which an exposed area of the resist film is not dissolved in a developing solution is referred to a negative-type resist material.

In recent years, in the manufacturing of semiconductor devices and liquid crystal display elements, pattern miniaturization has been rapidly progressed in accordance with the progress of the lithography technique. As a miniaturization technique, generally, shortening the wavelength (realizing high energy) of an exposure light source has been performed. Specifically, ultraviolet rays represented by a g-line and an i-line was used in the related art, but KrF excimer laser or ArF excimer laser has been used for the mass production of semiconductor devices these days. In addition, studies regarding extreme ultraviolet rays (EUV) having a shorter wavelength (high energy) than that of the excimer laser, electron beams (EB), and an X-ray have been conducted.

The resist material is required to have lithography properties such as sensitivity with respect to the exposure light sources and resolution capable of reproducing patterns of minute dimensions.

In the related art, as a resist material satisfying such a requirement, a chemically amplified resist composition containing a base material component whose solubility in a developing solution changes under the action of an acid, and an acid generator component which generates an acid upon exposure has been used.

For example, in a case where the developing solution is an alkali developing solution (alkali developing process), a chemically amplified positive-type resist composition which contains a resin component (a base resin) whose solubility in the alkali developing solution increases under the action of an acid and an acid generator component is typically used. When a resist film formed by applying the aforementioned resist composition is selectively exposed to the light at the time of forming a resist pattern, an acid is generated from the acid generator component in the exposed area, the polarity of the base resin is increased under the action of the acid, so that the exposed area of the resist film becomes soluble in the alkali developing solution. For this reason, a positive-type pattern in which an unexposed area of the resist film remains as a pattern is formed by alkali developing.

On the other hand, in a case where such a chemically amplified resist composition is applied to a solvent developing process in which a developing solution (an organic developing solution) containing an organic solvent is used, the solubility in the organic developing solution is relatively decreased when the polarity of the base resin is increased, and thus the unexposed area of the resist film is dissolved and removed by the organic developing solution to thereby form a negative-type resist pattern in which the exposed area of the resist film remains as a pattern. The solvent developing process in which such a negative-type resist pattern is formed is referred to as a negative-type developing process in some cases (for example, refer to Japanese Unexamined Patent Application, Publication No. 2009-025723).

The base resin to be used for the chemically amplified resist composition generally has plural structural units for improving the lithography properties.

For example, in a case of the resin component in which the solubility in the alkali developing solution increases under the action of an acid, a structural unit including an acid-decomposable group, which is decomposed by the action of an acid generated from the acid generator or the like to increase the polarity, is used, and a structural unit including a lactone-containing cyclic group and a structural unit including a polar group such as a hydroxyl group are also used in combination therewith.

In addition, in the forming of the resist pattern, behavior of the acid generated from the acid generator component upon exposure is regarded as one element that greatly affects lithography properties.

In view of the above, a chemically amplified resist composition in which the base resin and an acid diffusion control agent which controls the diffusion of the acid generated upon exposure are used in combination is proposed.

For example, Japanese Unexamined Patent Application, Publication No. 2014-115386 discloses a resist composition containing a resin component whose solubility in a developing solution changes under the action of an acid, an acid generator component, and a photo-reactive quencher including a cation part having a specific structure as an acid diffusion control agent. The photo-reactive quencher is regarded as a component for exhibiting a quenching effect obtained by causing ion exchange reaction with the acid generated from the acid generator component, and the incorporation of the photo-reactive quencher prevents the acid generated from the acid generator component from being diffused from the exposed area of the resist film to the unexposed area thereof, thereby improving the lithography properties.

SUMMARY OF THE INVENTION

Meanwhile, as the lithography technique further progresses and the miniaturization of the resist pattern progresses more and more, in a case of forming the resist patterns of several tens to several hundreds of nanometers, the occurrence of scum and micro bridge after development becomes a serious problem. Thus, it is further required to suppress the occurrence of defects (surface defects) in the developed resist pattern.

Here, "defect" means, for example, general problems that are detected when the developed resist pattern is viewed from directly above by using a surface defect observing apparatus (product name of "KLA") manufactured by KLA-Tencor Corporation. Examples of the defects include a defect relating to foreign matters and precipitates attached on the resist pattern surface such as scum after development (resist residue), bubbles, and dust; a defect relating to a pattern shape such as bridge between line patterns and filling of a hole in a contact hole pattern; and a defect of a color unevenness of the pattern.

Typically, the resist composition is used after being stored for a certain period of time. In addition, in the conventional resist composition in which the base resin and the acid diffusion control agent are used in combination, there is a problem of exposure stability in that defects are likely to occur in the developed resist pattern at the time of forming the resist pattern.

The present invention has been made in consideration of the above described circumstance, and an object thereof is to provide a resist composition with improved lithography properties and excellent exposure stability.

According to a first aspect of the present invention, there is provided a resist composition which generates an acid upon exposure and whose solubility in a developing solution changes under the action of the acid, the resist composition including:

a base material component (A) whose solubility in the developing solution changes under the action of the acid and which contains a polymer compound (A1) having a structural unit (a0) represented by the following general formula (a0-1); and an acid diffusion control agent component (D) which contains a compound (D1) whose a conjugate acid has an acid dissociation constant (pKa) of less than 3.

[Chemical formula 1]

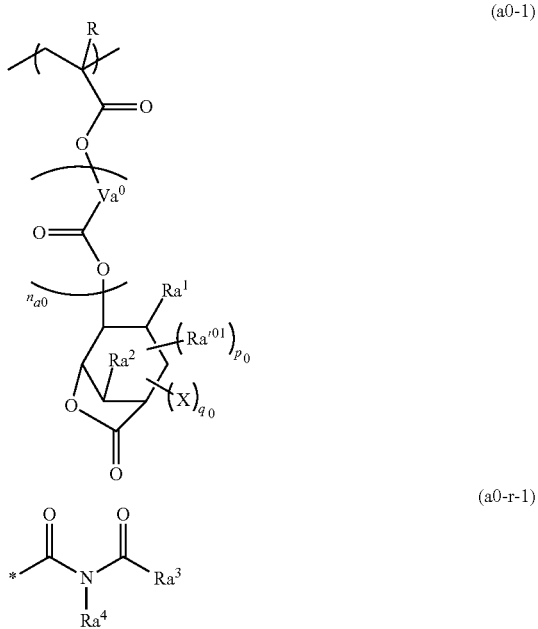

In the formula (a0-1), R is a hydrogen atom, an alkyl group having 1 to 5 carbon atoms or a halogenated alkyl group having 1 to 5 carbon atoms.

$Va^0$ is a divalent hydrocarbon group which may have a substituent.

$n_{a0}$ is an integer of 0 to 2.

$Ra^1$ and $Ra^2$ each independently represent a hydrogen atom, an alkyl group having 1 to 5 carbon atoms, an alkoxy group, or an alkylthio group, or $Ra^1$ and $Ra^2$ may be bonded to each other so as to form an alkylene group having 1 to 6 carbon atoms, which may contain an oxygen atom or a sulfur atom, an ether bond, or a thioether bond.

$Ra'^{01}$ is a halogen atom, an alkyl group having 1 to 6 carbon atoms which may have a halogen atom, a hydroxyalkyl group having 1 to 6 carbon atoms, of which the hydroxy group may be protected by a protective group and which may have a halogen atom, a carboxy group which may forma salt, or a substituted oxycarbonyl group.

$p_0$ is an integer of 0 to 8. In a case where two or more $Ra'^{01}$'s are present, the plural $Ra'^{01}$'s may be the same as or different from each other.

X is a group represented by general formula (a0-r-1), a cyano group, a halogen atom, a halogenated alkyl group, —C(=O)O$Ra^5$, —OC(=O)$Ra^5$, —CON($Ra^6$)($Ra^7$), —SO$_2$N($Ra^8$)($Ra^9$), or —SO$_2Ra^0$. The $Ra^5$ to $Ra^9$ each independently represent a hydrogen atom or an alkyl group. The $Ra^0$ is an alkyl group. In the formula (a0-r-1), $Ra^3$ and $Ra^4$ each independently represent a hydrogen atom or a nonaromatic hydrocarbon group which may have a substituent, or $Ra^3$ and $Ra^4$ may be bonded to each other so as to form a ring with the carbon atom to which $Ra^3$ is bonded and the nitrogen atom to which $Ra^4$ is bonded. Note that, a symbol of * in the formula (a0-r-1) represents a bond.

$q_0$ is an integer of 1 to 9. In a case where two or more X's are present, the plural X's may be the same as or different from each other.

According to a second aspect of the present invention, there is provided a method for forming a resist pattern, including a step of applying the resist composition according to the first aspect on a support to form a resist film; a step of exposing the resist film; and a step of developing the exposed resist film to form a resist pattern.

According to the present invention, it is possible to provide a resist composition with improved lithography properties and excellent exposure stability, and a method for forming a resist pattern using the resist composition.

DETAILED DESCRIPTION OF THE INVENTION

In the specification and claims of the present application, "aliphatic" is a relative concept with respect to aromatics, and is defined as a group, a compound, or the like having no aromaticity.

"Alkyl group" includes a linear, branched, or cyclic monovalent saturated hydrocarbon group unless otherwise noted. The same is true for an alkyl group in an alkoxy group.

"Alkylene group" includes contain a linear, branched, and cyclic divalent saturated hydrocarbon group unless otherwise noted.

"Halogenated alkyl group" is a group obtained by substituting at least one or all of hydrogen atoms of an alkyl group with halogen atoms, and examples of the halogen atom include a fluorine atom, a chlorine atom, a bromine atom, and an iodine atom.

"Fluorinated alkyl group" or "fluorinated alkylene group" means a group obtained by substituting at least one or all of the hydrogen atoms of an alkyl group or an alkylene group with a fluorine atom.

"Structural unit" means a monomer unit constituting a polymer compound (a resin, a polymer, or a copolymer).

The phrase "may have a substituent" means both a case of substituting a hydrogen atom (—H) with a monovalent group and a case of substituting a methylene group (—CH$_2$—) with a divalent group.

"Exposure" is a concept including radiation irradiation in general.

"Structural unit derived from acrylic ester" means a structural unit formed by cleavage of an ethylenic double bond of the acrylic ester.

"Acrylic ester" is a compound obtained by substituting a hydrogen atom at a carboxy group terminal of an acrylic acid ($CH_2$=CH—COOH) with an organic group.

The acrylic ester may be obtained by substituting a hydrogen atom bonded to an α-position carbon atom with a substituent. The substituent ($R^{\alpha 0}$) with which the hydrogen atom bonded to the α-position carbon atom is substituted is an atom other than the hydrogen atom or a group, and examples thereof include an alkyl group having 1 to 5 carbon atoms and a halogenated alkyl group having 1 to 5 carbon atoms. In addition, the acrylic ester includes itaconic acid diester obtained by substituting the substituent ($R^{\alpha 0}$) with a substituent containing an ester bond, and a hydroxyacrylic ester obtained by substituting the substituent ($R^{\alpha 0}$) with a group modified with a hydroxyalkyl group or a hydroxyl group thereof. Note that, the α-position carbon atom of the acrylic ester is a carbon atom to which a carbonyl group of an acrylic acid is bonded unless otherwise noted.

Hereinafter, acrylic ester obtained by substituting the hydrogen atom bonded to an α-position carbon atom with a substituent may be referred to as α-substituted acrylic ester. In addition, both of the acrylic ester and the α-substituted acrylic ester may be referred to as "(α-substituted) acrylic ester".

"Structural unit derived from acrylamide" means a structural unit formed by cleavage of an ethylenic double bond of the acrylamide.

The acrylamide may be obtained by substituting a hydrogen atom bonded to an α-position carbon atom with a substituent or may be obtained by substituting one or both of hydrogen atoms of an amino group of acrylamide with a substituent. Note that, the α-position carbon atom of the acrylamide is a carbon atom to which a carbonyl group of acrylamide is bonded unless otherwise noted.

As the substituent with which a hydrogen atom bonded to the α-position carbon atom of the acrylamide is substituted, the same substituent as that (substituent ($R^{\alpha 0}$)) exemplified as an α-position substituent in the α-substituted acrylic ester can be used.

"Structural unit derived from a hydroxystyrene or a hydroxystyrene derivative" means a structural unit formed by cleavage of an ethylenic double bond of a hydroxystyrene or a hydroxystyrene derivative.

"Hydroxystyrene derivative" is a concept including includes those obtained by substituting an α-position hydrogen atom of hydroxystyrene with other substituents such as an alkyl group and a halogenated alkyl group, and derivatives thereof. Examples of the derivatives include a derivative obtained by substituting a hydrogen atom of a hydroxyl group of hydroxystyrene in which the α-position hydrogen atom may be substituted with a substituent with an organic group; and a derivative in which a substituent other than the hydroxyl group is bonded to a benzene ring of hydroxystyrene in which the α-position hydrogen atom may be substituted with a substituent. Here, the α-position (α-position carbon atom) means a carbon atom to which a benzene ring is bonded unless otherwise noted.

As the substituent with which the α-position hydrogen atom of the hydroxystyrene is substituted, the same substituent as that exemplified as an α-position substituent in the α-substituted acrylic ester can be used.

"Structural unit derived from a vinylbenzoic acid or a vinylbenzoic acid derivative" means a structural unit formed by cleavage of an ethylenic double bond of a vinylbenzoic acid or a vinylbenzoic acid derivative.

"Vinylbenzoic acid derivative" is a concept including those obtained by substituting an α-position hydrogen atom of a vinylbenzoic acid with other substituents such as an alkyl group and a halogenated alkyl group, and derivatives thereof. Examples of the derivatives include a derivative obtained by substituting a hydrogen atom of a carboxy group of the vinylbenzoic acid in which the α-position hydrogen atom may be substituted with a substituent with an organic group; and a derivative in which a substituent other than the hydroxyl group and the carboxy group is bonded to a benzene ring of the vinylbenzoic acid in which the α-position hydrogen atom may be substituted with an substituent. Here, the α-position (α-position carbon atom) means a carbon atom to which a benzene ring is bonded unless otherwise noted.

"Styrene" is a concept including styrene and those obtained by substituting an α-position hydrogen atom of the styrene with other substituents such as an alkyl group and a halogenated alkyl group.

"Styrene derivative" is a concept including those obtained by substituting the α-position hydrogen atom of the styrene with other substituents such as an alkyl group and a halogenated alkyl group, and the derivatives thereof. Examples of the derivatives include a derivative in which a substituent is bonded to a benzene ring of hydroxystyrene in which the α-position hydrogen atom may be substituted with a substituent. Here, the α-position (α-position carbon atom) means a carbon atom to which a benzene ring is bonded unless otherwise noted.

"Structural unit derived from the styrene" and "structural unit derived from the styrene derivative" mean structural units formed by cleavage of an ethylenic double bond of the styrene or the styrene derivative.

The alkyl group as the α-position substituent is preferably a linear or branched alkyl group, and specifically, examples thereof include an alkyl group having 1 to 5 carbon atoms (a methyl group, an ethyl group, a propyl group, an isopropyl group, an n-butyl group, an isobutyl group, a tert-butyl group, a pentyl group, an isopentyl group, and a neopentyl group).

In addition, specific examples of the halogenated alkyl group as the α-position substituent include a group obtained by substituting at least one or all of the hydrogen atoms of "the alkyl group as the α-position substituent" with a halogen atom. Examples of the halogen atom include a fluorine atom, a chlorine atom, a bromine atom, and an iodine atom, and particularly, a fluorine atom is preferable.

Further, specific examples of the hydroxyalkyl group as the α-position substituent include a group obtained by substituting at least one or all of the hydrogen atoms of the "alkyl group as the α-position substituent" with a hydroxyl group. The number of the hydroxyl groups in the hydroxyalkyl group is preferably 1 to 5, and most preferably 1.

Note that, the position numbers of the bonds in a 6-oxabicyclo [3.2.1$^{1,5}$] octane ring, and the position numbers of the bonds in a 3-oxatricyclo [4.2.1.0$^{4,8}$] nonane ring are indicated as follows.

[Chemical formula 2]

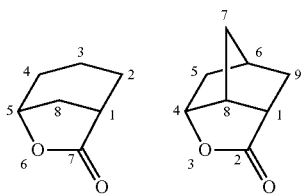

Resist Composition

A resist composition according to the first aspect of the present invention is a resist composition which generates an acid upon exposure and whose solubility in a developing solution changes under the action of the acid, and the resist composition includes a base material component (A) (hereinafter, also referred to as "(A) component") whose solubility in the developing solution changes under the action of the acid, and an acid diffusion control agent component (D) (hereinafter, also referred to as "(D) component").

When a resist film is formed by using the resist composition, and the resist film is selectively exposed to the light, an acid is generated in the exposed area of the resist film, and the solubility of the (A) component with respect to the developing solution is changed under the action of the acid; on the other hand, the solubility of the (A) component with respect to the developing solution is not changed in the unexposed area of the resist film. Therefore, a difference in the solubility in the developing solution occurs between the exposed area and the unexposed area. For this reason, when the resist film is developed, in a case where the resist composition is a positive-type, the exposed area of the resist film is dissolved and removed so as to form a positive-type resist pattern, and in a case where the resist composition is a negative-type, the unexposed area of the resist film is dissolved and removed so as to form a negative-type resist pattern.

In the present specification, the resist composition with which the exposed area of the resist film is dissolved and removed to form the positive-type resist pattern is referred to as a positive-type resist composition, and the resist composition with which the unexposed area of the resist film is dissolved and removed to form a negative-type resist pattern is referred to as a negative-type resist composition.

The resist composition of the present aspect may be a positive-type resist composition or a negative-type resist composition.

Further, the resist composition of the present aspect may be used for an alkali developing process in which an alkali developing solution is used for a developing treatment at the time of forming a resist pattern, or may be used for a solvent developing process in which a developing solution (an organic developing solution) containing an organic solvent is used for the developing treatment.

The resist composition of the present aspect has an acid generating ability to generate an acid upon exposure, and the (A) component may generate an acid upon exposure, and an additive component, which is compounded separately from the (A) component, may generate an acid upon exposure.

Specifically, the resist composition of the present aspect may be (1) a composition containing an acid generator component (B) (hereinafter, referred to as "(B) component") which generates an acid upon exposure, (2) the (A) component may be a component which generates an acid upon exposure, or (3) the (A) component may be the component which generates an acid upon exposure, and may further contain the (B) component.

That is, in a case of the above descriptions (2) and (3), the (A) component is "a base material component which generates an acid upon exposure, and of which the solubility in the developing solution is changed under the action of the acid". In a case where the (A) component is the base material component which generates an acid upon exposure, and of which the solubility in the developing solution is changed under the action of the acid, an (A1) component described below is preferably a polymer compound which generates an acid upon exposure, and of which the solubility in developing solution is changed under the action of the acid. Examples of such a polymer compound include a resin having a structural unit which generates an acid upon exposure. As the structural unit which generates an acid upon exposure, well-known structural units can be used.

Among the above-mentioned examples, the resist composition of the present aspect is particularly preferably the composition in the case of the above (1), that is, a composition containing the (A) component, the (D) component, and the (B) component (except for the (D) component).

(A) Component

The (A) component is a base material component whose solubility in a developing solution changes under action of an acid.

The "base material component" in the present invention is an organic compound having film forming ability, and is preferably an organic compound having the molecular weight of 500 or more. When the molecular weight of the organic compound is 500 or more, the film forming ability is improved, and a resist pattern at a nano level is easily formed.

The organic compound to be used as the base material component is generally classified into a non-polymer and a polymer.

Generally, a non-polymer having a molecular weight of 500 or more and less than 4,000 is used as the non-polymer. Hereinafter, a non-polymer having a molecular weight of 500 or more and less than 4,000 is referred to as a "low molecule compound".

Generally, a polymer having a molecular weight of 1,000 or more is used. Hereinafter, a polymer having a molecular weight of 1,000 or more is referred to as a "resin" or a "polymer compound".

As the molecular weight of the polymer, the mass average molecular weight expressed in terms of polystyrene by gel permeation chromatography (GPC) is used.

In a case where the resist composition of the present aspect is the "negative-type resist composition for an alkali developing process", which forms a negative-type resist pattern in the alkali developing process, or is the "positive-type resist composition for a solvent developing process", which forms a positive-type resist pattern in the solvent developing process, a base material component (A-2) (hereinafter, referred to as "(A-2) component") which is soluble in the alkali developing solution is preferably used as the (A) component, and a crosslinking agent component is further mixed thereto. In the resist composition, when the acid is generated from the (B) component upon exposure, the crosslinking occurs between the (A-2) component and the crosslinking agent component under the action of the acid, and as a result, the solubility in the alkali developing solution is decreased (the solubility in the organic developing solution is increased). For this reason, in the forming of the resist pattern, when the resist film obtained by coating the support with the resist composition is selectively exposed to the light, the solubility of the exposed area of the resist film is changed to sparing solubility in the alkali developing solution (the solubility in the organic developing solution); on the other hand, the solubility of the unexposed area of the resist film with respect to the alkali developing solution is not changed (sparing solubility in the organic developing solution), and thus a negative-type resist pattern is formed by developing the resist film with the alkali developing solution. At this time, a positive-type resist pattern is formed by developing the resist film with the organic developing solution.

Preferred examples of the (A-2) component include a resin (hereinafter, referred to as an "alkali-soluble resin") which is soluble to the alkali developing solution.

As the alkali-soluble resin, a resin having a structural unit derived from at least one selected from α-(hydroxyalkyl) acrylate and α-(hydroxyalkyl) acrylic acid alkyl ester (preferably, alkyl ester having 1 to 5 carbon atoms), which is disclosed in Japanese Unexamined Patent Application, Publication No. 2000-206694; an acrylic resin in which a hydrogen atom bonded to an α-position carbon atom having a sulfonamide group may be substituted with a substituent, or a polycycloolefin resin, which is disclosed in U.S. Pat. No. 6,949,325; an acrylic resin which contains fluorinated alcohol and in which a hydrogen atom boned to the α-position carbon atom may be substituted with a substituent, which is disclosed in U.S. Pat. No. 6,949,325, Japanese Unexamined Patent Application, Publication No. 2005-336452, and Japanese Unexamined Patent Application, Publication No. 2006-317803; and a polycycloolefin resin containing fluorinated alcohol, which is disclosed in Japanese Unexamined Patent Application, Publication No. 2006-259582 are preferably used from the aspect that it is possible to form an excellent resist pattern with little swelling.

Note that, the α-(hydroxyalkyl)acrylate represents one or both of an acrylic acid in which a hydrogen atom is bonded to the α-position carbon atom to which a carboxy group is bonded, and α-hydroxyalkyl acrylate in which a hydroxyalkyl group (preferably, a hydroxyalkyl group having 1 to 5 carbon atoms) is bonded to the α-position carbon atom, among acrylic acids in which a hydrogen atom bonded to the α-position carbon atom may be substituted with a substituent.

As the crosslinking agent component, an amino-based crosslinking agent such as glycoluril having a methylol group or an alkoxy methyl group, or a melamine-based crosslinking agent is preferably used from the aspect that it is easy to form an excellent resist pattern with little swelling. The mixing content of the crosslinking agent component is preferably 1 to 50 parts by mass with respect to 100 parts by mass of the alkali-soluble resin.

In a case where the resist composition of the present aspect is the "positive-type resist composition for an alkali developing process", which forms a positive-type resist pattern in the alkali developing process, or is "negative-type resist composition for a solvent developing process", which forms a negative-type resist pattern in the solvent developing process, a base material component (A-1) (hereinafter, referred to as "(A-1) component") of which the polarity is increased under the action of acid is preferably used as the (A) component. When the (A-1) component is used, the polarity of the base material component is changed before and after exposure, and thus it is possible to obtain satisfactory development contrast not only in the alkali developing process, but also in the solvent developing process.

In the case of the alkali developing process, the (A-1) component has the sparing solubility in the alkali developing solution before exposure, and for example, when an acid is generated from the (B) component upon exposure, the polarity is increased under the action of acid and thus the solubility in the alkali developing solution is increased. For this reason, in the forming of the resist pattern, when the resist film obtained by coating the support with the resist composition is selectively exposed to the light, the sparing solubility of the exposed area of the resist film is changed to be soluble in the alkali developing solution; on the other hand, the solubility of the unexposed area of the resist film remains to be alkali sparing solubility without being changed, and thus the positive-type resist pattern is formed by the alkali developing the resist film.

On the other hand, in the case of the solvent developing process, the (A-1) component has the solubility increased with respect to the organic developing solution before exposure, and when the acid is generated upon exposure, the polarity is increased under the action of acid, and thus the solubility in the organic developing solution is decreased. For this reason, in the forming of the resist pattern, when the resist film obtained by coating the support with the resist composition is selectively exposed to the light, the solubility of the exposed area of the resist film is changed to the sparing solubility in the organic developing solution; on the other hand, the solubility of the unexposed area of the resist film is not changed, and thus it is possible to impart contrast between the exposed area and unexposed area by developing the resist film with the organic developing solution, thereby forming the negative-type resist pattern.

The (A) component used in the resist composition of the present aspect contains a polymer compound (A1) (hereinafter, referred to as "(A1) component") having a structural unit (a0) represented by general formula (a0-1).

As the (A) component, at least the (A1) component is used, and other polymer compounds and/or a low molecule compound may be used together with the (A1) component.

In the resist composition of the present aspect, the (A) component is preferably the aforementioned (A-1) component. That is, the resist composition of the present aspect is preferably the "positive-type resist composition for an alkali developing process", which forms the positive-type resist pattern in the alkali developing process, or the "negative-type resist composition for a solvent developing process", which forms the negative-type resist pattern in the solvent developing process. In a case where the (A-1) component is used as the (A) component, the (A-1) component contains the (A1) component.

(A1) Component

The (A1) component is a polymer compound having a structural unit (a0) represented by general formula (a0-1).

Structural Unit (a0)

The structural unit (a0) is a structural unit represented by the following general formula (a0-1). In the forming of the resist pattern, when a polymer compound having the structural unit (a0) is used as a base resin, the roughness is reduced and the other lithography properties are improved.

[Chemical formula 3]

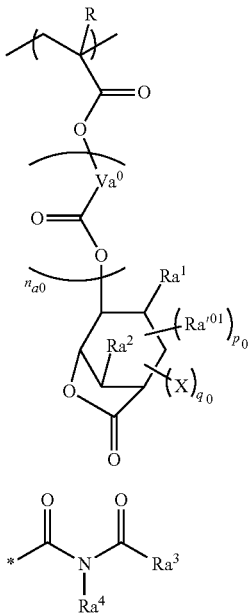

In the formula (a0-1), R is a hydrogen atom, an alkyl group having 1 to 5 carbon atoms or a halogenated alkyl group having 1 to 5 carbon atoms.

$Va^0$ is a divalent hydrocarbon group which may have a substituent.

$n_{a0}$ is an integer of 0 to 2.

$Ra^1$ and $Ra^2$ each independently represent a hydrogen atom, an alkyl group having 1 to 5 carbon atoms, an alkoxy group, or an alkylthio group, or $Ra^1$ and $Ra^2$ may be bonded to each other to form an alkylene group having 1 to 6 carbon atoms which may contain an oxygen atom or a sulfur atom; an ether bond; or a thioether bond.

$Ra^{'01}$ is a halogen atom; an alkyl group having 1 to 6 carbon atoms which may have a halogen atom; a hydroxyalkyl group having 1 to 6 carbon atoms, of which the hydroxy group may be protected by a protective group and which may have a halogen atom; a carboxy group which may form a salt; or a substituted oxycarbonyl group.

$p_0$ is an integer of 0 to 8. In a case where two or more $Ra^{'01}$'s are present, the plural $Ra^{'01}$'s may be the same as or different from each other.

X is a group represented by general formula (a0-r-1), a cyano group, a halogen atom, a halogenated alkyl group, —C(=O)O$Ra^5$, —OC(=O)$Ra^5$, —CON($Ra^6$)($Ra^7$), —SO$_2$N($Ra^8$)($Ra^9$), or —SO$_2$$Ra^0$. $Ra^5$ to $Ra^9$ each independently represent a hydrogen atom or an alkyl group. $Ra^0$ is an alkyl group. In the formula (a0-r-1), $Ra^3$ and $Ra^4$ each independently represent a hydrogen atom or a nonaromatic hydrocarbon group which may have a substituent, or $Ra^3$ and $Ra^4$ may be bonded to each other so as to form a ring with the carbon atom to which $Ra^3$ is bonded and the nitrogen atom to which $Ra^4$ is bonded. Note that, a symbol of * in the formula (a0-r-1) represents a bond.

$q_0$ is an integer of 1 to 9. In a case where two or more X's are present, the plural X's may be the same as or different from each other.

In the formula (a0-1), R is a hydrogen atom, an alkyl group having 1 to 5 carbon atoms or a halogenated alkyl group having 1 to 5 carbon atoms.

The alkyl group having 1 to 5 carbon atoms for R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group.

The halogenated alkyl group having 1 to 5 carbon atoms is a group obtained by substituting at least one or all of the hydrogen atoms of an alkyl group having 1 to 5 carbon atoms for R with a halogen atom. Examples of the halogen atom include a fluorine atom, a chlorine atom, a bromine atom, and an iodine atom, and particularly, a fluorine atom is preferable.

R is preferably a hydrogen atom, an alkyl group having 1 to 5 carbon atoms, or a fluorinated alkyl group having 1 to 5 carbon atoms, and a hydrogen atom or a methyl group is particularly preferable in terms of industrial availability.

In the formula (a0-1), $Va^0$ is a divalent hydrocarbon group which may have a substituent.

The hydrocarbon group for $Va^0$ may be an aliphatic hydrocarbon group, or may be an aromatic hydrocarbon group. The aliphatic hydrocarbon group means a hydrocarbon group having no aromaticity. The aliphatic hydrocarbon group as the divalent hydrocarbon group for $Va^0$ may be saturated or unsaturated, and is preferably saturated in general.

More specific examples of the aliphatic hydrocarbon group for $Va^0$ include a linear or branched aliphatic hydrocarbon group, or an aliphatic hydrocarbon group containing a ring in the structure.

The number of carbon atoms of the linear aliphatic hydrocarbon group is preferably 1 to 10, further preferably 1 to 6, still further preferably 1 to 4, and most preferably 1 to 3. As the linear aliphatic hydrocarbon group, a linear alkylene group is preferable. Specifically, examples thereof include a methylene group [—CH$_2$—], an ethylene group [—(CH$_2$)$_2$—], a trimethylene group [—(CH$_2$)$_3$—], a tetramethylene group [—(CH$_2$)$_4$—], and a pentamethylene group [—(CH$_2$)$_5$—].

The number of carbon atoms of the branched aliphatic hydrocarbon group is preferably 2 to 10, further preferably 2 to 6, still further preferably 2 to 4, and most preferably 2 or 3. As the branched aliphatic hydrocarbon group, a branched alkylene group is preferable. Specifically, examples thereof include an alkyl alkylene group such as an alkyl methylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; an alkyl ethylene group such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; an alkyl trimethylene group such as —CH(CH$_3$)CH$_2$CH$_2$— and —CH$_2$CH(CH$_3$)CH$_2$—; an alkyl tetramethylene group such as —CH(CH$_3$)CH$_2$CH$_2$CH$_2$— and —CH$_2$CH(CH$_3$)CH$_2$CH$_2$—. The alkyl group in the alkyl alkylene group is preferably a linear alkyl group having 1 to 5 carbon atoms.

As the aliphatic hydrocarbon group containing a ring in the structure, an aliphatic hydrocarbon group (a group in which two hydrogen atoms are removed from an aliphatic hydrocarbon ring), a group in which the alicyclic hydrocarbon group is bonded to a terminal of the linear or branched aliphatic hydrocarbon group, and a group in which the alicyclic hydrocarbon group is present in the middle of the linear or branched aliphatic hydrocarbon group. Examples of the linear or branched aliphatic hydrocarbon group include the same groups as described above.

The number of carbon atoms of the alicyclic hydrocarbon group is preferably 3 to 20, and further preferably 3 to 12.

The alicyclic hydrocarbon group may be a polycyclic group, and may be a monocyclic group. The monocyclic alicyclic hydrocarbon group is preferably a group obtained by removing two hydrogen atoms from the monocycloalkane. The number of the carbon atoms of the monocycloalkane is preferably 3 to 6, and specific examples thereof include cyclopentane and cyclohexane.

The polycyclic alicyclic hydrocarbon group is preferably a group obtained by removing two hydrogen atoms from the polycycloalkane, and the number of the carbon atoms of the polycycloalkane is preferably 7 to 12. Specific examples thereof include adamantane, norbornane, isobornane, tricyclodecane, and tetracyclododecane.

The aromatic hydrocarbon group for $Va^0$ is a hydrocarbon group having at least one aromatic ring. The aromatic ring is not particularly limited as long as it is a cyclic conjugated system having $(4n+2)$ π-electrons, and it may be monocyclic or polycyclic. The number of carbon atoms of the aromatic ring is preferably 5 to 30, further preferably 5 to 20, still further preferably 6 to 15, and particularly preferably 6 to 12. Specific examples of the aromatic ring include an aromatic hydrocarbon ring such as benzene, naphthalene, anthracene, and phenanthrene; and aromatic heterocycle in which at least one of carbon atoms forming the aromatic hydrocarbon ring is substituted with a heteroatom. Examples of the heteroatom in the aromatic heterocycle include an oxygen atom, a sulfur atom, and a nitrogen atom. Specific examples of the aromatic heterocycle include a pyridine ring and a thiophene ring.

Specific examples of the aromatic hydrocarbon group include a group (an arylene group or a heteroarylene group) obtained by removing two hydrogen atoms from the aromatic hydrocarbon ring or the aromatic heterocycle; a group obtained by removing two hydrogen atoms from an aromatic compound (for example, biphenyl and fluorene) containing two or more aromatic rings; and a group (a group obtained by further removing one hydrogen atom from the aryl group in an aryl alkyl group such as a benzyl group, a phenethyl group, a 1-naphtyl methyl group, a 2-naphtyl methyl group, a 1-naphtyl ethyl group, and a 2-naphtyl ethyl group) in which one hydrogen atom of a group (an aryl group or a heteroaryl group) obtained by removing one hydrogen atom from the aromatic hydrocarbon ring or the aromatic heterocycle is substituted with an alkylene group. The number of the carbon atoms of the alkylene group which is bonded to the aryl group or the heteroaryl group is preferably 1 to 4, further preferably 1 to 2, and particularly preferably 1.

Among them, the hydrocarbon group for $Va^0$ is preferably an aliphatic hydrocarbon group, further preferably a linear or branched aliphatic hydrocarbon group, still further preferably a linear aliphatic hydrocarbon group, and particularly preferably a linear alkylene group.

$Va^0$ may have a substituent. For example, as a case where a methylene group ($-CH_2-$) in the hydrocarbon group of $Va^0$ is substituted with a divalent group, an ether bond ($-O-$) is contained between carbon atoms of the divalent hydrocarbon group of $Va^0$. In this case, the number of the ether bonds present in $Va^0$ may be one or two or more. In addition, as a case where the hydrogen atom ($-H$) in the hydrocarbon group of $Va^0$ is substituted with monovalent group, the hydrogen atom ($-H$) in the hydrocarbon group of $Va^0$ is substituted with a fluorine atom or a fluorinated alkyl group having 1 to 5 carbon atoms. In this case, $Va^0$ is preferably $-CH_2CHF-$, $-CH(CH_2CH_3)\ CF_2-$, $-CH(CH_2CH_3)C(CF_3)F-$, or $-CH(CH_3)\ CF_2-$.

In the formula (a0-1), $n_{a0}$ is an integer of 0 to 2, preferably 0 or 1, and further preferably 0.

In the formula (a0-1), $Ra^1$ and $Ra^2$ each independently represent a hydrogen atom, an alkyl group having 1 to 5 carbon atoms, an alkoxy group, or an alkylthio group, or $Ra^1$ and $Ra^2$ may be bonded to each other so as to form an alkylene group having 1 to 6 carbon atoms, which may contain an oxygen atom or a sulfur atom, an ether bond, or a thioether bond.

The alkyl group having 1 to 5 carbon atoms for $Ra^1$ and $Ra^2$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group.

The alkoxy group for $Ra^1$ and $Ra^2$ is preferably a linear or branched alkoxy group, and specific examples thereof include a group in which an alkyl group such as those exemplified as $Ra^1$ and $Ra^2$ is linked to an oxygen atom ($-O-$).

An alkylthio group for $Ra^1$ and $Ra^2$ is preferably an alkylthio group having 1 to 4 carbon atoms, and specific examples thereof include a methylthio group, an ethylthio group, an n-propylthio group, an iso-propylthio group, an n-butylthio group, and a tert-butylthio group.

As an alkylene group having 1 to 6 carbon atoms in which $Ra^1$ and $Ra^2$ are bonded to each other, a linear or branched alkylene group is preferable, and examples thereof include a methylene group, an ethylene group, an n-propylene group, and an isopropylene group. In a case where the alkylene group contains an oxygen atom or a sulfur atom, specific examples thereof include a group in which $-O-$ or $-S-$ is present at a terminal of the alkylene group or between the carbon atoms, such as $-O-CH_2-$, $-CH_2-O-CH_2-$, $-S-CH_2-$, and $-CH_2-S-CH_2-$. A group in which $Ra^1$ and $Ra^2$ are bonded to each other is preferably an alkylene group having 1 to 6 carbon atoms or $-O-$, is further preferably an alkylene group having 1 to 6 carbon atoms, is still further preferably an alkylene group having 1 to 5 carbon atoms, and is particularly preferably a methylene group.

In the formula (a0-1), $Ra'^{01}$ is a halogen atom, an alkyl group having 1 to 6 carbon atoms which may have a halogen atom, a hydroxyalkyl group having 1 to 6 carbon atoms, of which the hydroxy group may be protected by a protective group and which may have a halogen atom, a carboxy group which may form a salt, or a substituted oxycarbonyl group.

Examples of the halogen atom for $Ra'^{01}$ include a fluorine atom, a chlorine atom, a bromine atom, and an iodine atom, and among them, the fluorine atom is particularly preferable.

Examples of the alkyl group having 1 to 6 carbon atoms for $Ra'^{01}$ include a methyl group, an ethyl group, an n-propyl group, an isopropyl group, an n-butyl group, an isobutyl group, an s-butyl group, a t-butyl group, a pentyl group, and a hexyl group, and among them, the alkyl group having 1 to 5 carbon atoms is preferable, the alkyl group having 1 to 4 carbon atoms is further preferable, the alkyl group having 1 to 3 carbon atoms is still further preferable, the methyl group or the ethyl group is particularly preferable, and the methyl group is most preferable. Examples of the halogen atom which the alkyl group having 1 to 6 carbon atoms for $Ra'^{01}$ may have include a fluorine atom, a chlorine atom, a bromine atom, and an iodine atom. Examples of the alkyl group having 1 to 6 carbon atoms, which may have a halogen atom include a chloroalkyl group such as a chloromethyl group; and a fluoroalkyl group (preferably, a fluoroalkyl group having 1 to 3 carbon atoms) such as a trifluoromethyl group, a 2,2,2-trifluoroethyl group, and a pentafluoroethyl group.

Examples of the hydroxyalkyl group having 1 to 6 carbon atoms for $Ra'^{01}$ include a hydroxymethyl group, a 2-hydroxyethyl group, a 1-hydroxyethyl group, a 3-hydroxypropyl group, a 2-hydroxypropyl group, a 4-hydroxybutyl group, and a 6-hydroxyhexyl group. Examples of the halogen atom which may be contained in a hydroxyalkyl group having 1 to 6 carbon atoms for $Ra'^{01}$ include a fluorine atom, a chlorine atom, a bromine atom, and an iodine atom, and among them, the fluorine atom is preferable. Examples of the hydroxyalkyl group which has 1 to 6 carbon atoms and has the halogen atom include a difluorohydroxymethyl group, a 1,1-difluoro-2-hydroxyethyl group, a 2,2-difluoro-2-hydroxyethyl group, and a 1,1,2,2-tetrafluoro-2-hydroxyethyl group. Among the hydroxyalkyl groups which have 1 to 6 carbon atoms and may have a halogen atom, a hydroxyalkyl group which has 1 to 3 carbon atoms and may have a halogen atom is preferable, a hydroxyalkyl group having 1 or 2 carbon atoms (preferably one carbon atom), or a hydroxyalkyl group having 1 or 2 carbon atoms (preferably one carbon atom) and a halogen atom is further preferable.

Examples of the protective group which protects the hydroxy group of the hydroxyalkyl group having 1 to 6 carbon atoms, which may have a halogen atom include a group which forms an ether bond or an acetal bond together with an oxygen atom which forms a hydroxy group such as a methyl group and a methoxymethyl group; and a group which forms an ester bond together with an oxygen atom which forms a hydroxy group such as an acetyl group and a benzoyl group.

The carboxy group which may form a salt for $Ra'^{01}$ is selected from the group consisting of a carboxy group, and a carboxy group (salt of the carboxy group) which forms a salt.

Examples of the carboxy group (salt of the carboxy group) which forms a salt for $Ra'^{01}$ include an alkali metal salt, an alkaline earth metal salt, and a transition metal salt.

Examples of the substituted oxycarbonyl group for $Ra'^{01}$ include an alkoxycarbonyl group in which an alkoxy group having 1 to 4 carbon atoms and a carbonyl group are bonded to each other (specifically, an alkyloxycarbonyl group such as a methoxycarbonyl group, an ethoxycarbonyl group, an isopropyloxycarbonyl group, and an n-propoxycarbonyl group; and an alkenyloxycarbonyl group such as a vinyloxycarbonyl group and an allyloxycarbonyl group), a cycloalkyloxycarbonyl group such as a cyclohexyloxycarbonyl group, and an aryloxycarbonyl group such as a phenyloxycarbonyl group.

Among the above-described examples, $Ra'^{01}$ is preferably an alkyl group having 1 to 6 carbon atoms which may have a halogen atom, a hydroxyalkyl group having 1 to 6 carbon atoms, of which the hydroxy group may be protected by a protective group and which may have a halogen atom, and a substituted oxycarbonyl group.

Among the alkyl groups having 1 to 6 carbon atoms, which may have a halogen atom, an alkyl group having 1 to 3 carbon atoms, or a halogenated alkyl group having 1 to 3 carbon atoms is further preferable, and a methyl group and a trifluoromethyl group are particularly preferable.

Among the hydroxyalkyl groups having 1 to 6 carbon atoms, of which the hydroxy group may be protected by the protective group and which may have a halogen atom, a hydroxyalkyl group having 1 to 3 carbon atoms, of which the hydroxy group may be protected by the protective group, or a hydroxyalkyl group, of which the hydroxy group may be protected by the protective group and which may have a halogen atom, is preferable, and a hydroxymethyl group of which the hydroxy group may be protected by a protective group such as an acetoxymethyl group is further preferable.

In the formula (a0-1), $p_0$ is an integer of 0 to 8, preferably an integer of 0 to 6, and further preferably an integer of 0 to 3.

In the structural unit represented by the formula (a0-1), in a case where two or more $Ra'^{01}$'s are present, the plural $Ra'^{01}$'s may be the same as or different from each other.

In the formula (a0-1), X is an electron withdrawing group, and is a group represented by general formula (a0-r-1), a cyano group (—CN), a halogen atom, a halogenated alkyl group, —C(=O)O$Ra^5$, —OC(=O)$Ra^5$, —CON($Ra^6$)($Ra^7$), —SO$_2$N($Ra^8$)($Ra^9$) or —SO$_2Ra^0$.

Regarding group (N-acylcarbamoyl group) represented by general formula (a0-r-1) for X In the formula (a0-r-1), $Ra^3$ and $Ra^4$ each independently represent a hydrogen atom, or a nonaromatic hydrocarbon group which may have a substituent, or $Ra^3$ and $Ra^4$ may be bonded to each other so as to form a ring with the carbon atom to which $Ra^3$ is bonded and the nitrogen atom to which $Ra^4$ is bonded. Note that, a symbol of * in the formula (a0-r-1) represents a bond.

Examples of the nonaromatic hydrocarbon group for $Ra^3$ and $Ra^4$ include a linear or branched aliphatic hydrocarbon group, or an aliphatic hydrocarbon group containing a ring in the structure.

Examples of the linear or branched aliphatic hydrocarbon group include an alkyl group, an alkenyl group, and an alkynyl group. Examples of the alkyl group include an alkyl group having 1 to 20 carbon atoms (preferably having 1 to 10 carbon atoms, further preferably having 1 to 6 carbon atoms, and particularly preferably having 1 to 4 carbon atoms) such as a methyl group, an ethyl group, a propyl group, an isopropyl group, a butyl group, an isobutyl group, an s-butyl group, a t-butyl group, a pentyl group, a hexyl group, a heptyl group, an octyl group, a 2-ethylhexyl group, a nonyl group, and a decyl group. Examples of the alkenyl group include an alkenyl group having 2 to 20 carbon atoms (preferably having 2 to 10 carbon atoms, and further preferably having 2 to 6 carbon atoms) such as a vinyl group, an allyl group, and a butenyl group. Examples of the alkynyl group include an alkynyl group having 2 to 20 carbon atoms (preferably having 2 to 10 carbon atoms, and further preferably having 2 to 6 carbon atoms) such as an ethynyl group and a propynyl group.

Examples of the aliphatic hydrocarbon group containing a ring in the structure include an alicyclic hydrocarbon group, a group in which the alicyclic hydrocarbon group is bonded to a terminal of the linear or branched aliphatic hydrocarbon group, and a group in which the alicyclic hydrocarbon group is present in the middle of the linear or branched aliphatic hydrocarbon group.

Examples of the alicyclic hydrocarbon group include a cycloalkyl group of 3- to 8-membered rings such as a cyclopropyl group, a cyclobutyl group, a cyclopentyl group, a cyclohexyl group, a cycloheptyl group, and a cyclooctyl group; a cycloalkenyl group of 3- to 8-membered rings such as a cyclopentenyl group and a cyclohexenyl group; a cross-linked cyclic hydrocarbon group having 4 to 20 carbon atoms (preferably 7 to 12 carbon atoms) such as an adamantyl group and a norbornyl group.

As the aforementioned linear or branched aliphatic hydrocarbon group, the same linear or branched aliphatic hydrocarbon groups as those for $Ra^3$ and $Ra^4$ are used.

Among them, as the nonaromatic hydrocarbon group for $Ra^3$ and $Ra^4$, an alkyl group having 1 to 20 carbon atoms (preferably having 1 to 10 carbon atoms, further preferably having 1 to 6 carbon atoms, and particularly preferably having 1 to 4 carbon atoms), a cycloalkyl group of 3- to 8-membered rings (preferably 5- or 6-membered ring), a cross-linked cyclic hydrocarbon group having 4 to 20 carbon atoms (preferably 7 to 12 carbon atoms), or a group in which two or more of the aforementioned groups are bonded to each other is preferable.

Examples of the substituent which may be contained in the nonaromatic hydrocarbon group for $Ra^3$ and $Ra^4$ include a halogen atom such as a fluorine atom, an alkoxy group (for example, an alkoxy group having 1 to 6 carbon atoms) such as a hydroxy group and a methoxy group, an alkoxycarbonyl group (for example, an alkoxy-carbonyl group having 1 to 6 carbon atoms) such as a carboxy group, and a methoxycarbonyl group, an acyl group (for example, an acyl group having 1 to 6 carbon atoms) such as an acetyl group, an aryl group (for example, an aryl group having 6 to 14 carbon atoms) such as a cyano group and a phenyl group, an alkyl group (for example, an alkyl group having 1 to 20 carbon atoms, an alkyl group having 1 to 10 carbon atoms is preferable, and an alkyl group having 1 to 6 carbon atoms is further preferable) such as a methyl group, an alkenyl group (for example, an alkenyl group having 2 to 6 carbon atoms) such as a vinyl group, a cycloalkyl group (for example, a cycloalkyl group having 3 to 12 carbon atoms) such as a cyclohexyl group, and a nitro group.

Examples of the ring which may be formed of the carbon atom to which $Ra^3$ is bonded and the nitrogen atom to which $Ra^4$ is bonded by bonding $Ra^3$ and $Ra^4$ to each other include a nonaromatic nitrogen-containing heterocycle of 4- to 12-membered rings (preferably 5- or 6-membered ring) such as a β-lactam ring (4-membered ring), a γ-lactam ring (5-membered ring), and a δ-lactam ring (6-membered ring).

A substituent may be bonded to the aforementioned ring. Examples of the substituent include a substituent which is the same as the substituent which may be contained in the nonaromatic hydrocarbon group for $Ra^3$ and $Ra^4$, and among them, an alkyl group is preferable, and an alkyl group having 1 to 6 carbon atoms is further preferable.

Among the above-described examples, as $Ra^3$ and $Ra^4$, a hydrogen atom, an alkyl group having 1 to 20 carbon atoms (preferably having 1 to 10 carbon atoms, further preferably having 1 to 6 carbon atoms, and particularly preferably having 1 to 4 carbon atoms), a cycloalkyl group of 3- to 8-membered rings (preferably 5- or 6-membered ring), and a cross-linked cyclic hydrocarbon group having 4 to 20 carbon atoms (preferably 7 to 12 carbon atoms) are preferable.

In addition, it is preferable to form a nonaromatic nitrogen-containing heterocycle of 4- to 12-membered rings (preferably 5 to 6-membered rings) with the carbon atom to which $Ra^3$ is bonded and the nitrogen atom to which $Ra^4$ is bonded by bonding $Ra^3$ and $Ra^4$ to each other.

Further, $Ra^4$ is preferably a hydrogen atom in terms of the affinity with the alkali developing solution (having an acidic functional group).

Particularly, a combination in which $Ra^3$ is an alkyl group having 1 to 6 carbon atoms (most preferably having 1 to 4 carbon atoms) and $Ra^4$ is a hydrogen atom; a combination in which $Ra^3$ is a cycloalkyl group of 3- to 8-membered rings (preferably 5- or 6-membered ring) and $Ra^4$ is a hydrogen atom; or a combination in which $Ra^3$ is a cross-linked cyclic hydrocarbon group having 4 to 20 carbon atoms (preferably 7 to 12 carbon atoms), and $Ra^4$ is a hydrogen atom is preferable. Among them, the combination in which $Ra^3$ is an alkyl group having 1 to 6 carbon atoms (most preferably having 1 to 4 carbon atoms) and $Ra^4$ is a hydrogen atom is particularly preferable.

Regarding halogen atom and halogenated alkyl group for X

Examples of the halogen atom in X include a fluorine atom, a chlorine atom, a bromine atom, and an iodine atom.

The halogenated alkyl group for X is a group in which at least one or all of the hydrogen atoms of an alkyl group is substituted with a halogen atom. Examples of the halogen atom include a fluorine atom, a chlorine atom, a bromine atom, and an iodine atom, and among them, the fluorine atom is particularly preferable. Here, the alkyl group is preferably an alkyl group having 1 to 5 carbon atoms, and further preferably a linear or branched alkyl group having 1 to 5 carbon atoms.

Regarding —C(=O)O$Ra^5$, —OC(=O)$Ra^5$, —CON($Ra^6$)($Ra^7$), —SO$_2$N ($Ra^8$)($Ra^9$), or —SO$_2Ra^0$ for X $Ra^5$ to $Ra^9$ each independently represent a hydrogen atom or an alkyl group. The alkyl group for $Ra^5$ to $Ra^9$ is preferably an alkyl group having 1 to 5 carbon atoms, and further preferably a linear or branched alkyl group having 1 to 5 carbon atoms.

$Ra^0$ is an alkyl group, preferably an alkyl group having 1 to 5 carbon atoms, and further preferably a linear or branched alkyl group having 1 to 5 carbon atoms.

In the formula (a0-1), $q_0$ is an integer of 1 to 9, preferably an integer of 1 to 5, and further preferably 1 or 2.

In the structural unit represented by the formula (a0-1), in a case where two or more X's are present, the plural X's may be the same as or different from each other.

In a case where $Ra^1$ and $Ra^2$ are not bonded to each other in the formula (a0-1), X may be bonded to any position of 1-position, 2-position, 3-position, 4-position, 5-position, and 8-position of a 6-oxabicyclo[3.2.1$^{1,5}$]octane ring, and among them, X is preferably bonded to the 1-position (α-position of lactone) or 2-position, and is particularly preferably bonded to the 1-position (α-position of lactone).

In a case where $Ra^1$ and $Ra^2$ are bonded to each other, X may be bonded to any position of 1-position, 4-position, 5-position, 6-position, 7-position, 8-position, and 9-position of a 3-oxatricyclo [4.2.1.0$^{4,8}$] nonane ring, and among them, X is preferably bonded to 1-position or 9-position (or the position corresponding to this position) of a 3-oxatricyclo [4.2.1.0$^{4,8}$] nonane ring, and is particularly preferably bonded to the 1-position (or the position corresponding to this position; α-position of lactone).

Among the above examples, X is preferably at least one selected from the group consisting of a group represented by general formula (a0-r-1), a cyano group (—CN), —C(=O)O$Ra^5$, —OC(=O)$Ra^5$, —CON ($Ra^6$)($Ra^7$), —SO$_2$N ($Ra^8$)($Ra^9$), and —SO$_2Ra^0$, and is further preferably at least one selected from the group consisting of the group represented by general formula (a0-r-1), the cyano group (—CN), —C(=O)O$Ra^5$, —OC(=O)$Ra^5$, and —CON ($Ra^6$)($Ra^7$). Among them, X is still further preferably at least one selected from the group consisting of the group represented by general formula (a0-r-1) and a cyano group (—CN), and particularly preferably the cyano group (—CN).

Hereinafter, specific examples of the structural unit (a0) are described.

In the following respective formulae, $R^α$ represents a hydrogen atom, a methyl group, or a trifluoromethyl group. $n_α$ is 0 or 1.

X is the same as the X in the formula (a0-1), further preferably a group represented by general formula (a0-r-1) or a cyano group (—CN), and particularly preferably the cyano group (—CN).
[Chemical formula 4]
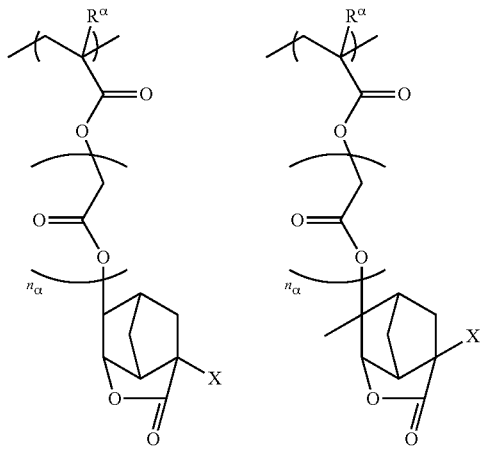
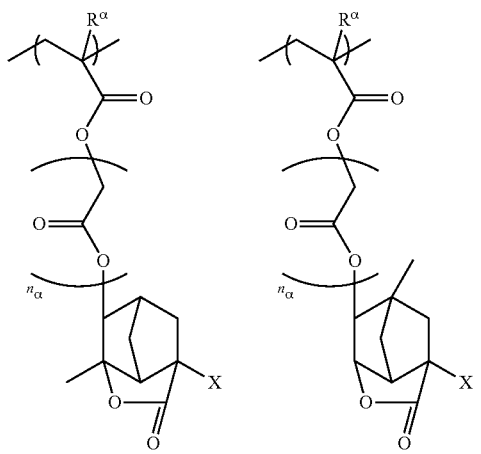
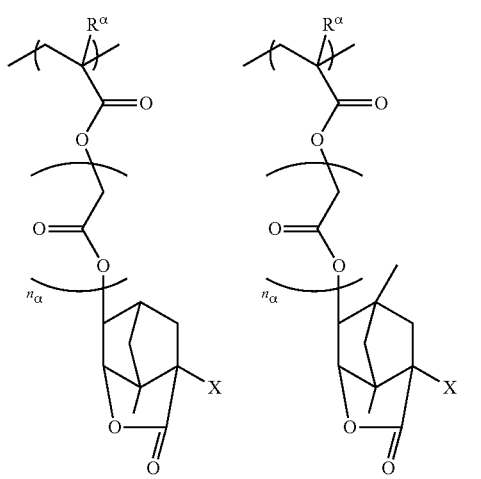
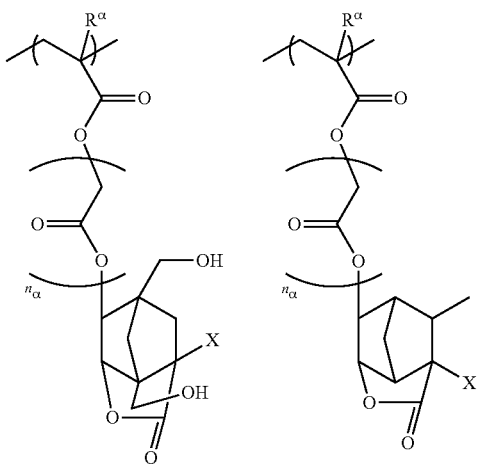
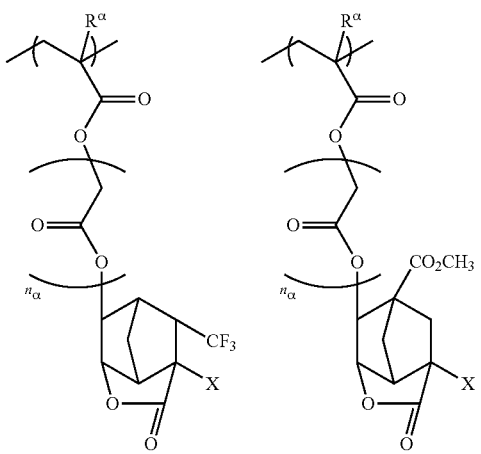
[Chemical formula 5]
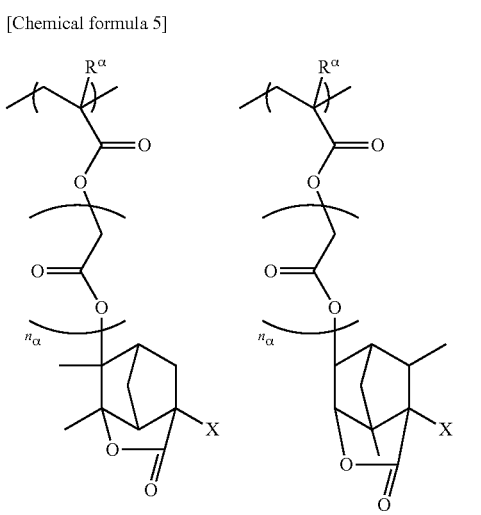

-continued

[Chemical formula 6]

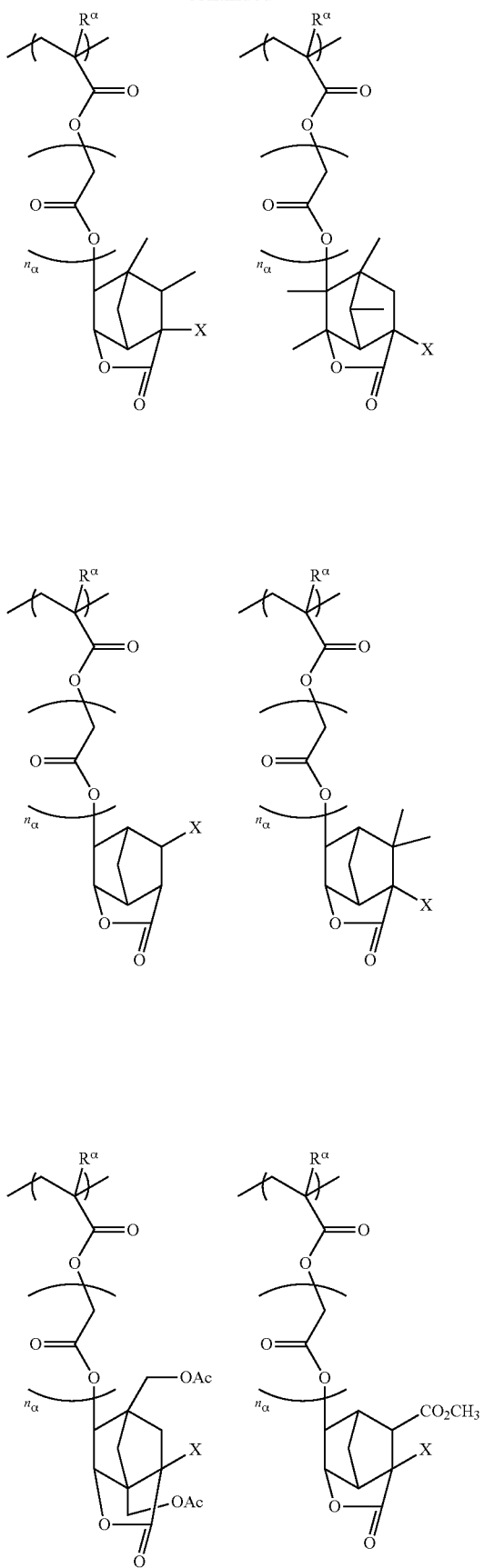
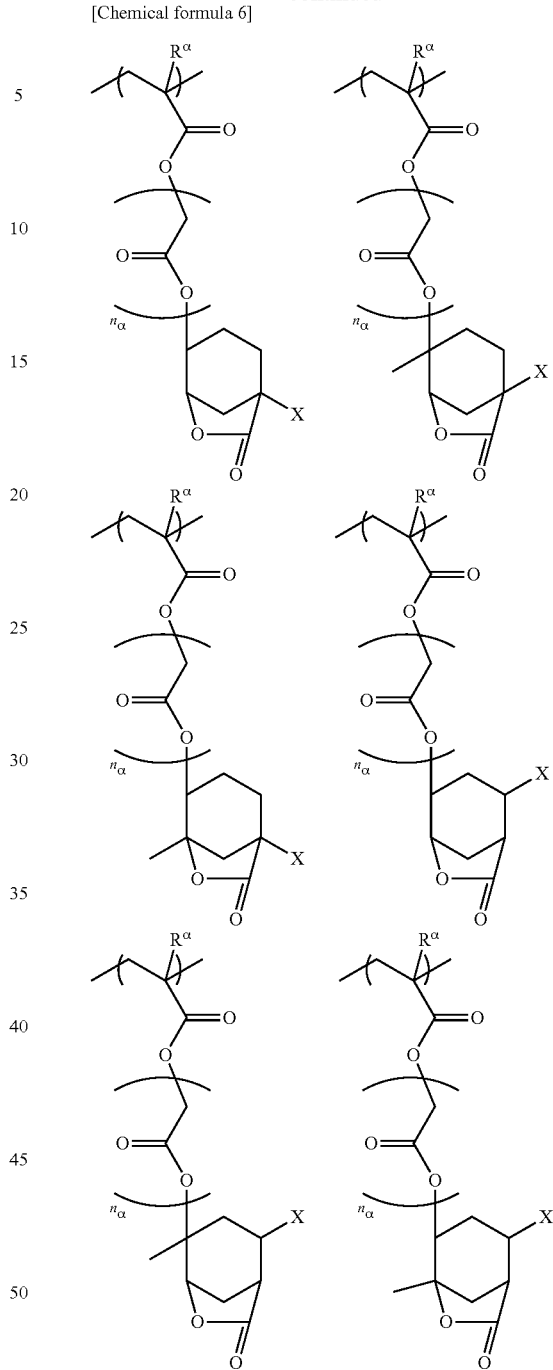

The structural unit (a0) of the (A1) component may be one or two or more types.

The ratio of the structural unit (a0) in the (A1) component is preferably 1 to 90 mol %, further preferably 5 to 80 mol %, still further preferably 10 to 70 mol %, and particularly preferably 20 to 60 mol %, with respect to the entire structural units for constituting the (A1) component.

When the ratio of the structural unit (a0) is set to be equal to or greater than the preferred lower limit, the lithography properties are more improved, for example, the roughness is reduced. In addition, the sensitivity is also likely to be increased. On the other hand, when the ratio of the structural unit (a0) is set to be equal to or less than the preferred upper limit, it is easy to obtain a resist pattern having an excellent shape while maintaining high sensitivity.

Other Structural Units

The (A1) component may have other structural units in addition to the structural unit (a0).

Other structural units are not particularly limited as long as those are structural units which do not belong to the structural unit (a0), and conventionally well-known structural units which are used for a resist resin for ArF excimer laser or KrF excimer laser (preferably, for ArF excimer laser) can be used, and examples thereof include the following structural units (a1) to (a4), and a structural unit which generates an acid upon exposure.

Structural Unit (a1):

In the resist composition of the present aspect, it is preferable that the (A1) component further has a structural unit (a1) containing an acid-decomposable group in which the polarity is increased under the action of acid in addition to the structural unit (a0).

In a case where the resist composition of the present aspect contains a polymer compound having the structural unit (a0) and the structural unit (a1), when the resist film formed by using the resist composition is exposed to the light, at least a portion of bonds of the structural unit (a1) is cleaved under the action of the acid, and thus the polarity is increased in the resist film. As such, the polarity of the (A1) component is changed before and after the exposure, and thus when the (A1) component is used, it is possible to obtain satisfactory development contrast not only in the alkali developing process, but also in the solvent developing process. Therefore, the resist composition of the present aspect is the positive-type in the alkali developing process, and is the negative-type in the solvent developing process.

The "acid-decomposable group" is a group having the acid decomposability with which at least a portion of the bonds in the structure of the acid-decomposable group can be cleaved under the action of the acid.

Examples of the acid-decomposable group in which the polarity is increased under the action of the acid include a group which is decomposed under the action of the acid so as to generate a polar group.

Examples of the polar group include a carboxy group, a hydroxyl group, an amino group, and a sulfo group (—SO$_3$H). Among them, a polar group containing —OH in the structure (hereinafter, referred to as an "OH-containing polar group" in some cases) is preferable, the carboxy group or the hydroxyl group is further preferable, and the carboxy group is particularly preferable.

Specific examples of the acid-decomposable group include a group in which the polar group is protected by an acid dissociable group (for example, a hydrogen atom of an OH-containing polar group is protected by an acid dissociable group).

Here, the "acid dissociable group" means both (i) a group having the acid dissociablity with which the bond between the acid dissociable group and the atom adjacent to the acid dissociable group can be cleaved under the action of acid, and (ii) a group in which the bond between the acid dissociable group and the atom adjacent to the acid dissociable group can be cleaved due to decarboxylation after a portion of the bond is cleaved under the action of the acid.

The acid dissociable group for constituting an acid-decomposable group is required to be a group having the lower polarity than that of the polar group generated by dissociation of the acid dissociable group, and with this, when the acid dissociable group is dissociated under the action of the acid, a polar group having the higher polarity than that of the acid dissociable group is generated, and thereby the polarity is increased. As a result, the polarity of the entire (A1) components is increased. As the polarity is increased, the solubility in the developing solution is relatively changed, and in a case where the developing solution is an alkali developing solution, the solubility is increased; whereas, in a case where the developing solution is an organic developing solution, the solubility is decreased.

Examples of the acid dissociable group include a group which has been proposed as an acid dissociable group for abase resin for chemically amplified resist.

Specific examples of the group which has been proposed as an acid dissociable group of a base resin for chemically amplified resist include an "acetal-type acid dissociable group", a "tertiary alkyl ester-type acid dissociable group", and a "tertiary alkyloxycarbonyl acid dissociable group" which are described as follows.

Acetal-Type Acid Dissociable Group:

Among the polar groups, examples of the acid dissociable group which protects a carboxy group or a hydroxyl group include an acid dissociable group (hereinafter, referred to as the "acetal-type acid dissociable group" in some cases) represented by the following general formula (a1-r-1).

[Chemical formula 7]

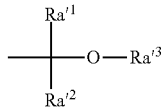

(a1-r-1)

[In the formula, $Ra'^1$ and $Ra'^2$ are a hydrogen atom or an alkyl group, $Ra'^3$ is a hydrocarbon group, and $Ra'^3$ may form a ring by bonding to any of $Ra'^1$ and $Ra'^2$.]

In the formula (a1-r-1), it is preferable that at least one of $Ra'^1$ and $Ra'^2$ is a hydrogen atom, and it is further preferable that both of them are a hydrogen atom.

In a case where $Ra'^1$ or $Ra'^2$ is an alkyl group, examples of the alkyl group include the same alkyl group as that exemplified as a substituent which may be bonded to the α-position carbon atom in the description of the α-substituted acrylic ester, and an alkyl group having 1 to 5 carbon atoms is preferable. Specifically, a linear or branched alkyl group is preferable. More specifically, examples thereof include a methyl group, an ethyl group, a propyl group, an isopropyl group, an n-butyl group, an isobutyl group, a tert-butyl group, a pentyl group, an isopentyl group, and a neopentyl group, and among them, the methyl group or the ethyl group is further preferable, and the methyl group is particularly preferable.

In the formula (a1-r-1), examples of the hydrocarbon group of $Ra'^3$ include a linear or branched alkyl group, and a cyclic hydrocarbon group.

The number of the carbon atoms of the linear alkyl group is preferably 1 to 5, further preferably 1 to 4, and still further preferably 1 or 2. Specific examples thereof include a methyl group, an ethyl group, an n-propyl group, an n-butyl group, and an n-pentyl group. Among them, the methyl group, the ethyl group, or the n-butyl group is preferable, and the methyl group or the ethyl group is further preferable.

The number of the carbon atoms of the branched alkyl group is preferably 3 to 10, and further preferably 3 to 5. Specific examples thereof include an isopropyl group, an isobutyl group, a tert-butyl group, an isopentyl group, a neopentyl group, a 1,1-diethyl propyl group, and a 2,2-dimethyl butyl group, and among them, the isopropyl group is preferable.

In a case where Ra'³ is a cyclic hydrocarbon group, the hydrocarbon group may be an aliphatic hydrocarbon group or an aromatic hydrocarbon group, and may be a polycyclic group or a monocyclic group.

The aliphatic hydrocarbon group which is a monocyclic group is preferably a group obtained by removing one hydrogen atom from monocycloalkane. The number of carbon atoms of the monocycloalkane is preferably 3 to 6, and specific examples thereof include cyclopentane and cyclohexane.

Examples of the aliphatic hydrocarbon group which is the polycyclic group include a group obtained by removing one hydrogen atom from polycycloalkane. The number of the carbon atoms of polycycloalkane is preferably 7 to 12, and specific examples thereof include adamantane, norbornane, isobornane, tricyclodecane, and tetracyclododecane.

In a case where the cyclic hydrocarbon group of Ra'³ is an aromatic hydrocarbon group, the aromatic hydrocarbon group is a hydrocarbon group having at least one aromatic ring.

The aromatic ring is not particularly limited as long as it is a cyclic conjugated system having (4n+2) π-electrons, and it may be monocyclic or polycyclic. The number of the carbon atoms of the aromatic ring is preferably 5 to 30, further preferably 5 to 20, is still further preferably 6 to 15, and particularly preferably 6 to 12. Specific examples of the aromatic ring include an aromatic hydrocarbon ring such as benzene, naphthalene, anthracene, and phenanthrene; and aromatic heterocycle in which a portion of carbon atoms forming the aromatic hydrocarbon ring is substituted with a heteroatom. Examples of the heteroatom in the aromatic heterocycle include an oxygen atom, a sulfur atom, and a nitrogen atom. Specific examples of the aromatic heterocycle include a pyridine ring and a thiophene ring.

Specific examples of the aromatic hydrocarbon group in Ra'³ include a group (an aryl group or a heteroaryl group) obtained by removing one hydrogen atom from an aromatic hydrocarbon ring or an aromatic heterocycle; a group obtained by removing one hydrogen atom from an aromatic compound (for example, biphenyl and fluorene) containing two or more aromatic rings; and a group (for example, an aryl alkyl group such as a benzyl group, a phenethyl group, a 1-naphtyl methyl group, a 2-naphtyl methyl group, a 1-naphtyl ethyl group, and a 2-naphtyl ethyl group) obtained by substituting one hydrogen atom of the aromatic hydrocarbon ring or the aromatic heterocycle with an alkylene group. The number of the carbon atoms of the alkylene group which is bonded to the aromatic hydrocarbon ring or the aromatic heterocycle is preferably 1 to 4, further preferably 1 to 2, and particularly preferably 1.

In a case where Ra'³ forms a ring by bonding to any one of Ra'¹ and Ra'², the cyclic group is preferably a group of 4- to 7-membered rings, and further preferably a group of 4- to 6-membered rings. Specific examples of the cyclic group include a tetrahydropyranyl group and a tetrahydrofuranyl group.

Tertiary Alkyl Ester-Type Acid Dissociable Group:

Among the polar groups, examples of the acid dissociable group which protects a carboxy group include an acid dissociable group represented by the following general formula (a1-r-2). Note that, among acid dissociable groups represented by the following formula (a1-r-2), an acid dissociable group consisting of an alkyl group is referred to as a "tertiary alkyl ester-type acid dissociable group" in some cases for the sake of convenience.

[Chemical formula 8]

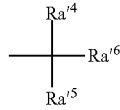

(a1-r-2)

[In the formula, Ra'⁴ to Ra'⁶ each independently represent a hydrocarbon group, and Ra'⁵ and Ra'⁶ may be bonded to each other so as to form a ring.]

Examples of the hydrocarbon group for Ra'⁴ to Ra'⁶ include the same as those exemplified for the hydrocarbon group for Ra'³.

Ra'⁴ is preferably an alkyl group having 1 to 5 carbon atoms. In a case where Ra'⁵ and Ra'⁶ are bonded to each other so as to forma ring, a group represented by the following general formula (a1-r2-1) can be exemplified. On the other hand, in a case where Ra'⁴ to Ra'⁶ are not bonded to each other and are each independently a hydrocarbon group, a group represented by the following general formula (a1-r2-2) can be exemplified.

[Chemical formula 9]

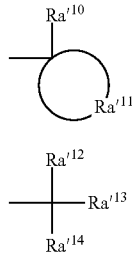

(a1-r2-1)

(a1-r2-2)

[In the formula, Ra'¹⁰ represents an alkyl group having 1 to 10 carbon atoms, Ra'¹¹ represents a group which forms an aliphatic cyclic group together with a carbon atom to which Ra'¹⁰ is bonded, and Ra'¹² to Ra'¹⁴ each independently represent a hydrocarbon group.]

In the formula (a1-r2-1), an alkyl group having 1 to 10 carbon atoms for Ra'¹⁰ is preferably a group which is exemplified as a linear or branched alkyl group for Ra'³ in the formula (a1-r-1). In the formula (a1-r2-1), an aliphatic cyclic group which is formed together with the carbon atom to which Ra'¹⁰ is bonded as Ra'¹¹ is preferably a group exemplified as an aliphatic hydrocarbon group which is a monocyclic group or a polycyclic group for Ra'³ in the formula (a1-r-1).

In the formula (a1-r2-2), it is preferable that Ra'¹² and Ra'¹⁴ each independently represent an alkyl group having 1 to 10 carbon atoms. The alkyl group is further preferably a group exemplified as a linear or branched alkyl group for Ra'³ in the formula (a1-r-1), a linear alkyl group having 1 to 5 carbon atoms is still further preferable, and a methyl group or an ethyl group is particularly preferable.

In the formula (a1-r2-2), Ra'¹³ is preferably a linear or branched alkyl group, or an aliphatic hydrocarbon group which is a monocyclic group or a polycyclic group, which is exemplified as the hydrocarbon group for Ra'³ in the formula (a1-r-1). Among them, a group exemplified as an aliphatic hydrocarbon group which is a monocyclic group or a polycyclic group for Ra'³ is further preferable.

Specific examples of the group represented by the formula (a1-r2-1) are shown below. "*" represents a bond (hereinafter, the same is applicable in the present specification).
[Chemical formula 10]
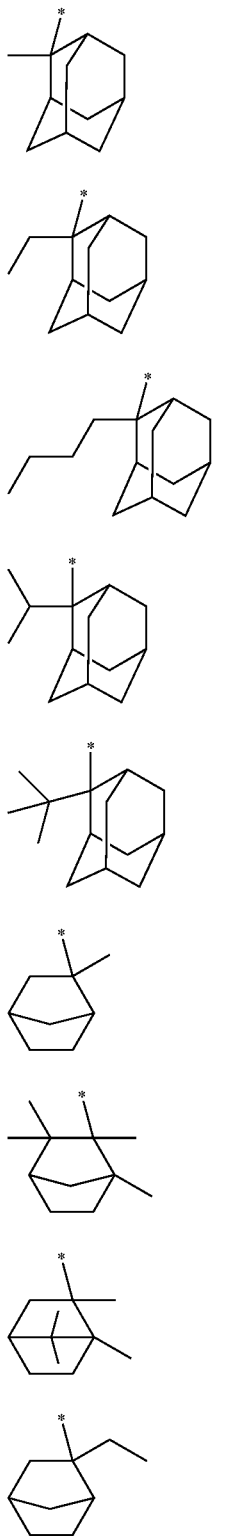
(r-pr-m1)
(r-pr-m2)
(r-pr-m3)
(r-pr-m4)
(r-pr-m5)
(r-pr-m6)
(r-pr-m7)
(r-pr-m8)
(r-pr-m9)
(r-pr-m10)
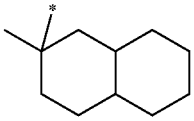
(r-pr-m11)
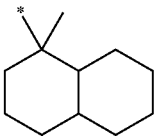
(r-pr-m12)
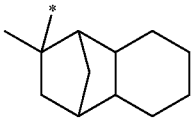
(r-pr-m13)
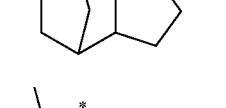
(r-pr-m14)
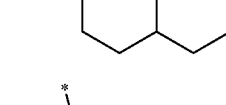
(r-pr-m15)
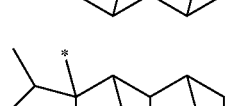
(r-pr-m16)
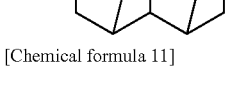
(r-pr-m17)
[Chemical formula 11]
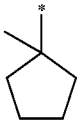
(r-pr-s1)
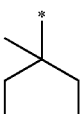
(r-pr-s2)
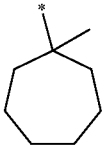
(r-pr-s3)

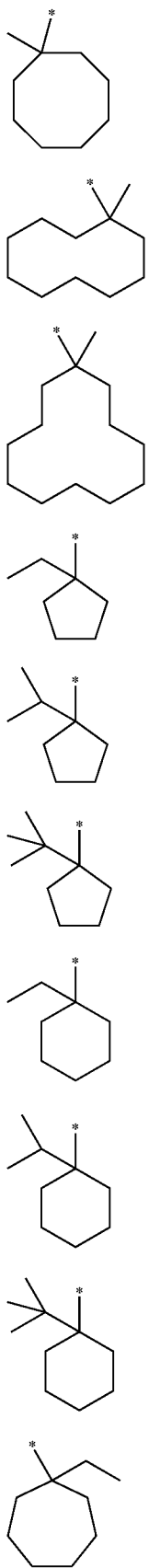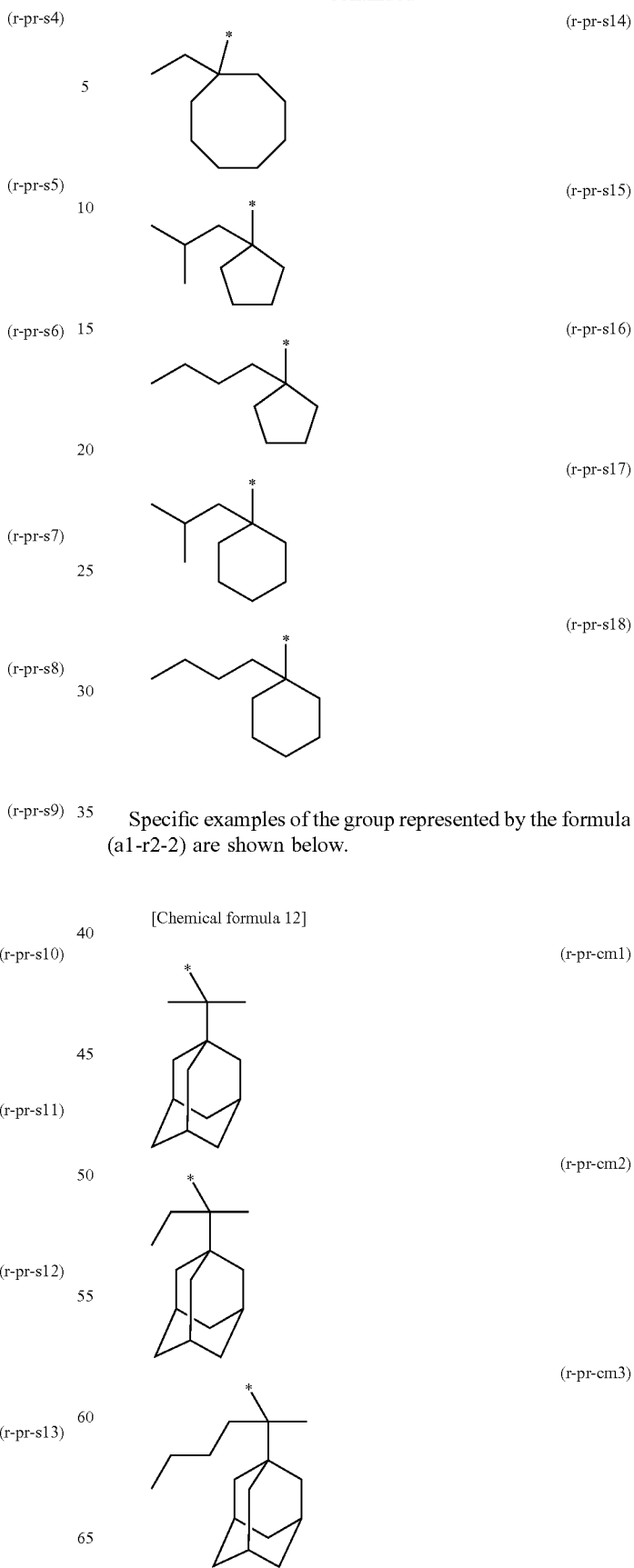
Specific examples of the group represented by the formula (a1-r2-2) are shown below.
[Chemical formula 12]

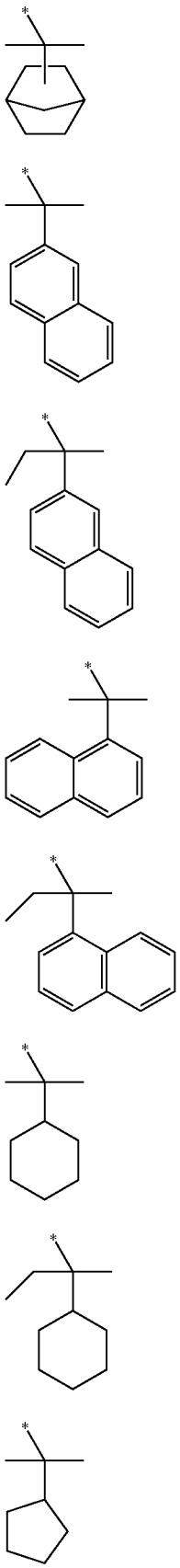

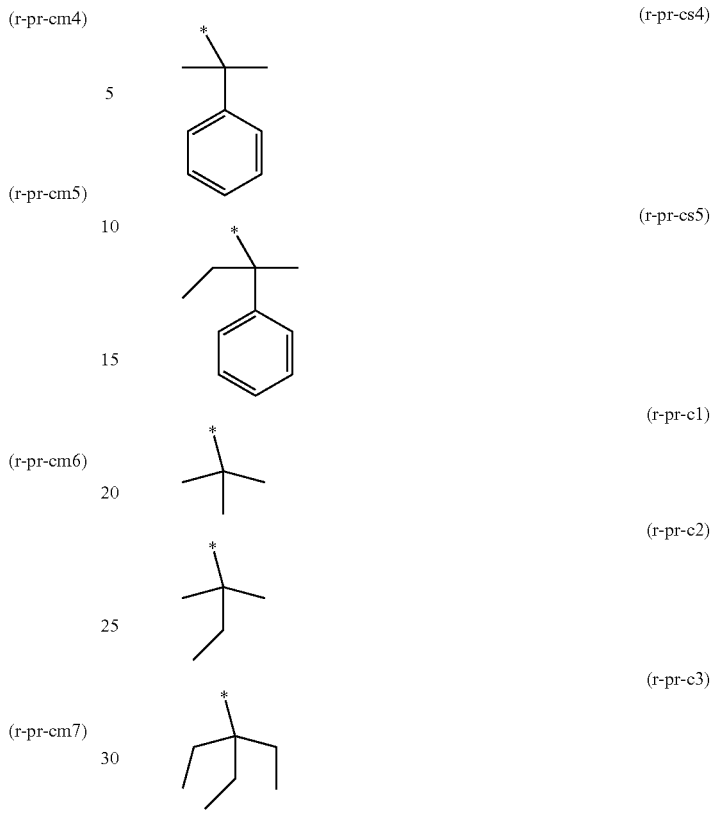

Tertiary Alkyloxycarbonyl Acid Dissociable Group:

Among the polar groups, examples of the acid dissociable group which protects a hydroxyl group include an acid dissociable group (hereinafter, referred to as the "tertiary alkyloxycarbonyl acid dissociable group" in some cases for the sake of convenience) represented by the following general formula (a1-r-3).

[Chemical formula 13]

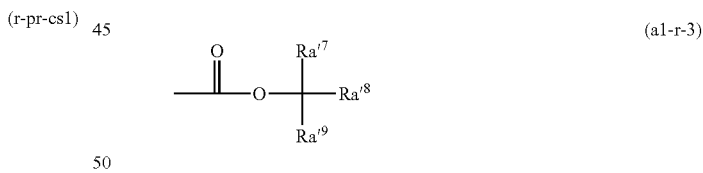

[In the formula, $Ra'^7$ to $Ra'^9$ each independently represent an alkyl group.]

In the formula (a1-r-3), $Ra'^7$ to $Ra'^9$ each are preferably an alkyl group having 1 to 5 carbon atoms, and are further preferably an alkyl group having 1 to 3 carbon atoms.

In addition, the total number of the carbon atoms of the respective alkyl groups is preferably 3 to 7, further preferably 3 to 5, and most preferably 3 or 4.

Examples of the structural unit (a1) include a structural unit derived from acrylic ester which may be obtained by substituting a hydrogen atom bonded to an α-position carbon atom with a substituent, a structural unit derived from acrylamide, a structural unit in which the hydrogen atom of at least one hydroxyl group in the structural unit derived from a hydroxystyrene or a hydroxystyrene derivative is protected by a substituent containing the acid-decomposable group, and a structural unit in which the hydrogen atom in at least one —C(=O)—OH in the structural unit derived from a vinylbenzoic acid or a vinylbenzoic acid derivative is protected by a substituent containing the acid-decomposable group.

Among them, the structural unit (a1) is preferably the structural unit derived from acrylic ester which may be obtained by substituting a hydrogen atom bonded to an α-position carbon atom with a substituent.

Preferred examples of the structural unit (a1) include a structural unit represented by the following general formula (a1-1) or (a1-2).

[Chemical formula 14]

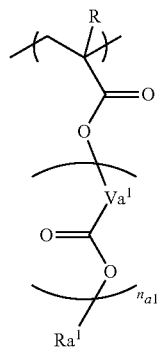

(a1-1)

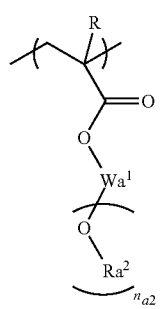

(a1-2)

[In the formula, R is a hydrogen atom, an alkyl group having 1 to 5 carbon atoms, or a halogenated alkyl group having 1 to 5 carbon atoms. $Va^1$ is a divalent hydrocarbon group which may have an ether bond, $n_{a1}$ is an integer of 0 to 2, and $Ra^1$ is an acid dissociable group represented by the formula (a1-r-1) or (a1-r-2). $Wa^1$ is ($n_{a2}$+1) valent hydrocarbon group, $n_{a2}$ is integer of 1 to 3, $Ra^2$ is an acid dissociable group represented by the formula (a1-r-1) or (a1-r-3).]

In the formula (a1-1), an alkyl group having 1 to 5 carbon atoms of R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. A halogenated alkyl group having 1 to 5 carbon atoms is a group obtained by substituting at least one or all of the hydrogen atoms of an alkyl group having 1 to 5 carbon atoms with a halogen atom. Examples of the halogen atom include a fluorine atom, a chlorine atom, a bromine atom, and an iodine atom, and the fluorine atom is particularly preferable.

R is preferably a hydrogen atom, an alkyl group having 1 to 5 carbon atoms, or a fluorinated alkyl group having 1 to 5 carbon atoms, and in terms of industrial availability, a hydrogen atom or a methyl group is most preferable.

In the formula (a1-1), the divalent hydrocarbon group which may have an ether bond for $Va^1$ is the same as the divalent hydrocarbon group which may have an ether bond as the substituent for $Va^0$, in the formula (a0-1).

In the formula (a1-2), the ($n_{a2}$+1) valent hydrocarbon group for $Wa^1$ may be an aliphatic hydrocarbon group, or may be an aromatic hydrocarbon group. The aliphatic hydrocarbon group means a hydrocarbon group having no aromaticity, and may be saturated or unsaturated, and in general, it is preferably saturated. Examples of the aliphatic hydrocarbon group include a linear or branched aliphatic hydrocarbon group, an aliphatic hydrocarbon group containing a ring in the structure, and a group in which a linear or branched aliphatic hydrocarbon group and the aliphatic hydrocarbon group containing the ring in the structure are combined with each other.

The "($n_{a2}$+1) valent" is preferably to be divalent to tetravalent, and is further preferably to be divalent or trivalent.

Specific examples of the structural unit represented by the formula (a1-1) are shown below. In the following formulae, $R^\alpha$ represents a hydrogen atom, a methyl group, or a trifluoromethyl group.

[Chemical formula 15]

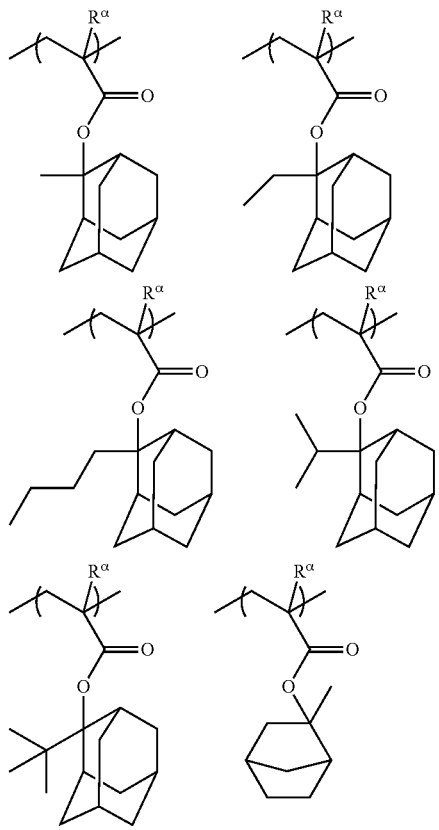

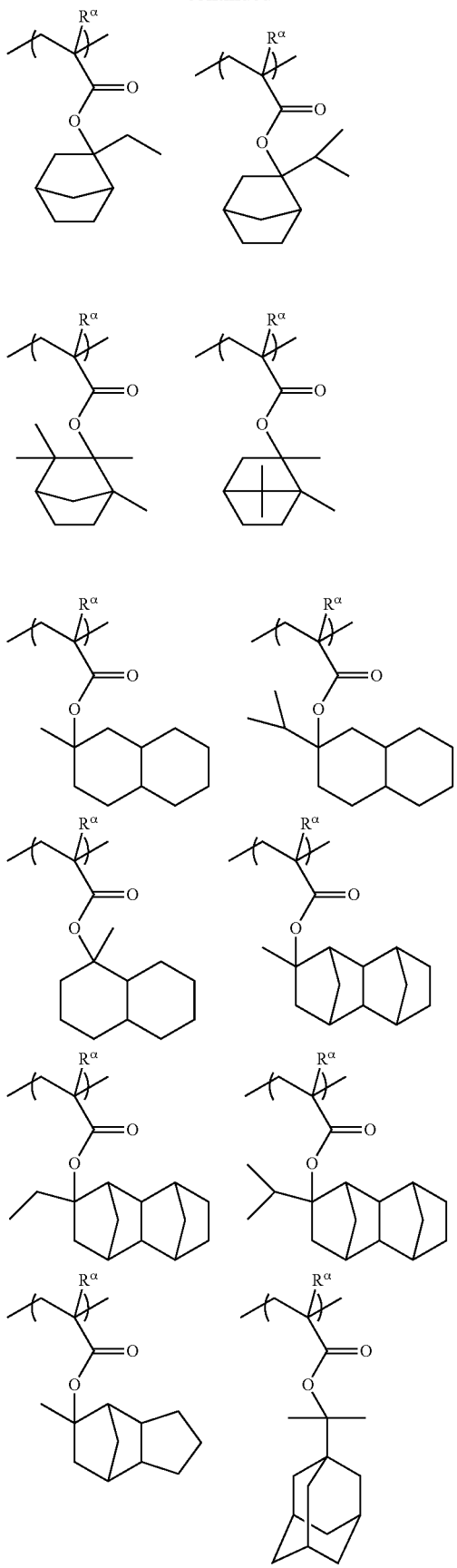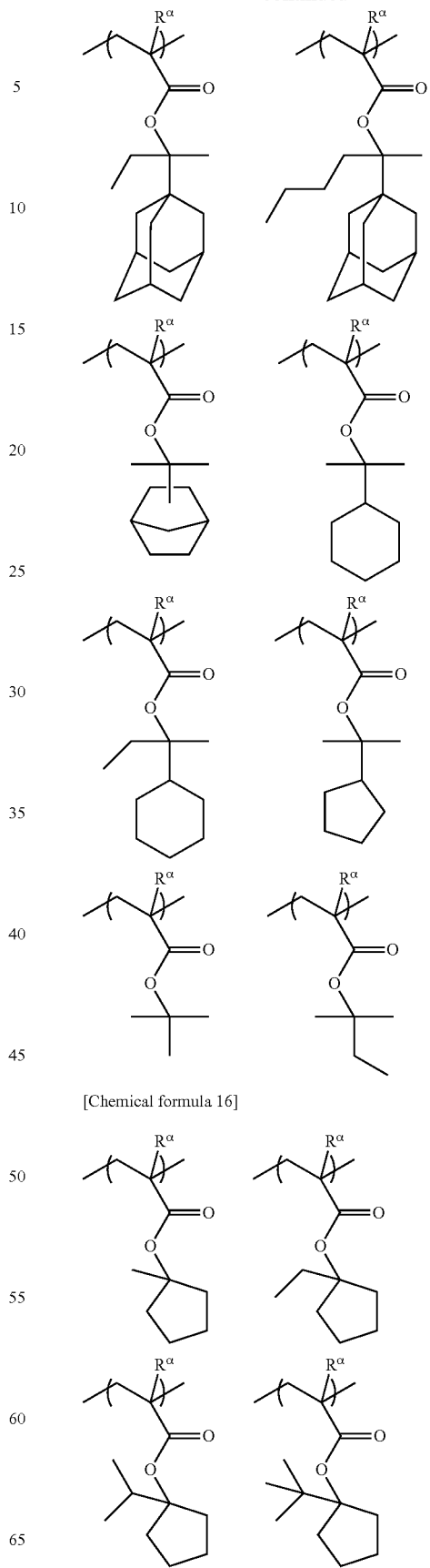

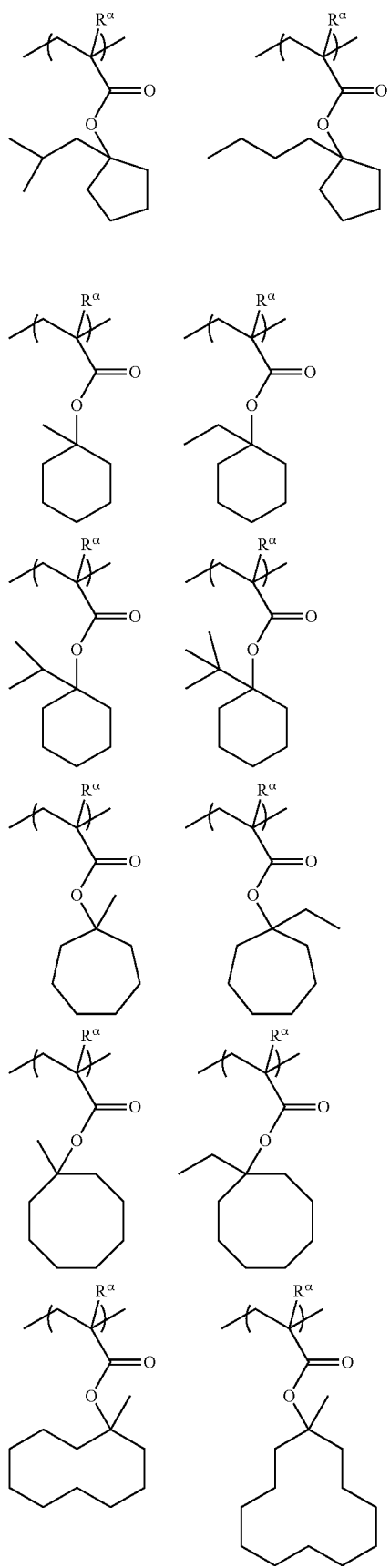
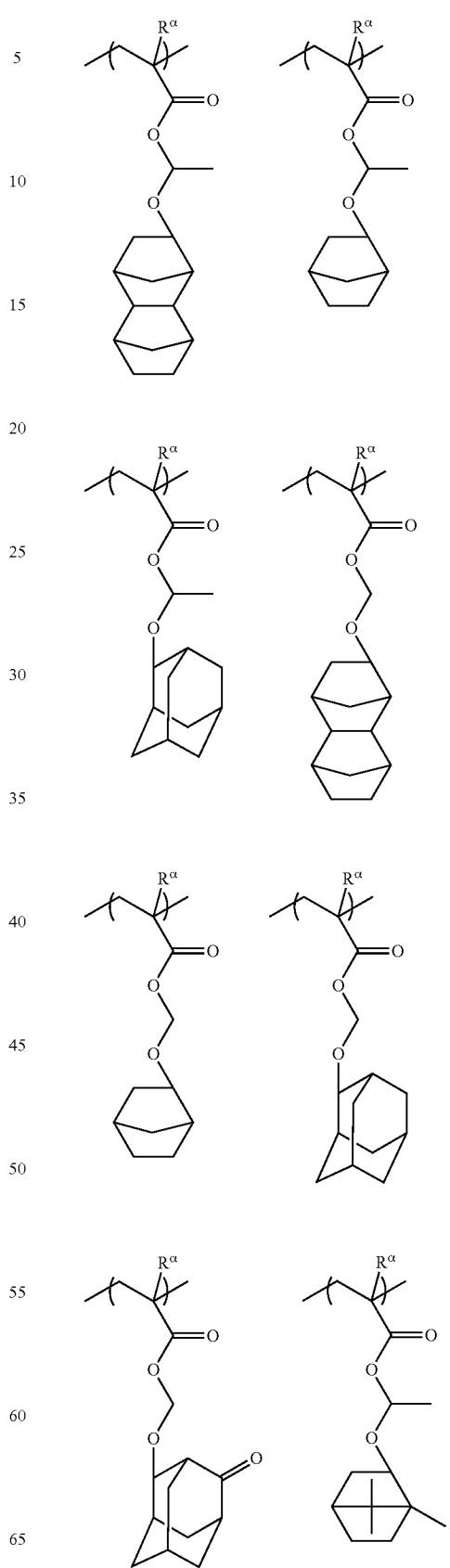
[Chemical formula 17]

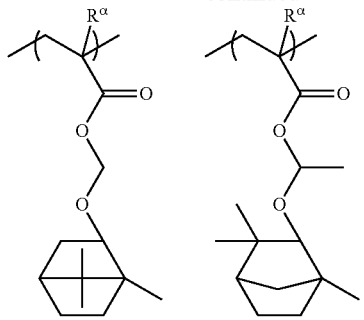
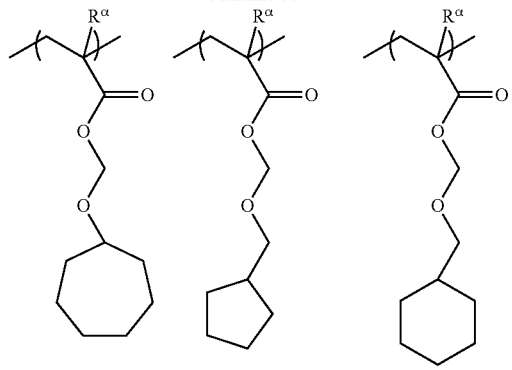
[Chemical formula 18]
[Chemical formula 19]

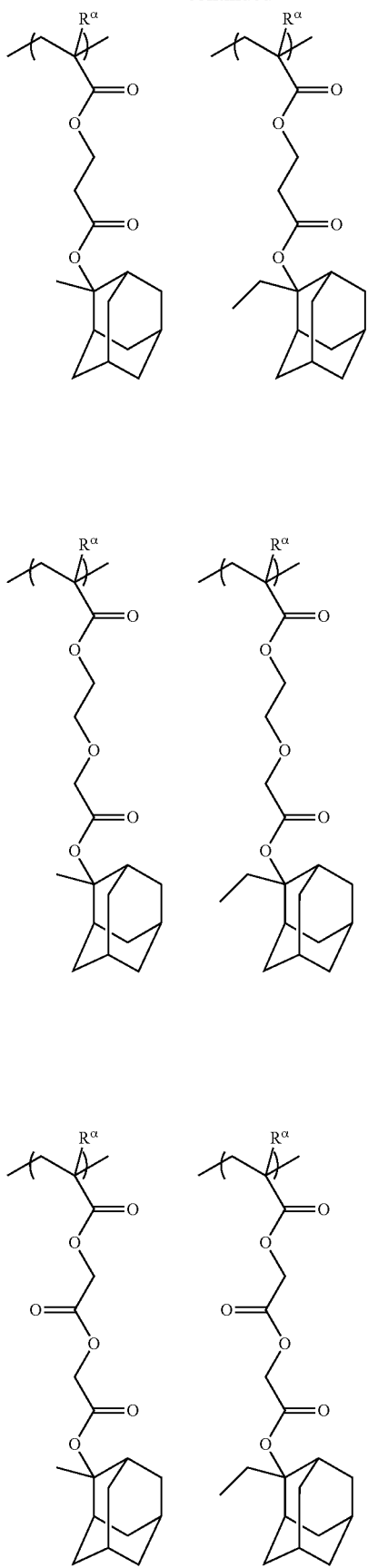
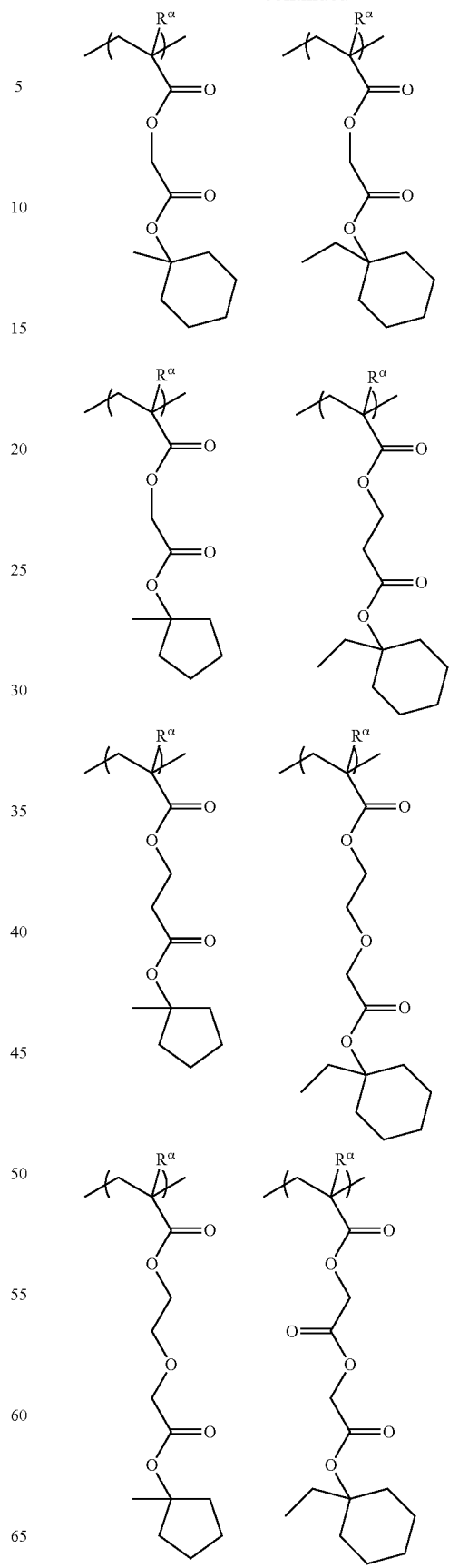

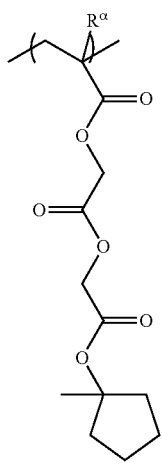

Specific examples of the structural unit represented by the formula (a1-2) are shown below.

[Chemical formula 20]

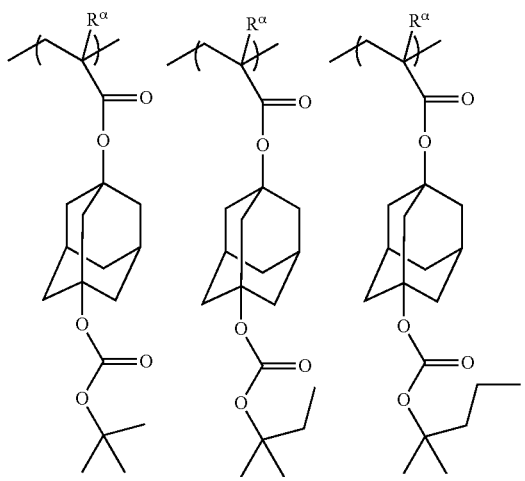

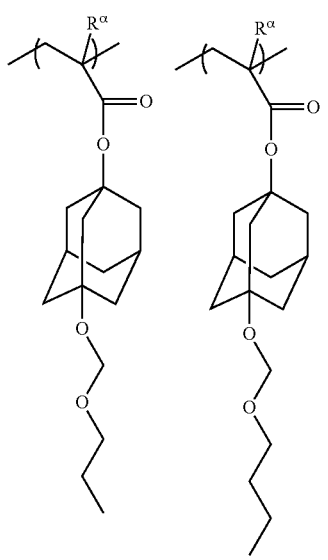

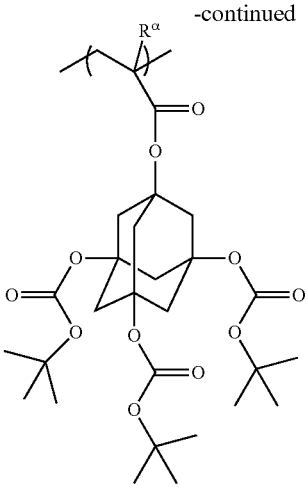

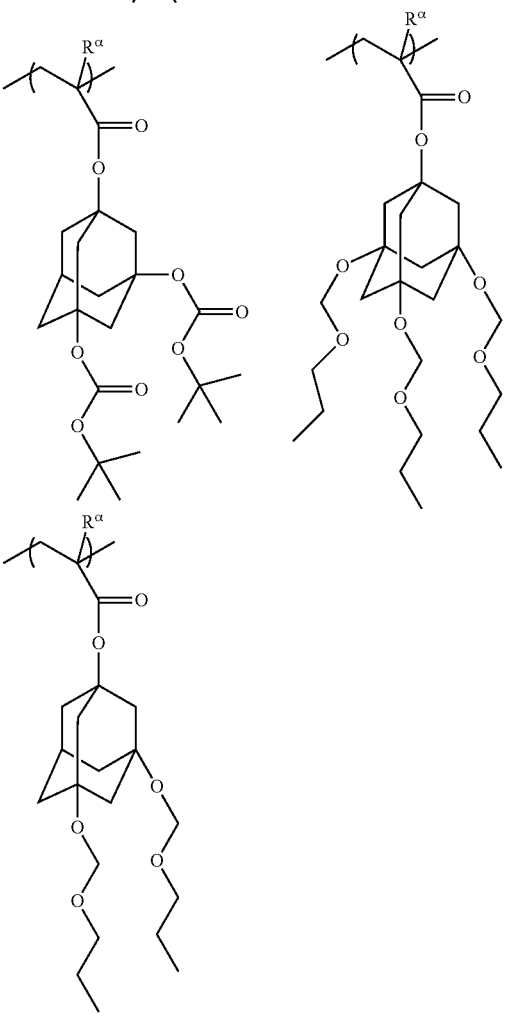

The structural unit (a1) in the (A1) component may be used alone and two or more types thereof may be used in combination.

In a case where the (A1) component contains a structural unit (a1), the ratio of the structural unit (a1) in the (A1) component is preferably 1 to 50 mol %, further preferably 5 to 45 mol %, and still further preferably 5 to 40 mol %, with respect to the total of the entire structural units which constitute the (A1) component.

When the ratio of the structural unit (a1) is set to be equal to or greater than the lower limit, it is possible to easily obtain a resist pattern, and furthermore, lithography properties such as sensitivity, resolution, roughness improvement and an EL margin are improved. In addition, when the ratio of the structural unit (a1) is set to be equal to or less than the upper limit, it is possible to make good balance with other structural units.

Structural Unit (a2):

In the resist composition of the present aspect, the (A1) component preferably further has a structural unit (a2) containing a lactone-containing cyclic group, a —SO$_2$— containing cyclic group or a carbonate-containing cyclic group, provided that the structural unit (a2) is one other than a structural unit corresponding to the structural unit (a0) or the structural unit (a1) is excluded, in addition to the structural unit (a0) and the structural unit (a1).

In a case where the (A1) component is used for forming a resist film, the lactone-containing cyclic group, the —SO$_2$— containing cyclic group, or the carbonate-containing cyclic group of the structural unit (a2) is effective in improving the adhesiveness with respect to the substrate of the resist film. In addition, when the (A1) component has the structural unit (a2), the solubility of the resist film with respect to alkali developing solution is increased at the time of developing in the alkali developing process.

The "lactone-containing cyclic group" means a cyclic group containing a ring (lactone ring) including —O—C(=O)— in the cyclic skeleton. When the lactone ring is counted as the first ring, if there is only the lactone ring, the cyclic group is referred to as a monocyclic group, and if there are other ring structures in addition to the lactone ring, the cyclic group is referred to as a polycyclic group regardless of its structure. The lactone-containing cyclic group may be a monocyclic group, or may be a polycyclic group.

The lactone-containing cyclic group in the structural unit (a2) is not particularly limited, and any lactone-containing cyclic group can be used. Specific examples thereof include groups represented by the following general formulae (a2-r-1), and (a2-r-3) to (a2-r-7).

[Chemical formula 21]

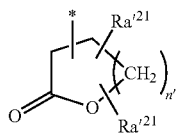

(a2-r-1)

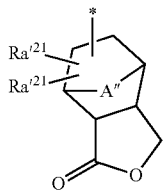

(a2-r-3)

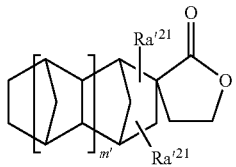

(a2-r-4)

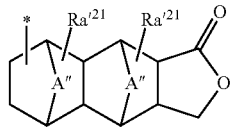

(a2-r-5)

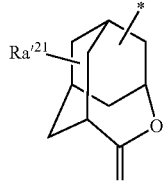

(a2-r-6)

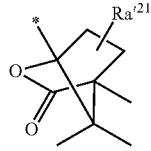

(a2-r-7)

[In the formulae, Ra$'^{21}$'s each independently represent a hydrogen atom, an alkyl group, an alkoxy group, a halogen atom, a halogenated alkyl group, a hydroxyl group, —COOR", —OC(=O)R", a hydroxyalkyl group, or a cyano group; R" is a hydrogen atom, an alkyl group, a lactone-containing cyclic group, a carbonate-containing cyclic group, or a —SO$_2$-containing cyclic group; A" is an alkylene group having 1 to 5 carbon atoms, which may have an oxygen atom (—O—) or a sulfur atom (—S—), an oxygen atom, or a sulfur atom; n' is an integer of 0 to 2; and m' is an integer of 0 or 1.]

In the general formulae (a2-r-1), and (a2-r-3) to (a2-r-7), the alkyl group for Ra$'^{21}$ is preferably an alkyl group having 1 to 6 carbon atoms. The alkyl group is preferably a linear or branched alkyl group. Specifically, examples thereof include a methyl group, an ethyl group, a propyl group, an isopropyl group, an n-butyl group, an isobutyl group, a tert-butyl group, a pentyl group, an isopentyl group, a neopentyl group, and a hexyl group. Among them, the methyl group or the ethyl group are preferable, and the methyl group is particularly preferable.

The alkoxy group for Ra$'^{21}$ is preferably an alkoxy group having 1 to 6 carbon atoms.

The alkoxy group is preferably a linear or branched alkoxy group. specifically, examples thereof include a group in which the alkyl group such as those exemplified as the alkyl group for Ra$'^{21}$ and an oxygen atom (—O—) are linked with each other.

Examples of the halogen atom for Ra$'^{21}$ include a fluorine atom, a chlorine atom, a bromine atom, and an iodine atom, and among them, the fluorine atom is preferable.

Examples of the halogenated alkyl group for Ra$'^{21}$ include a group obtained by substituting at least one or all of the hydrogen atoms of the alkyl group for Ra$'^{21}$ with a halogen atom. The halogenated alkyl group is preferably a fluorinated alkyl group, and is particularly preferably a perfluoroalkyl group.

In —COOR" and —OC(=O)R" for Ra$'^{21}$, R'"s are a hydrogen atom, an alkyl group, a lactone-containing cyclic group, carbonate-containing cyclic group, or a —SO$_2$— containing cyclic group.

The alkyl group for R" may be a linear, branched, or cyclic alkyl group, and the number of carbon atoms thereof is preferably 1 to 15.

In a case where R″ is a linear or branched alkyl group, the number of carbon atoms is preferably 1 to 10, and further preferably 1 to 5. Particularly, a methyl group or an ethyl group is preferable.

In a case where R″ is a cyclic alkyl group, the number of carbon atoms is preferably 3 to 15, further preferably 4 to 12, and most preferably 5 to 10. Specifically, examples of the cyclic alkyl group include a group obtained by removing one or more hydrogen atoms from monocycloalkane which may be or may be not substituted with a fluorine atom or a fluorinated alkyl group; and a group obtained by removing one or more hydrogen atoms from polycycloalkane such as bicycloalkane, tricycloalkane, and tetracycloalkane. More specifically, examples of the cyclic alkyl group include a group obtained by removing one or more hydrogen atoms from monocycloalkane such as cyclopentane and cyclohexane; and a group obtained by removing one or more hydrogen atoms from polycycloalkane such as adamantane, norbornane, isobornane, tricyclodecane, and tetracyclododecane.

Examples of the lactone-containing cyclic group for R″ include the groups represented by the general formulae (a2-r-1), and (a2-r-3) to (a2-r-7).

The carbonate-containing cyclic group for R″ is the same as a carbonate-containing cyclic group described below, and specific examples thereof include the groups represented by general formulae (ax3-r-1) to (ax3-r-3).

The —SO$_2$— containing cyclic group for R″ is the same as a —SO$_2$— containing cyclic group described below, and specific examples thereof include the groups represented by general formulae (a5-r-1) to (a5-r-4).

The hydroxyalkyl group for Ra′$^{21}$ is preferably a hydroxyalkyl group having 1 to 6 carbon atoms, and specific examples thereof include a group obtained by substituting at least one hydrogen atom of the alkyl group for Ra′$^{21}$ with a hydroxyl group.

In the general formulae (a2-r-3) and (a2-r-5), the alkylene group having 1 to 5 carbon atoms for A″ is preferably a linear or branched alkylene group, and examples thereof include a methylene group, an ethylene group, an n-propylene group, and an isopropylene group. In a case where the alkylene group contains an oxygen atom or a sulfur atom, specific examples thereof include a group in which —O— or —S— is present at a terminal of the alkylene group or between carbon atoms, and examples of the aforementioned group include —O—CH$_2$—, —CH$_2$—O—CH$_2$—, —S—CH$_2$—, and —CH$_2$—S—CH$_2$—. A″ is preferably an alkylene group having 1 to 5 carbon atoms or —O—, further preferably an alkylene group having 1 to 5 carbon atoms, and most preferably a methylene group.

Specific examples of the groups represented by the following general formulae (a2-r-1), and (a2-r-3) to (a2-r-7) are shown below.

[Chemical formula 22]

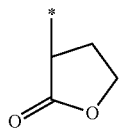

(r-lc-1-1)

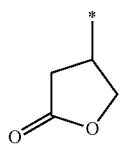

(r-lc-1-2)

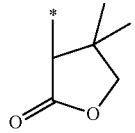

(r-lc-1-3)

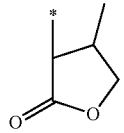

(r-lc-1-4)

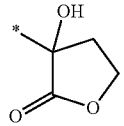

(r-lc-1-5)

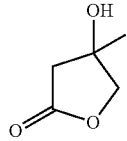

(r-lc-1-6)

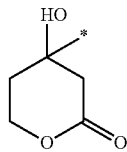

(r-lc-1-7)

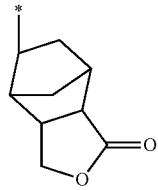

(r-lc-3-1)

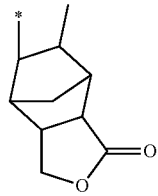

(r-lc-3-2)

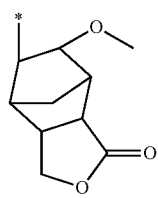

(r-lc-3-3)

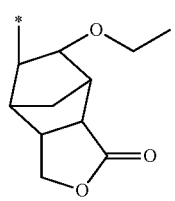

(r-lc-3-4)

(r-lc-3-5)

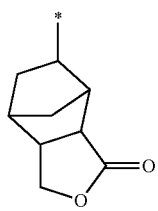

[Chemical formula 23]

(r-lc-4-1)

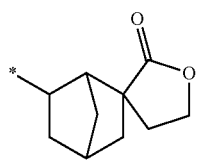

(r-lc-4-2)

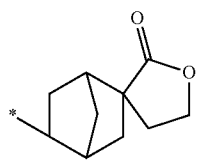

(r-lc-4-3)

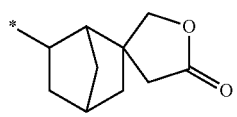

(r-lc-4-4)

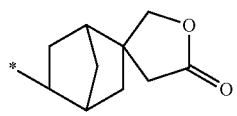

(r-lc-4-5)

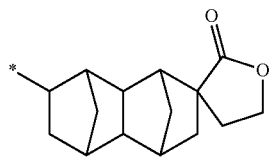

(r-lc-4-6)

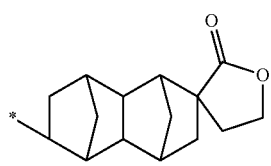

(r-lc-4-7)

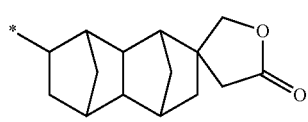

(r-lc-4-8)

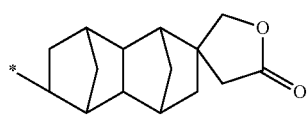

(r-lc-4-9)

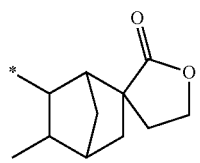

(r-lc-5-1)

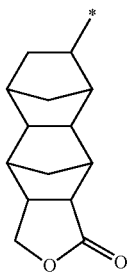

(r-lc-5-2)

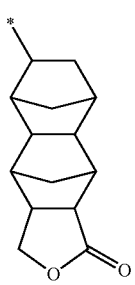

(r-lc-5-3)

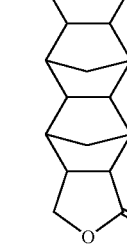

(r-lc-5-4)

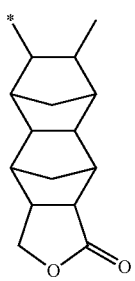

(r-lc-6-1)

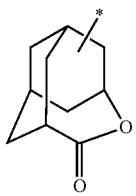

(r-lc-7-1)

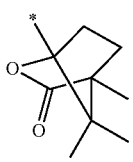

The "—SO$_2$— containing cyclic group" means a cyclic group which contains a ring having —SO$_2$— in the cyclic skeleton, and specifically, is a cyclic group in which the sulfur atom (S) in —SO$_2$— forms a portion of the cyclic skeleton of the cyclic group. When the ring containing —SO$_2$— in the cyclic skeleton is counted as the first ring, if there is only the aforementioned ring, the cyclic group is referred to as a monocyclic group, and if there are other ring structures in addition to the ring, the cyclic group is referred to as a polycyclic group regardless of its structure. The —SO$_2$— containing cyclic group may be a monocyclic group or may be a polycyclic group.

The —SO$_2$— containing cyclic group is particularly preferably a cyclic group containing —O—SO$_2$— in the cyclic skeleton, that is, a cyclic group containing a sultone ring in which —O—S— in —O—SO$_2$— forms a portion of the cyclic skeleton.

More specifically, examples of the —SO$_2$— containing cyclic group include those represented by the following general formulae (a5-r-1) to (a5-r-4).

[Chemical formula 24]

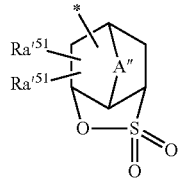

(a5-r-1)

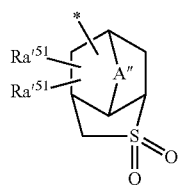

(a5-r-2)

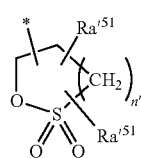

(a5-r-3)

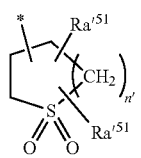

(a5-r-4)

[In the formulae, Ra'$^{51}$'s each independently represent a hydrogen atom, an alkyl group, an alkoxy group, a halogen atom, a halogenated alkyl group, a hydroxyl group, —COOR", —OC(=O)R", a hydroxyalkyl group, or a cyano group; R" is a hydrogen atom, an alkyl group, a lactone-containing cyclic group, a carbonate-containing cyclic group, or a —SO$_2$-containing cyclic group; A" is an alkylene group having 1 to 5 carbon atoms, which may have an oxygen atom or a sulfur atom, an oxygen atom, or a sulfur atom; and n' is an integer of 0 to 2.]

In the general formulae (a5-r-1) to (a5-r-4), A" is the same as A" in the general formulae (a2-r-3) and (a2-r-5).

An alkyl group, an alkoxy group, a halogen atom, a halogenated alkyl group, —COOR", —OC(=O)R", and a hydroxyalkyl group for Ra'$^{51}$ are the same as those exemplified in the description for Ra'$^{21}$ in the general formulae (a2-r-1), and (a2-r-3) to (a2-r-7).

Specific examples of the groups represented by the following general formulae (a5-r-1) to (a5-r-4) are shown below. "Ac" in the formulae represents an acetyl group.

[Chemical formula 25]

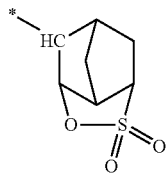

(r-sl-1-1)

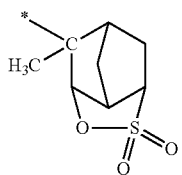

(r-sl-1-2)

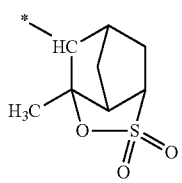

(r-sl-1-3)

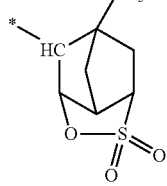

(r-sl-1-4)

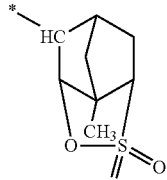

(r-sl-1-5)

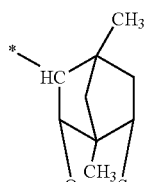

(r-sl-1-6)

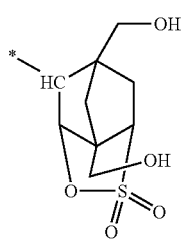

(r-sl-1-7)

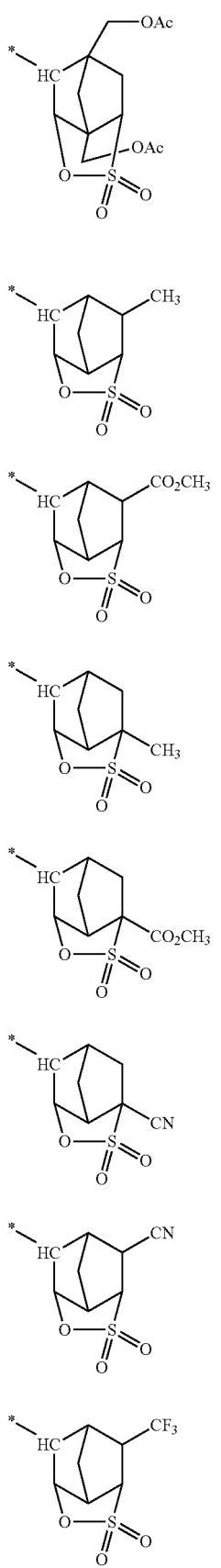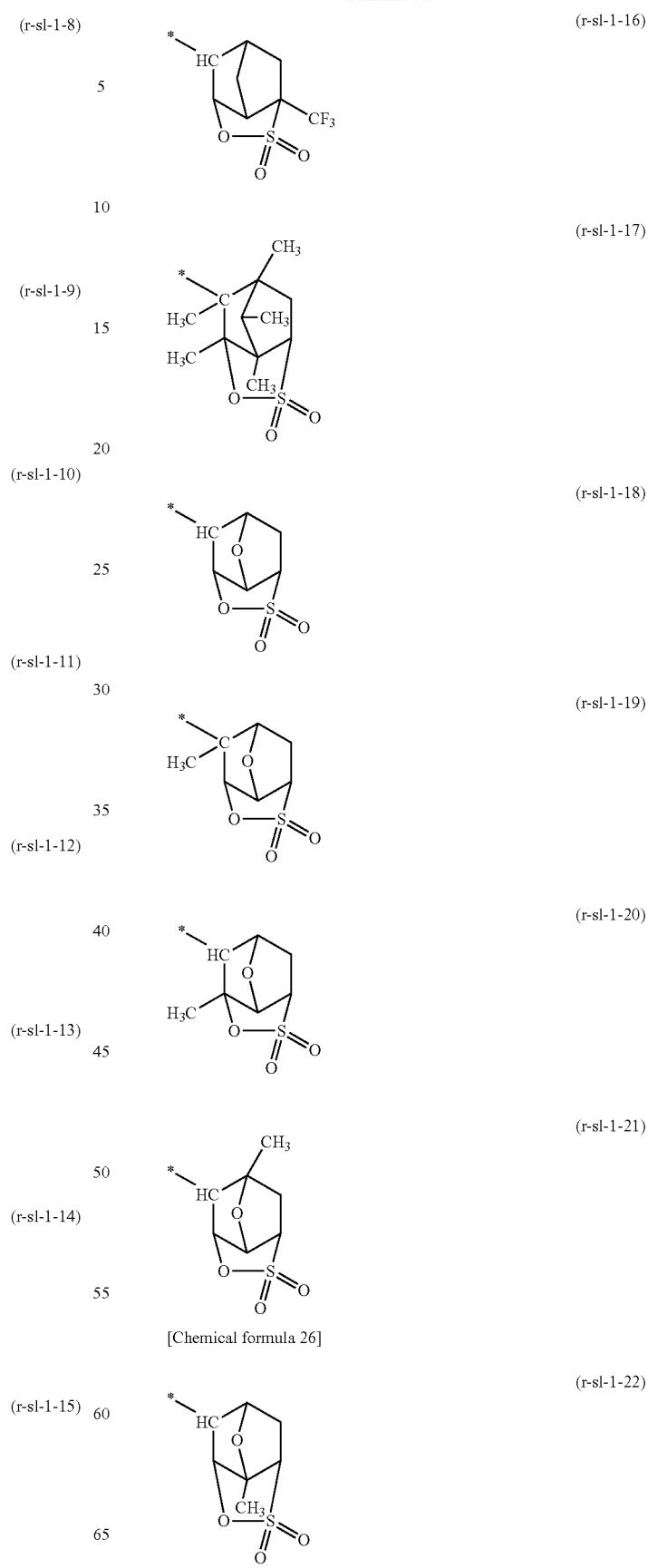
[Chemical formula 26]

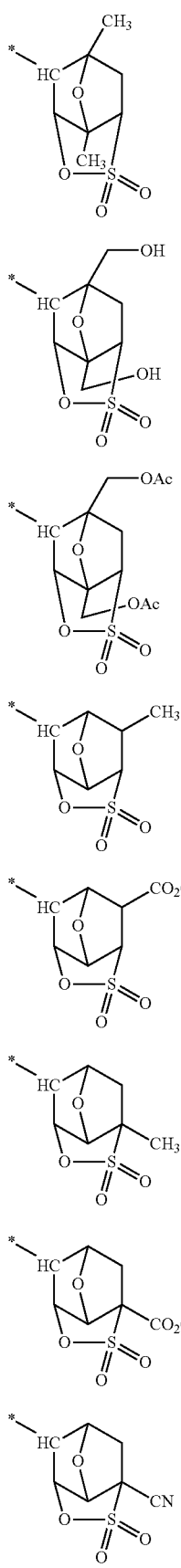
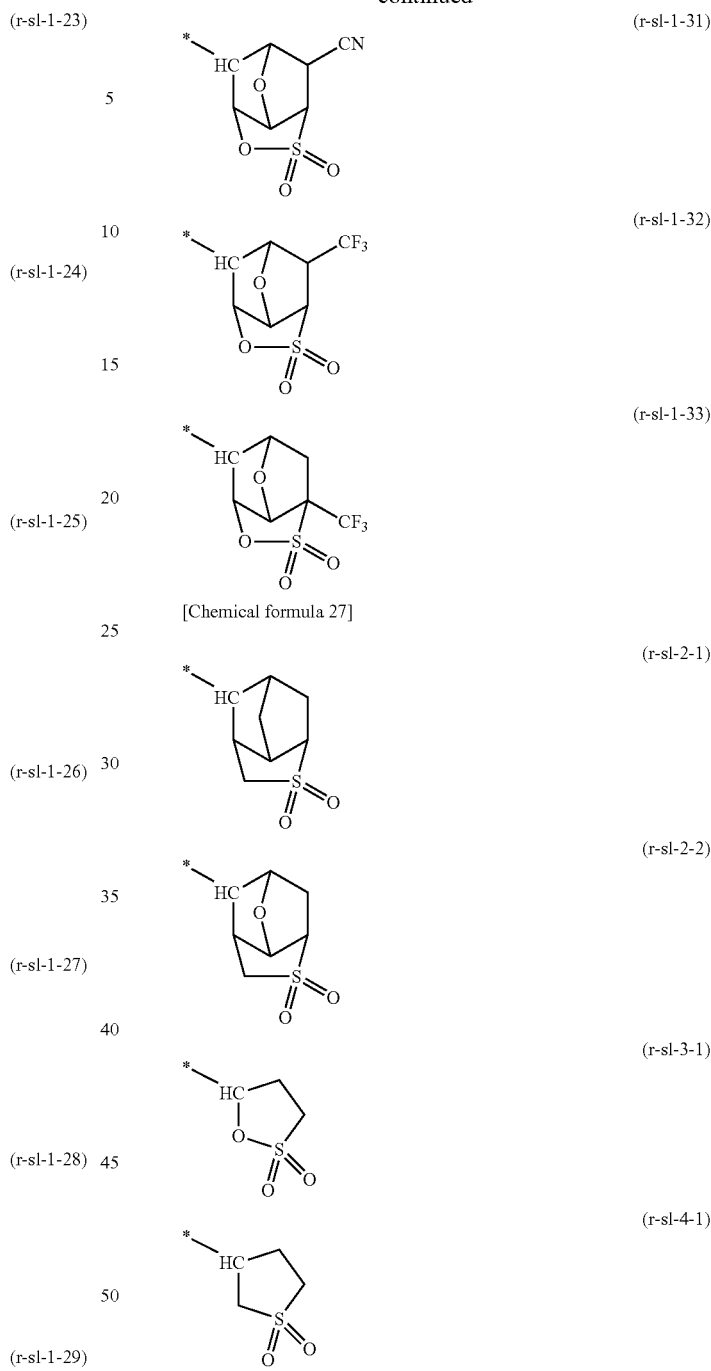

The "carbonate-containing cyclic group" means a cyclic group containing a ring (carbonate ring) including —O—C(=O)—O— in the cyclic skeleton. When the carbonate ring is counted as the first ring, if there is only the carbonate ring, the cyclic group is referred to as a monocyclic group, and if there are other ring structures in addition to the carbonate ring, the cyclic group is referred to as a polycyclic group regardless of its structure. The carbonate-containing cyclic group may be a monocyclic group, or may be a polycyclic group.

The carbonate ring-containing cyclic group is not particularly limited, and any carbonate ring-containing cyclic group can be used. Specific examples thereof include the groups represented by the following general formulae (ax3-r-1) to (ax3-r-3).

[Chemical formula 28]

(ax3-r-1)

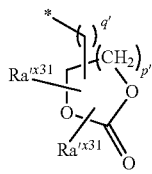

(ax3-r-2)

(ax3-r-3)

[In the formula, Ra'$^{x31}$'s each independently represent a hydrogen atom, an alkyl group, an alkoxy group, a halogen atom, a halogenated alkyl group, a hydroxyl group, —COOR", —OC(=O)R", a hydroxyalkyl group, or a cyano group; R" is a hydrogen atom, an alkyl group, a lactone-containing cyclic group, a carbonate-containing cyclic group, or a —SO$_2$-containing cyclic group; A" is an alkylene group having 1 to 5 carbon atoms, which may have an oxygen atom or a sulfur atom, an oxygen atom, or a sulfur atom; p' is an integer of 0 to 3; and q' is 0 or 1.]

In the general formulae (ax3-r-1) to (ax3-r-3), A" is the same as A" in the general formulae (a2-r-3) and (a2-r-5).

An alkyl group, an alkoxy group, a halogen atom, a halogenated alkyl group, —COOR", —OC(=O)R", and a hydroxyalkyl group for Ra'$^{x31}$ are the same as those exemplified in the description for Ra'$^{21}$ in the general formulae (a2-r-1), and (a2-r-3) to (a2-r-7), respectively.

Specific examples of the groups represented by the following general formulae (ax3-r-1) to (ax3-r-3) are shown below.

[Chemical formula 29]

(r-cr-1-1)

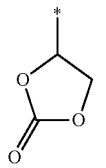

(r-cr-1-2)

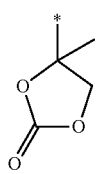

(r-cr-1-3)

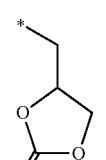

(r-cr-1-4)

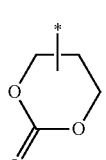

(r-cr-1-5)

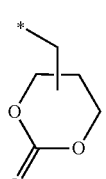

(r-cr-1-6)

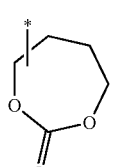

(r-cr-1-7)

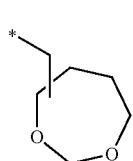

(r-cr-2-1)

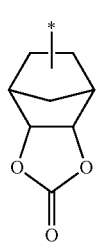

(r-cr-2-2)
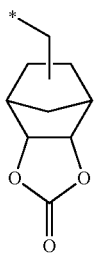

(r-cr-2-3)
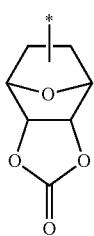

(r-cr-2-4)
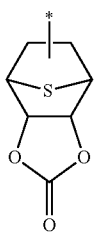

(r-cr-3-1)
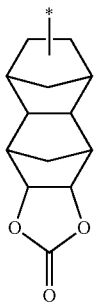

(r-cr-3-2)
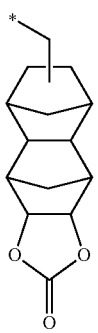

(r-cr-3-3)

(r-cr-3-4)
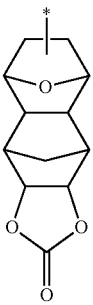

(r-cr-3-5)

Among the structural units (a2), it is preferably a structural unit derived from an acrylic ester which may be obtained by substituting a hydrogen atom bonded to an α-position carbon atom with a substituent.

The structural unit (a2) is preferably a structural unit represented by the following general formula (a2-1).

[Chemical formula 30]

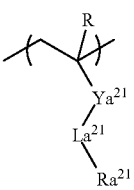
(a2-1)

[In the formula, R is a hydrogen atom, an alkyl group having 1 to 5 carbon atoms, or a halogenated alkyl group having 1 to 5 carbon atoms. $Ya^{21}$ is a single bond or a divalent linking group. $La^{21}$ is —O—, —COO—, —CON (R')—, —OCO—, —CONHCO—, or —CONHCS—, and R' represents a hydrogen atom or a methyl group. Here, in a case where $La^{21}$ is —O—, $Ya^{21}$ is not —CO—. $Ra^{21}$ is a lactone-containing cyclic group, a carbonate-containing cyclic group, or a —$SO_2$— containing cyclic group.]

In the formula (a2-1), R is the same as described above.

The divalent linking group for $Ya^{21}$ is not particularly limited, and preferred examples thereof include a divalent hydrocarbon group which may have a substituent and a divalent linking group containing a heteroatom.

Divalent Hydrocarbon Group which May have a Substituent:

In a case where $Ya^{21}$ is a divalent hydrocarbon group which may have a substituent, the hydrocarbon group may be an aliphatic hydrocarbon group or an aromatic hydrocarbon group.

Aliphatic Hydrocarbon Group for $Ya^{21}$

The aliphatic hydrocarbon group means a hydrocarbon group having no aromaticity. The aliphatic hydrocarbon group may be saturated or unsaturated, and is preferably saturated in general.

Examples of the aliphatic hydrocarbon group include a linear or branched aliphatic hydrocarbon group, or an aliphatic hydrocarbon group containing a ring in the structure.

Linear or Branched Aliphatic Hydrocarbon Group

A linear or branched aliphatic hydrocarbon group preferably has 1 to 10 carbon atoms, more preferably 1 to 6 carbon atoms, further preferably has 1 to 4 carbon atoms, and most preferably has 1 to 3 carbon atoms.

As a linear aliphatic hydrocarbon group, a linear alkylene group is preferable, and specific examples include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

As a branched aliphatic hydrocarbon group, a branched alkylene group is preferable, and specific examples thereof include an alkyl alkylene group such as an alkyl methylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an alkyl ethylene group such as —$CH(CH_3)CH_2$—, —$CH(CH_3)CH(CH_3)$—, —$C(CH_3)_2CH_2$—, —$CH(CH_2CH_3)CH_2$—, —$C(CH_2CH_3)_2$—$CH_2$—; an alkyl trimethylene group such as —$CH(CH_3)CH_2CH_2$— and —$CH_2CH(CH_3)CH_2$—; and an alkyl tetramethylene group such as —$CH(CH_3)CH_2CH_2CH_2$— and —$CH_2CH(CH_3)CH_2CH_2$—. As an alkyl group in an alkyl alkylene group, a linear alkyl group having 1 to 5 carbon atoms is preferable.

The linear or branched aliphatic hydrocarbon group may or may not have a substituent. Examples of the substituent include a florin atom, a fluorinated alkyl group having 1 to 5 carbon atoms which is substituted with a fluorine atom, and a carbonyl group.

Aliphatic Hydrocarbon Group Containing Ring in Structure

Examples of the aliphatic hydrocarbon group containing a ring in the structure include a cyclic aliphatic hydrocarbon group (a group obtained by removing two hydrogen atoms from an aliphatic hydrocarbon ring) which may contain a substituent containing a heteroatom in the ring structure, a group in which the cyclic aliphatic hydrocarbon group is bonded to a terminal of the linear or branched aliphatic hydrocarbon group, and a group in which the cyclic aliphatic hydrocarbon group is present in the middle of the linear or branched aliphatic hydrocarbon group. Examples of the linear or branched cyclic aliphatic hydrocarbon group include the same groups as described above.

The number of carbon atoms of the cyclic aliphatic hydrocarbon group is preferably 3 to 20, and further preferably 3 to 12.

The cyclic aliphatic hydrocarbon group may be a polycyclic group or a monocyclic group. As the monocyclic alicyclic hydrocarbon group, a group obtained by removing two hydrogen atoms from a monocycloalkane is preferable. The number of carbon atoms of the monocycloalkane is preferably 3 to 6. Specifically, examples thereof include cyclopentane and cyclohexane. As the polycyclic alicyclic hydrocarbon group, a group obtained by removing two hydrogen atoms from polycycloalkane is preferable, and the number of carbon atoms of polycycloalkane is preferably 7 to 12. Specifically, examples thereof include adamantane, norbornane, isobornane, tricyclodecane, and tetracyclododecane.

The cyclic aliphatic hydrocarbon group may or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and is most preferably a methyl group, an ethyl group, a propyl group, an n-butyl group, and a tert-butyl group.

The alkoxy group as the substituent is preferably an alkoxy group having 1 to 5 carbon atoms, is further preferably a methoxy group, an ethoxy group, an n-propoxy group, an iso-propoxy group, an n-butoxy group, and a tert-butoxy group, and is most preferably a methoxy group, and an ethoxy group.

Examples of the halogen atom as the substituent include a fluorine atom, a chlorine atom, a bromine atom, and an iodine atom, and the fluorine atom is preferable.

Examples of the halogenated alkyl group as the substituent include a group obtained by substituting at least one or all of the hydrogen atoms of an alkyl group with a halogen atom.

In the cyclic aliphatic hydrocarbon group, a portion of the carbon atoms for constituting the ring structure thereof may be substituted with a substituent containing a heteroatom. The substituent containing the heteroatom is preferably —O—, —C(=O)—O—, —S—, —S(=O)$_2$—, and —S(=O)$_2$—O—.

Aromatic Hydrocarbon Group for $Ya^{21}$

The aromatic hydrocarbon group is a hydrocarbon group having at least one aromatic ring.

The aromatic ring is not particularly limited as long as it is a cyclic conjugated system having (4n+2) π-electrons, and it may be monocyclic or polycyclic. The number of the carbon atoms of the aromatic ring is preferably 5 to 30, further preferably 5 to 20, still further preferably 6 to 15, and particularly preferably 6 to 12. In this regard, the number of the carbon atoms does not include the number of the carbon atoms in the substituent. Specific examples of the aromatic ring include an aromatic hydrocarbon ring such as benzene, naphthalene, anthracene, and phenanthrene; and aromatic heterocycle in which a portion of the carbon atoms which constitute the aromatic hydrocarbon ring is substituted with a heteroatom. Examples of the heteroatom in the aromatic heterocycle include an oxygen atom, a sulfur atom, and a nitrogen atom.

Specific examples of the aromatic heterocycle include a pyridine ring and a thiophene ring.

Specific examples of the aromatic hydrocarbon group include a group (an arylene group or a heteroarylene group) obtained by removing two hydrogen atoms from the aromatic hydrocarbon ring or the aromatic heterocycle; a group obtained by removing two hydrogen atoms from an aromatic compound (for example, biphenyl and fluorene) containing two or more aromatic rings; and a group (for example, a group obtained by further removing one hydrogen atom from the aryl group in the aryl alkyl group such as a benzyl group, a phenethyl group, a 1-naphtyl methyl group, a 2-naphtyl methyl group, a 1-naphtyl ethyl group, and a 2-naphtyl ethyl group) in which one hydrogen atom of the group (an aryl group or a heteroaryl group) obtained by removing one hydrogen atom from the aromatic hydrocarbon ring or the aromatic heterocycle is substituted with an alkylene group. The number of carbon atoms of the alkylene group which is bonded to the aryl group or the heteroaryl group is preferably 1 to 4, further preferably 1 to 2, and particularly preferably 1.

In the aromatic hydrocarbon group, the hydrogen atom contained in the aromatic hydrocarbon group may be substituted with a substituent. For example, a hydrogen atom bonded to the aromatic ring in the aromatic hydrocarbon group may be substituted with a substituent. Examples of the substituent include an alkyl group, an alkoxy group, a halogen atom, a halogenated alkyl group, and a hydroxyl group.

The alkyl group as the substituent is preferably an alkyl group having 1 to 5 carbon atoms, and is most preferably a methyl group, an ethyl group, a propyl group, an n-butyl group, and a tert-butyl group.

Examples of an alkoxy group, a halogen atom, and a halogenated alkyl group as the substituent include those exemplified as the substituent which substitutes a hydrogen atom contained in the cyclic aliphatic hydrocarbon group.

Divalent Linking Group Containing a Heteroatom:

In a case where $Ya^{21}$ is a divalent linking group containing a heteroatom, preferred examples of the divalent linking group containing a heteroatom include —O—, —C(=O)—O—, —C(=O)—, —O—C(=O)—O—, —C(=O)—NH—, —NH—, —NH—C(=NH)— (H may be substituted with a substituent such as an alkyl group and an acyl group), —S—, —S(=O)$_2$—, —S(=O)$_2$—O—, and a group represented by general formulae —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— and —$Y^{21}$—S(=O)$_2$—O—$Y^{22}$— [In the formulae, $Y^{21}$ and $Y^{22}$ each independently represent a divalent hydrocarbon group which may have a substituent, O represents an oxygen atom, and m'' represents an integer of 0 to 3].

In a case where the divalent linking group containing the heteroatom is —C(=O)—NH—, —C(=O)—NH—C(=O)—, —NH—, or —NH—C(=NH)—, H may be substituted with a substituent such as an alkyl group and an acyl group. The substituent (an alkyl group, an acyl group, or the like) preferably has 1 to 10 carbon atoms, further preferably has 1 to 8 carbon atoms, and particularly preferably has 1 to 5 carbon atoms.

In general formulae —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$—, and —$Y^{21}$—S(=O)$_2$—O—$Y^{22}$—, $Y^{21}$ and $Y^{22}$ each independently represent a divalent hydrocarbon group which may have a substituent. Examples of the divalent hydrocarbon group include the same group as that (divalent hydrocarbon group which may have a substituent) exemplified as the divalent linking group.

$Y^{21}$ is preferably a linear aliphatic hydrocarbon group, is further preferably a linear alkylene group, is still further preferably a linear alkylene group having 1 to 5 carbon atoms, and is particularly preferably a methylene group or an ethylene group.

$Y^{22}$ is preferably a linear or branched aliphatic hydrocarbon group, and is further preferably a methylene group, an ethylene group, or an alkyl methylene group. An alkyl group in the alkyl methylene group is preferably a linear alkyl group having 1 to 5 carbon atoms, further preferably a linear alkyl group having 1 to 3 carbon atoms, and most preferably a methyl group.

In the group represented by formula —[$Y^{21}$—C(=O)—O]$_{m''}$—$Y^{22}$—, m'' is an integer of 0 to 3, is preferably an integer of 0 to 2, further preferably 0 or 1, and particularly preferably 1. That is, as a group represented by formula —[$Y^{21}$—C(=O)—O]$_{m''}$—$Y^{22}$—, a group represented by formula —$Y^{21}$—C(=O)—O—$Y^{22}$— is particularly preferable. Among them, a group represented by formula —(CH$_2$)$_{a'}$—C(=O)—O—(CH$_2$)$_{b'}$— is preferable. In the formula, a' is an integer of 1 to 10, preferably an integer of 1 to 8, further preferably an integer of 1 to 5, still further preferably 1 or 2, and most preferably 1. b' is an integer of 1 to 10, preferably an integer of 1 to 8, further preferably an integer of 1 to 5, still further preferably 1 or 2, and most preferably 1.

$Ya^{21}$ is preferably a single bond, an ester bond [—C(=O)—O—], an ether bond (—O—), a linear or branched alkylene group, or a combination thereof.

In the formula (a2-1), $Ra^{21}$ is a lactone-containing cyclic group, a —SO$_2$— containing cyclic group, or a carbonate-containing cyclic group.

Preferred examples of the lactone-containing cyclic group, the —SO$_2$— containing cyclic group, and the carbonate-containing cyclic group in $Ra^{21}$ include groups represented by the general formulae (a2-r-1), and (a2-r-3) to (a2-r-7), groups represented by general formulae (a5-r-1) to (a5-r-4), and groups represented by general formulae (ax3-r-1) to (ax3-r-3).

Among them, the lactone-containing cyclic group or the —SO$_2$— containing cyclic group is preferable, the group represented by the general formula (a2-r-1), (a2-r-6), or (a5-r-1) is further preferable, and the group represented by the general formula (a2-r-6) or (a5-r-1) is particularly preferable.

Specifically, any one of the groups represented by the Chemical formulae (r-lc-1-1) to (r-lc-1-7), (r-lc-6-1), (r-sl-1-1), and (r-sl-1-18) is further preferable.

The structural unit (a2) in the (A1) component may be used alone, or two or more types thereof may be used in combination.

In a case where the (A1) component contains the structural unit (a2), the ratio of the structural unit (a2) is preferably 1 to 80 mol %, further preferably 10 to 70 mol %, still further preferably 10 to 65 mol %, and particularly preferably 10 to 60 mol %, with respect to the total of the entire structural units for constituting the (A1) component.

When the ratio of the structural unit (a2) is set to be equal to or greater than the preferred lower limit, it is possible to obtain sufficient effects by containing the structural unit (a2); on the other hand, when the ratio of the structural unit (a2) is set to be equal to or lower than the preferred upper limit, it is possible to make good balance with other structural units, and thus various lithography properties and the pattern shape are improved.

Structural Unit (a3):

A structural unit (a3) is a structural unit (here, a structural unit corresponding to the structural unit (a0), (a1) or (a2) is excluded) containing a polar group-containing aliphatic hydrocarbon group.

When the (A1) component has a structural unit (a3), the hydrophilicity of the (A) component is enhanced, which contributes to enhancement of the resolution.

Examples of the polar group include a hydroxyl group, a cyano group, a carboxy group, and a hydroxyalkyl group in which at least one hydrogen atom of the alkyl group is substituted with a fluorine atom, and among them, a hydroxyl group is particularly preferable.

Examples of the aliphatic hydrocarbon group include a linear or branched hydrocarbon group (preferably an alkylene group) having 1 to 10 carbon atoms, and a cyclic aliphatic hydrocarbon group (a cyclic group). The cyclic group may be a monocyclic group, or may be a polycyclic group, for example, in a resin for a resist composition for ArF excimer laser, the cyclic group can be appropriately selected from the resins which have been proposed many times. The cyclic group is preferably a polycyclic group, and the number of the carbon atoms is further preferably 7 to 30.

Among them, a structural unit derived from acrylic ester containing an aliphatic polycyclic group and including a hydroxyl group, a cyano group, a carboxy group, or a hydroxyalkyl group in which at least one hydrogen atom of the alkyl group is substituted with a fluorine atom is further preferable. Examples of the polycyclic group include a group obtained by removing two or more hydrogen atoms from bicycloalkane, tricycloalkane, and tetracycloalkane. Specific examples thereof include a group obtained by removing two or more hydrogen atoms from polycycloalkane such as adamantane, norbornane, isobornane, tricyclodecane, and tetracyclododecane. Among the polycyclic groups, a group obtained by removing two or more hydrogen atoms from adamantane, a group obtained by removing two or more hydrogen atoms from norbornane, and a group obtained by removing two or more hydrogen atoms from tetracyclododecane in terms of the industrial availability.

The structural unit (a3) is not particularly limited as long as it contains a polar group-containing aliphatic hydrocarbon group, and any structural unit can be used.

The structural unit (a3) is a structural unit derived from acrylic ester which may be obtained by substituting a hydrogen atom bonded to an α-position carbon atom with a substituent, and a structural unit including a polar group-containing aliphatic hydrocarbon group is preferable.

When the hydrocarbon group in the polar group-containing aliphatic hydrocarbon group is a linear or branched hydrocarbon group having 1 to 10 carbon atoms, the structural unit (a3) is preferably a structural unit derived from hydroxyethyl ester of acrylic acid, and when the hydrocarbon group is a polycyclic group, the structural unit (a3) is preferably a structural unit represented by the following formula (a3-1), a structural unit represented by the following formula (a3-2), and a structural unit represented by the following formula (a3-3).

[Chemical formula 31]

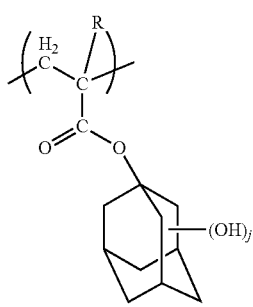 (a3-1)

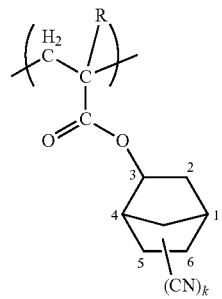 (a3-2)

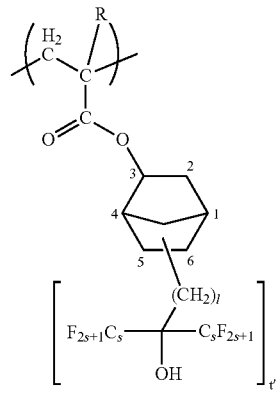 (a3-3)

[In the formula, R is the same as described above, j is an integer of 1 to 3, k is an integer of 1 to 3, t' is an integer of 1 to 3, l is an integer of 1 to 5, and s is an integer of 1 to 3.]

In the formula (a3-1), j is preferably 1 or 2, and is further preferably 1. In a case where j is 2, a hydroxyl group is preferably bonded to 3-position and 5-position of an adamantyl group. In a case where j is 1, a hydroxyl group is preferably bonded to 3-position of an adamantyl group.

j is preferably 1, a hydroxyl group is particularly preferably bonded to 3-position of an adamantyl group.

In the formula (a3-2), k is preferably 1. A cyano group is preferably bonded to 5-position or 6-position of a norbornyl group.

In the formula (a3-3), t' is preferably 1. l is preferably 1. s is preferably 1. These preferably include a structure in which a 2-norbornyl group or a 3-norbornyl group is bonded to a terminal of a carboxy group of an acrylic acid. Fluorinated alkyl alcohol is preferably bonded to 5-position or 6-position of a norbornyl group.

The structural unit (a3) in the (A1) component may be used alone, or two or more types thereof may be used in combination.

In a case where the (A1) component includes a structural unit (a3), the ratio of the structural unit (a3) is preferably 5 to 50 mol %, further preferably 5 to 40 mol %, and still further preferably 5 to 35 mol %, with respect to the total of the entire structural units for constituting the (A1) component.

When the ratio of the structural unit (a3) is set to be equal to or greater than the preferred lower limit, it is possible to obtain sufficient effects by containing the structural unit (a3); on the other hand, when the ratio of the structural unit (a3) is set to be equal to or lower than the preferred upper limit, it is easy to make good balance with other structural units.

Structural Unit (a4):

A structural unit (a4) is a structural unit containing an acid non-dissociable aliphatic cyclic group.

When the (A1) component has a structural unit (a4), the dry etching resistance of the formed resist pattern is improved. In addition, the hydrophobicity of the (A) component is improved. It is considered that the improvement of the hydrophobicity contributes to the improvement of the resolution and the resist pattern shape particularly in the case of the solvent developing process.

The "acid non-dissociable cyclic group" in the structural unit (a4) is a cyclic group in which the acid remains in the structural unit as it is even with the action of the acid when an acid is generated in the resist composition upon exposure (for example, when the acid is generated from the (B) component described below).

The structural unit (a4) is preferably a structural unit derived from acrylic ester containing an acid non-dissociable aliphatic cyclic group. As the cyclic group, conventionally well-known structural units which are used for a resin component of a resist composition for ArF excimer laser or KrF excimer laser (preferably, for ArF excimer laser) can be used.

Particularly, the structural unit (a4) is preferably at least one selected from a tricyclodecyl group, an adamantyl group, a tetracyclododecyl group, an isobornyl group, and a norbornyl group in terms of the industrial availability. These polycyclic groups may have a linear or branched alkyl group having 1 to 5 carbon atoms as a substituent.

Specific examples of the structural unit (a4) include structural units represented by the following general formulae (a4-1) to (a4-7).

[Chemical formula 32]

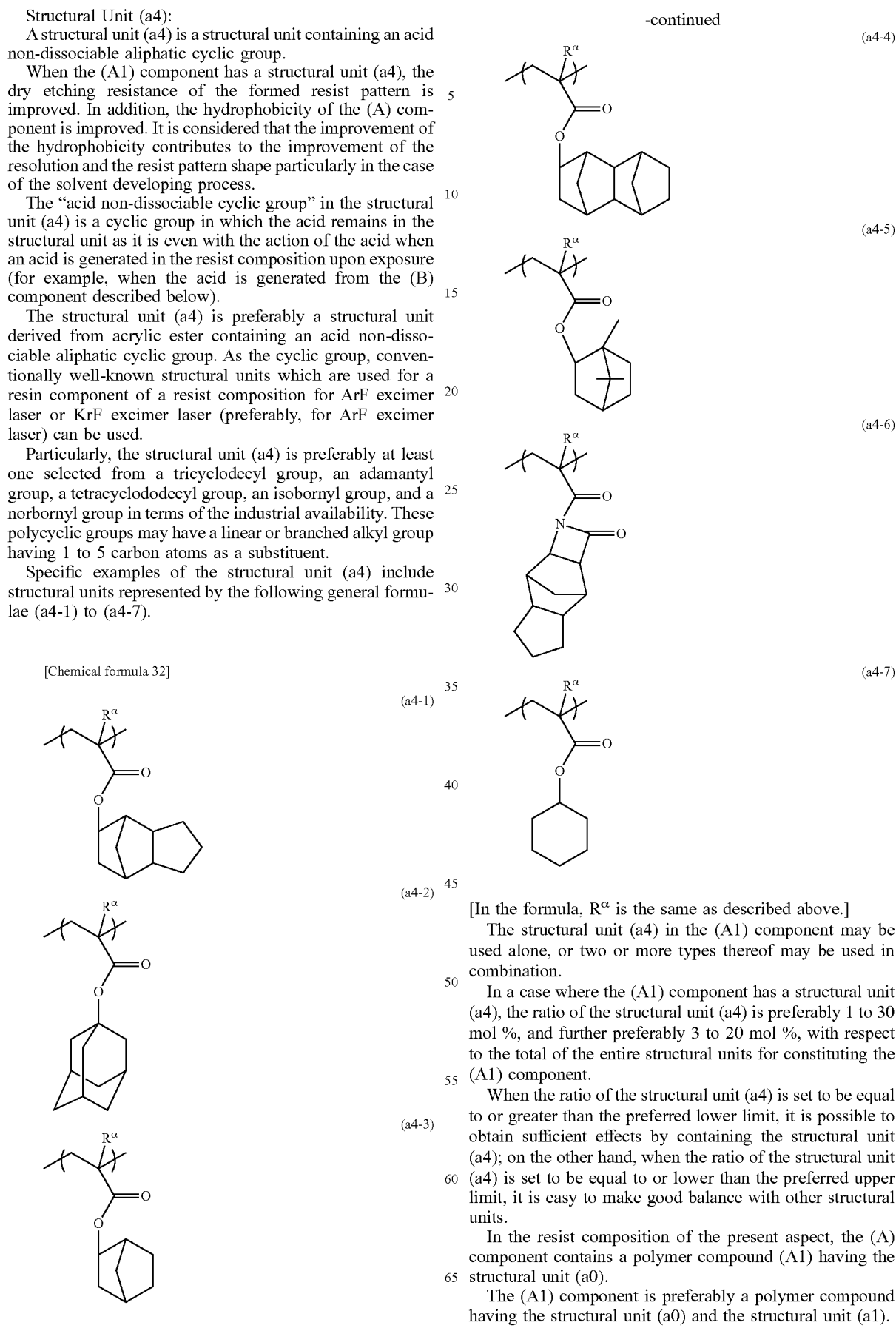

[In the formula, $R^\alpha$ is the same as described above.]

The structural unit (a4) in the (A1) component may be used alone, or two or more types thereof may be used in combination.

In a case where the (A1) component has a structural unit (a4), the ratio of the structural unit (a4) is preferably 1 to 30 mol %, and further preferably 3 to 20 mol %, with respect to the total of the entire structural units for constituting the (A1) component.

When the ratio of the structural unit (a4) is set to be equal to or greater than the preferred lower limit, it is possible to obtain sufficient effects by containing the structural unit (a4); on the other hand, when the ratio of the structural unit (a4) is set to be equal to or lower than the preferred upper limit, it is easy to make good balance with other structural units.

In the resist composition of the present aspect, the (A) component contains a polymer compound (A1) having the structural unit (a0).

The (A1) component is preferably a polymer compound having the structural unit (a0) and the structural unit (a1).

Specific example of the (A1) component include a polymer compound consisting of a repeated structure of the structural unit (a0) and the structural unit (a1); a polymer compound consisting of a repeated structure of the structural unit (a0), the structural unit (a1), and the structural unit (a2); a polymer compound consisting of a repeated structure of the structural unit (a0), the structural unit (a1), and the structural unit (a3); and a polymer compound consisting of a repeated structure of the structural unit (a0), the structural unit (a1), the structural unit (a2), and the structural unit (a3).

The mass average molecular weight (Mw) (in terms of the standard polystyrene by gel permeation chromatography (GPC)) of the (A1) component is not particularly limited, and is preferably about 1,000 to 500,000, and further preferably about 3,000 to 50,000.

When the Mw of the (A1) component is equal to or less than the preferred upper limit, the solubility with respect to a resist solvent is sufficient in a case where the (A1) component is used as a resist, and when the Mw of the (A1) component is equal to or greater than the preferred lower limit, dry etching resistance and a resist pattern cross-sectional shape are improved.

The dispersivity (Mw/Mn) of the (A1) component is not particularly limited, and is preferably about 1.0 to 4.0, further preferably about 1.0 to 3.0, and particularly preferably about 1.5 to 2.5. Note that, Mn represents a number average molecular weight.

The (A1) component may be used alone, or two or more types thereof may be used in combination.

The ratio of the (A1) component in the (A) component is preferably 25% by mass or more, further preferably 50% by mass or more, still further preferably 75% by mass or more, and may be 100% by mass, with respect to the total mass of the (A) component. When the ratio is 25% by mass or more, it is easy to form a resist composition which is highly-sensitized and is excellent in roughness reduction and other lithography properties.

Method for Preparing (A1) Component:

The (A1) component can be prepared by dissolving a monomer for forming each structural unit into a polymerization solvent, and adding a radical polymerization initiator such as azobisisobutyronitrile (AIBN), and dimethyl 2,2'-azobisisobutyrate (for example, V-601) to the solvent so as to perform polymerization.

A—$C(CF_3)_2$—OH group may be introduced to a terminal by using a chain transfer agent such as HS—$CH_2$—$CH_2$—$CH_2$—$C(CF_3)_2$—OH in combination at the time of the polymerization. As such, a copolymer to which a hydroxyalkyl group in which at least one hydrogen atom of the alkyl group is substituted with a fluorine atom is introduced is effective in decreasing development defects and line edge roughness (LER: nonuniform irregularities of the line side walls).

As the polymerization solvent, well-known solvents can be used, and examples thereof include ether (chain ethers such as diethyl ether and glycol ethers, e.g., propylene glycol monomethyl ether; and cyclic ethers such as tetrahydrofuran, and dioxane), esters (methyl acetate, ethyl acetate, butyl acetate, ethyl lactate, and glycol ether esters such as propylene glycol monomethyl ether acetate), ketones (such as acetone, methyl ethyl ketone, methyl isobutyl ketone, and cyclohexanone), amide (such as N,N-dimethylacetamide, and N,N-dimethylformamide), sulfoxide (such as dimethyl sulfoxide), alcohol (such as methanol, ethanol, and propanol), hydrocarbons (aromatic hydrocarbons such as benzene, toluene, and xylene; and aliphatic hydrocarbons such as hexane; and alicyclic hydrocarbons such as cyclohexane) and mixed solvents thereof.

As a polymerization initiator, well-known polymerization initiators can be used.

A polymerization temperature is appropriately selected approximately in a range of about 30° C. to 150° C.

(A2) Component

In the resist composition of the present aspect, a base material component (hereinafter, referred to as "(A2) component") which does not correspond to the (A1) component and of which the solubility in a developing solution changes under the action of an acid may be used also as the (A) component.

The (A2) component is not particularly limited and can be selected from various components known as a base material component for chemically amplified resist composition (for example, abase resin for ArF excimer laser or KrF excimer laser (preferably, for ArF excimer laser)). The (A2) component may be used alone, and two or more types thereof may be used in combination.

In the resist composition of the present aspect, the (A) component may be used alone, or two or more types thereof may be used in combination.

In the resist composition of the present aspect, the content of the (A) component may be adjusted depending on a film thickness of a resist film to be formed.

(D) Component

The (D) component is an acid diffusion control agent component.

The "acid diffusion control agent component" functions as a quencher (acid diffusion control agent) that traps an acid generated in the resist composition upon exposure.

The (D) component to be used in the resist composition of the present aspect includes the compound (D1) (hereinafter, referred to as "the (D1) component) of which a conjugate acid has an acid dissociation constant (pKa) of less than 3.

As the (D) component, at least the (D1) component is used, and an acid diffusion control agent component (hereinafter, referred to as "(D2) component") other than the (D1) component may be used in combination.

(D1) Component

The (D1) component is a compound whose a conjugate acid has an acid dissociation constant (pKa) of less than 3. Since the (D1) component is used in combination with the (A1) component, the exposure stability of the resist composition can be increased, and it is possible to reduce the roughness and improve the other lithography properties.

The acid dissociation constant (pKa) of the conjugate acid of the (D1) component is less than 3, preferably 0.4 or more and less than 3, more preferably 1.0 to 2.95, and particularly preferably 1.5 to 2.90.

When the pKa of the conjugate acid of the (D1) component is less than 3, exposure stability is secured. Meanwhile, when the pKa of the conjugate acid of the (D1) component is equal to or greater than the preferred lower limit, it is more possible to reduce the roughness and improve the other lithography properties.

The "acid dissociation constant (pKa)" of the present invention refers to an index generally used for indicating an acid strength of a target substance.

The pKa of the conjugate acid of the (D1) component can be obtained by measurement according to a general method. In addition, a value calculated by using well-known software such as "ACD/Labs" (product name, manufactured by Advanced Chemistry Development, Inc.) can be used.

Preferred examples of the (D1) component include a compound represented by the following general formula (d1) of which a conjugate acid has an acid dissociation constant (pKa) of less than 3.

[Chemical formula 33]

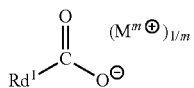
(d1)

[In the formula, Rd¹ is a cyclic group which may have a substituent, a chain-like alkyl group which may have a substituent, or a chain-like alkenyl group which may have a substituent. m is an integer of equal to or greater than 1, and M^{m+} is an m-valent organic cation.]

Rd¹-C(=O)O⁻: Anion Part

In the formula (d1), Rd¹ is a cyclic group which may have a substituent, a chain-like alkyl group which may have a substituent, or a chain-like alkenyl group which may have a substituent.

Cyclic Group which May have a Substituent:

The cyclic group is preferably a cyclic hydrocarbon group, and the cyclic hydrocarbon group may be an aromatic hydrocarbon group, or may be an aliphatic hydrocarbon group. The aliphatic hydrocarbon group means a hydrocarbon group having no aromaticity. In addition, the aliphatic hydrocarbon group may be saturated or unsaturated, and in general, it is preferably saturated.

The aromatic hydrocarbon group for Rd¹ is a hydrocarbon group having an aromatic ring. The number of carbon atoms of the aromatic hydrocarbon group is preferably 3 to 30, further preferably 5 to 30, still further preferably 5 to 20, particularly preferably 6 to 15, and most preferably 6 to 10. Here, the number of carbon atoms does not include the number of carbon atoms in the substituent.

Specific examples of an aromatic ring contained in the aromatic hydrocarbon group for Rd¹ include benzene, fluorene, naphthalene, anthracene, phenanthrene, biphenyl, or an aromatic heterocycle in which a portion of carbon atoms constituting these aromatic rings is substituted with a heteroatom. Examples of the heteroatom in the aromatic heterocycle include an oxygen atom, a sulfur atom, and a nitrogen atom.

Specific examples of the aromatic hydrocarbon group for Rd¹ include a group obtained by removing one hydrogen atom from the aromatic ring (aryl group: for example, a phenyl group and a naphthyl group), a group in which one hydrogen atom of the aromatic ring is substituted with an alkylene group (for example, an aryl alkyl group such as a benzyl group, a phenethyl group, a 1-naphtyl methyl group, a 2-naphtyl methyl group, a 1-naphtyl ethyl group, and a 2-naphtyl ethyl group). The number of carbon atoms of the alkylene group (an alkyl chain in an aryl alkyl group) preferably 1 to 4, more preferably 1 to 2, and particularly preferably 1.

Among them, as the aromatic hydrocarbon group for Rd¹, a phenyl group or a naphthyl group is more preferable.

Examples of the cyclic aliphatic hydrocarbon group for Rd¹ include an aliphatic hydrocarbon group including a ring in a structure.

Examples of the aliphatic hydrocarbon group including a ring in this structure include an aliphatic hydrocarbon group (a group obtained by removing one hydrogen atom from an aliphatic hydrocarbon ring), a group in which an alicyclic hydrocarbon group is bonded to a terminal of a linear or branched aliphatic hydrocarbon group, and a group in which an alicyclic hydrocarbon group is present in the middle of the linear or branched aliphatic hydrocarbon group.

The alicyclic hydrocarbon group preferably has 3 to 20 carbon atoms, and further preferably has 3 to 12 carbon atoms.

The alicyclic hydrocarbon group may be a polycyclic group or a monocyclic group. As the monocyclic alicyclic hydrocarbon group, a group obtained by removing one or more hydrogen atoms from the monocycloalkane is preferable. As the monocycloalkane, a group having 3 to 6 carbon atoms is preferable, and specific examples thereof include cyclopentane and cyclohexane. As the polycyclic alicyclic hydrocarbon group, a group obtained by removing one or more hydrogen atoms from the polycycloalkane is preferable, and as the polycycloalkane, a group having 7 to 30 carbon atoms is preferable. Among them, more preferred examples of the polycycloalkane include polycycloalkane having a bridged ring polycyclic skeleton such as adamantane, norbornane, isobornane, tricyclodecane, and tetracyclododecene; and polycycloalkane having a condensed ring-based polycyclic skeleton such as a cyclic group having a steroid skeleton.

Among them, as the cyclic aliphatic hydrocarbon group for Rd¹, a group obtained by removing one or more hydrogen atom from monocycloalkane or polycycloalkane is preferable, a group obtained by removing one hydrogen atom from polycycloalkane is more preferable, an adamantyl group and a norbornyl group are particularly preferable, and an adamantyl group is most preferable.

The linear or branched aliphatic hydrocarbon group that may be bonded to an alicyclic hydrocarbon group preferably has 1 to 10 carbon atoms, further preferably has 1 to 6 carbon atoms, even more preferably has 1 to 4 carbon atoms, and most preferably has 1 to 3 carbon atoms.

As the linear aliphatic hydrocarbon group, a linear alkylene group is preferable, and specific examples include a methylene group [—CH₂—], an ethylene group [—(CH₂)₂—], a trimethylene group [—(CH₂)₃—], a tetramethylene group [—(CH₂)₄—], and a pentamethylene group [—(CH₂)₅—].

As the branched aliphatic hydrocarbon group, a branched alkylene group is preferable, and specific examples thereof include an alkyl alkylene group such as an alkyl methylene group (e.g., —CH(CH₃)—, —CH(CH₂CH₃)—, —C(CH₃)₂—, —C(CH₃)(CH₂CH₃)—, —C(CH₃)(CH₂CH₂CH₃)—, and —C(CH₂CH₃)₂—); an alkyl ethylene group (e.g., —CH(CH₃)CH₂—, —CH(CH₃)CH(CH₃)—, —C(CH₃)₂CH₂—, —CH(CH₂CH₃)CH₂—, —C(CH₂CH₃)₂—CH₂—); an alkyltrimethylene group (e.g., —CH(CH₃)CH₂CH₂— and —CH₂CH(CH₃)CH₂—; and an alkyltetramethylene group (e.g., —CH(CH₃)CH₂CH₂CH₂— and —CH₂CH(CH₃)CH₂CH₂—). As an alkyl group in an alkyl alkylene group, a linear alkyl group having 1 to 5 carbon atoms is preferable.

In addition, a cyclic hydrocarbon group for Rd¹ may include a heteroatom such as a heterocycle. Specific examples thereof include lactone-containing cyclic groups represented by the general formulae (a2-r-1), (a2-r-3) to (a2-r-7), —SO₂— containing cyclic groups represented by the general formulae (a5-r-1) to (a5-r-4), as well as the heterocyclic groups represented by Chemical formulae (r-hr-1) to (r-hr-16) shown below.

[Chemical formula 34]

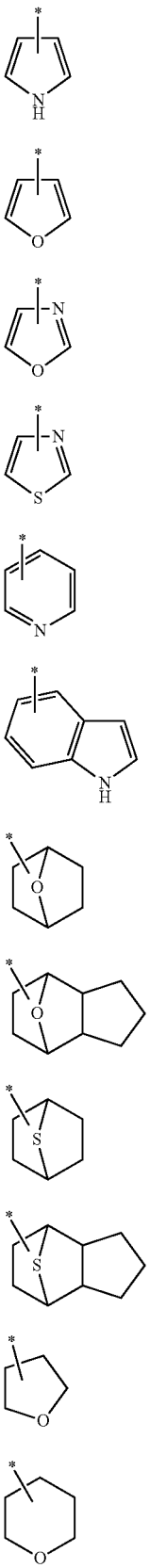

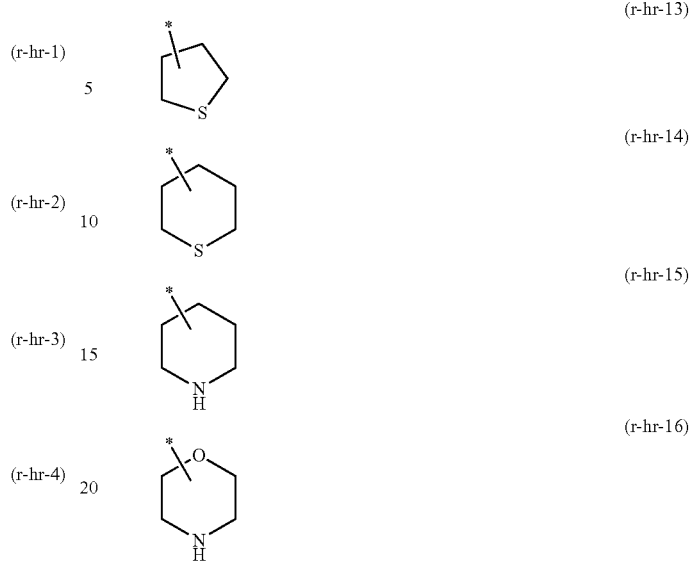

Examples of the substituent which the cyclic group of Rd$^1$ may have include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and is most preferably a methyl group, an ethyl group, a propyl group, an n-butyl group, and a tert-butyl group.

The alkoxy group as the substituent is preferably an alkoxy group having 1 to 5 carbon atoms, further preferably a methoxy group, an ethoxy group, an n-propoxy group, an iso-propoxy group, an n-butoxy group, and a tert-butoxy group, and most preferably a methoxy group and an ethoxy group.

Examples of the halogen atom as the substituent include a fluorine atom, a chlorine atom, a bromine atom, and an iodine atom, and among them, the fluorine atom is preferable.

Examples of the halogenated alkyl group as the substituent include an alkyl group having 1 to 5 carbon atoms, for example, a group in which at least one or all of the hydrogen atoms of a methyl group, an ethyl group, a propyl group, an n-butyl group, and a tert-butyl group is substituted with a halogen atom.

A carbonyl group as the substituent is a group with which a methylene group (—CH$_2$—) constituting a cyclic hydrocarbon group is substituted.

Chain-Like Alkyl Group which May have Substituent:

The chain-like alkyl group for Rd$^1$ may be a linear alkyl group or a branched alkyl group.

The linear alkyl group preferably has 1 to 20 carbon atoms, more preferably has 1 to 15 carbon atoms, particularly preferably has 1 to 11 carbon atoms, and most preferably has 1 to 5 carbon atoms. Specific examples thereof include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a heneicosyl group, and a docosyl group.

The branched alkyl group preferably has 3 to 20 carbon atoms, more preferably 3 to 15 carbon atoms, and most preferably 3 to 10 carbon atoms. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Among them, the chain-like alkyl group for Rd' preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl group, and a decyl group; and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group are preferable.

Chain Alkenyl Group which May have Substituent:

The chain-like alkenyl group for $Rd^1$ may be a linear alkenyl group or a branched alkenyl group, and the chain-like alkenyl group for $Rd^1$ preferably has 2 to 10 carbon atoms, more preferably 2 to 5 carbon atoms, even more preferably 2 to 4 carbon atoms, and particularly preferably 3 carbon atoms. Examples of the linear alkenyl group include a vinyl group, a propenyl group (allyl group), and a butynyl group. Examples of the branched alkenyl group include 1-methylvinyl group, 2-methylvinyl group, 1-methyl propenyl group, and 2-methyl propenyl group.

Among them, as the chain-like alkenyl group for $Rd^1$, a linear alkenyl group is preferable, a vinyl group and a propenyl group are more preferable, and a vinyl group is particularly preferable.

Examples of a substituent which the chain-like alkyl group or a chain-like alkenyl group for $Rd^1$ may have include an alkoxy group, a halogen atom, a halogenated alkyl group, a hydroxy group, a carbonyl group, an amino group, and a cyclic group for $Rd^1$ above.

Among these, as $Rd^1$, an aromatic hydrocarbon group which may have a substituent, an aliphatic cyclic group which may have a substituent, and a chain-like alkyl group which may have a substituent are preferable, and an aromatic hydrocarbon group which may have a substituent and a chain-like alkyl group which may have a substituent are further preferable.

Examples of the substituent which these groups may have preferably include a hydroxy group, an oxo group, an alkyl group, an aryl group, a fluorine atom, a fluorinated alkyl group, lactone-containing cyclic groups represented by the general formulae (a2-r-1) and (a2-r-3) to (a2-r-7), an ether bond, an ester bond, or a combination thereof. In a case where an ether bond or an ester bond is included as the substituent, an alkylene group may be interposed therebetween. As the substituent in this case, linking groups represented by general formulae (y-al-1) to (y-al-5) described below are preferable.

Preferred Examples of the Anion Part ($Rd^1$-C(=O)—O$^-$) of a Compound Represented by General Formula (d1) Include:

(i) an anion in which $Rd^1$ is an aromatic ring including a hydroxybenzoic acid skeleton and at least one hydrogen atom of the aromatic ring is substituted with a group having a halogen atom, and (ii) an anion in which $Rd^1$ is a linear alkyl group and at least one hydrogen atom of the alkyl group is substituted with a group having a halogen atom.

Among them, the anion of (i) is particularly preferable from the aspect that the lithography properties are easily improved, and the anion in which pKa of the conjugate acid is nearly 3 is further preferable.

(i) Anion in which $Rd^1$ is an Aromatic Ring Including a Hydroxybenzoic Acid Skeleton and at Least One Hydrogen Atom of the Aromatic Ring is Substituted with a Group Having a Halogen Atom:

Here, the "hydroxybenzoic acid skeleton" means a structure represented by the following chemical formula (hba). The bonding positions of —COO$^-$ and —OH which are bonded to the benzene ring may be any of ortho-position, meta-position, and para-position, with the ortho-position being preferable.

[Chemical formula 35]

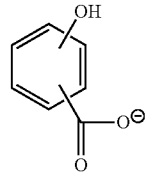

(hba)

The aromatic ring in $Rd^1$ is not particularly limited as long as it is a cyclic conjugated system having (4n+2) π-electrons, and it may be monocyclic or polycyclic. The number of carbon atoms of the aromatic ring is preferably 5 to 30, further preferably 5 to 20, still further preferably 6 to 15, and particularly preferably 6 to 12.

Specific examples of the aromatic ring include an aromatic hydrocarbon ring such as benzene, naphthalene, anthracene, and phenanthrene; and an aromatic heterocycle in which a portion of carbon atoms which forms the aromatic hydrocarbon ring is substituted with a heteroatom. Examples of the heteroatom in the aromatic heterocycle include an oxygen atom, a sulfur atom, and a nitrogen atom. Specific examples of the aromatic heterocycle include a pyridine ring and a thiophene ring.

Among them, as the aromatic ring, an aromatic hydrocarbon ring is preferable, benzene and naphthalene are further preferable, and benzene (that is, a hydroxybenzoic acid skeleton) is particularly preferable from the aspect that the effects of the present invention are further enhanced.

Examples of the "a group having a halogen atom" with which a hydrogen atom of the aromatic ring is substituted include a halogen atom and a halogenated alkyl group.

Examples of the halogen atom include a fluorine atom, a chlorine atom, a bromine atom, and an iodine atom, and among them, the fluorine atom is preferable in terms of the hydrophobicity.

Examples of the halogenated alkyl group include a group in which at least one or all of the hydrogen atoms of an alkyl group is substituted with a halogen atom, and examples of the halogen atom include a fluorine atom, a chlorine atom, a bromine atom, and an iodine atom, among them, the fluorine atom is particularly preferable. Here, the alkyl group is preferably an alkyl group having 1 to 5 carbon atoms, and is further preferably a linear or branched alkyl group having 1 to 5 carbon atoms.

Preferred examples of the anion of (i) include an anion represented by the following Chemical formula (d1-a).

[Chemical formula 36]

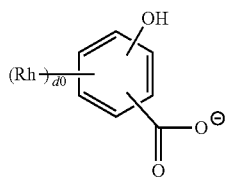

(d1-a)

[In the formula, Rh represents a group having a halogen atom. d0 is an integer of 1 to 4.]

In the formula (d1-a), examples of the group having a halogen atom for Rh include a halogen atom such as a fluorine atom, a chlorine atom, a bromine atom, and an iodine atom, and a halogenated alkyl group.

Specific examples of the anion for (i) are shown below.

In addition, the pKa of each conjugate acid calculated by using "Software V11.02 (1994-2013 ACD/Labs)" (product name, manufactured by Advanced Chemistry Development) is also indicated as follows.

[Chemical formula 37]

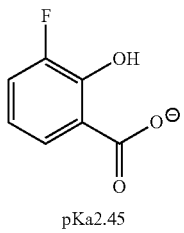

pKa2.45

(d1-a1)

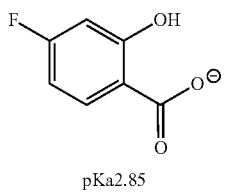

pKa2.85

(d1-a2)

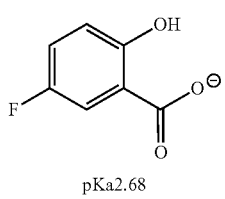

pKa2.68

(d1-a3)

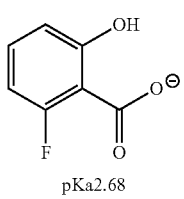

pKa2.68

(d1-a4)

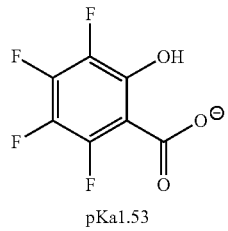

pKa1.53

(d1-a5)

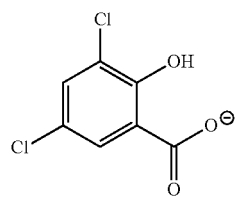

pKa1.99

(d1-a6)

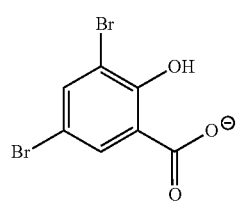

pKa1.96

(d1-a7)

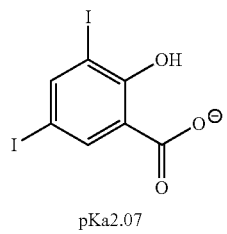

pKa2.07

(d1-a8)

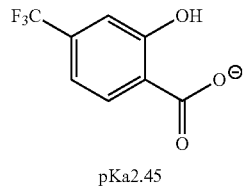

pKa2.45

(d1-a9)

(ii) Anion in which $Rd^1$ is a Linear Alkyl Group and at Least One Hydrogen Atom of the Alkyl Group is Substituted with a Group Having a Halogen Atom:

The number of carbon atoms of the linear alkyl group for $Rd^1$ is preferably 1 to 11, further preferably 1 to 8, and still further preferably 1 to 4 carbon atoms.

Examples of the "a group having a halogen atom" with which a hydrogen atom of the alkyl group is substituted include a halogen atom and a halogenated alkyl group.

Examples of the halogen atom include a fluorine atom, a chlorine atom, a bromine atom, and an iodine atom, and among them, the fluorine atom is preferable in terms of the hydrophobicity.

Examples of the halogenated alkyl group include a group in which at least one or all of the hydrogen atoms of an alkyl group is substituted with a halogen atom, and examples of the halogen atom include a fluorine atom, a chlorine atom, a bromine atom, and an iodine atom, among them, the fluorine atom is particularly preferable. Here, the alkyl group is preferably an alkyl group having 1 to 5 carbon atoms, and is further preferably a linear or branched alkyl group having 1 to 5 carbon atoms.

Preferred examples of the anion of (ii) include an anion in which at least one hydrogen atom of the linear alkyl group having 1 to 11 carbon atoms for $Rd^1$ is substituted with a fluorine atom. The number of carbon atoms of the alkyl group is preferably 1 to 7, and an anion which is a fluorinated alkyl group (a linear perfluoroalkyl group) in which the entire hydrogen atoms of the alkyl group are substituted with a fluorine atom is particularly preferable.

Specific examples of the anion of (ii) are shown below.

In addition, the pKa of each conjugate acid calculated by using "Software V11.02 (1994-2013 ACD/Labs)" (product name, manufactured by Advanced Chemistry Development) is also indicated as follows.

[Chemical formula 38]

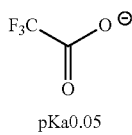

(d1-a11)

pKa0.05

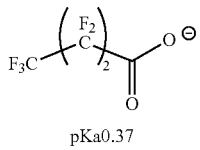

(d1-a12)

pKa0.37

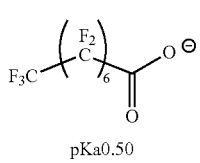

(d1-a13)

pKa0.50

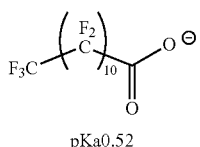

(d1-a14)

pKa0.52

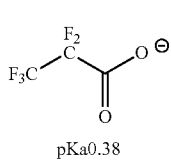

(d1-a15)

pKa0.38

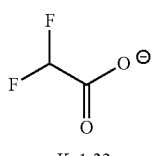

(d1-a16)

pKa1.32

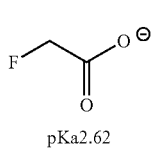

(d1-a17)

pKa2.62

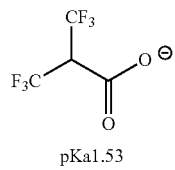

(d1-a18)

pKa1.53

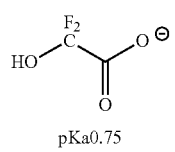

(d1-a19)

pKa0.75

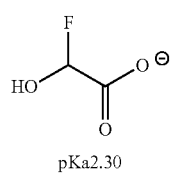

(d1-a20)

pKa2.30

[Chemical formula 39]

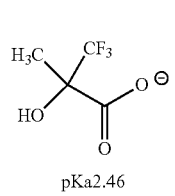

(d1-a21)

pKa2.46

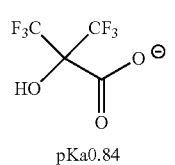

(d1-a22)

pKa0.84

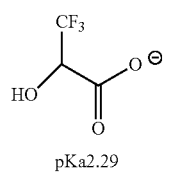

(d1-a23)

pKa2.29

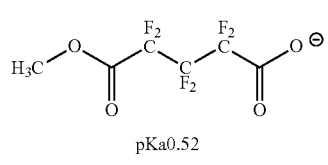

(d1-a24)

pKa0.52

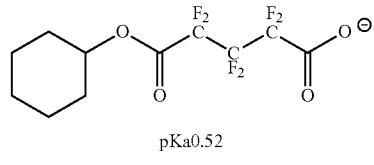

(d1-a25)

pKa0.52

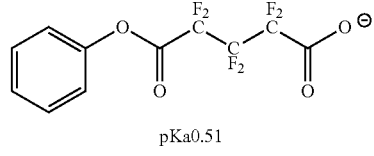

(d1-a26)

pKa0.51

-continued

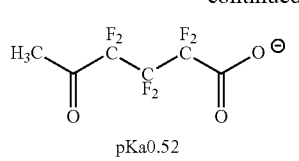
pKa0.52
(d1-a27)

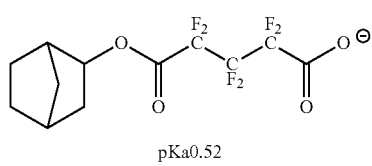
pKa0.52
(d1-a28)

$(M^{m+})_{1/m}$: Cation Part

In the formula (d1), m is an integer of 1 or more, and $M^{m+}$ is an m-valent organic cation.

As the organic cation in $M^{m+}$, an onium cation is preferable, and a sulfonium cation and an iodonium cation are further preferable.

Preferred examples of the $(M^{m+})_{1/m}$ (cation part) include organic cations represented by the following general formulae (ca-1) to (ca-4).

[Chemical formula 40]

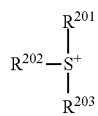 (ca-1)

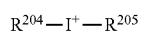 (ca-2)

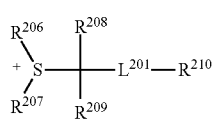 (ca-3)

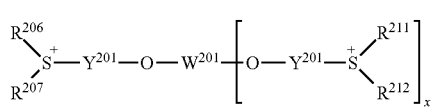 (ca-4)

[In the formulae, $R^{201}$ to $R^{207}$, and $R^{211}$ and $R^{212}$ each independently represent an aryl group which may have a substituent, an alkyl group, or an alkenyl group, and $R^{201}$ to $R^{203}$, $R^{206}$ and $R^{207}$, and $R^{211}$ and $R^{212}$ may be bonded to each other so as to form a ring together with the sulfur atom in the formula. $R^{208}$ and $R^{209}$ each independently represent a hydrogen atom or an alkyl group having 1 to 5 carbon atoms, $R^{210}$ represents an aryl group which may have a substituent, an alkyl group which may have a substituent, an alkenyl group which may have a substituent, or —$SO_2$— containing cyclic group which may have a substituent, $L^{201}$ represents —C(=O)— or —C(=O)—O—, $Y^{201}$'s each independently represent an arylene group, an alkylene group, or an alkenylene group, x is 1 or 2, and $W^{201}$ represents a (x+1) valent linking group.]

Examples of the aryl group for $R^{201}$ to $R^{207}$ and $R^{211}$ and $R^{212}$ include an unsubstituted aryl group having 6 to 20 carbon atoms, and a phenyl group and a naphthyl group are preferable.

As the alkyl group for $R^{201}$ to $R^{207}$ and $R^{211}$ and $R^{212}$, a chain-like or cyclic alkyl group having 1 to 30 carbon atoms is preferable.

As the alkenyl group for $R^{201}$ to $R^{202}$ and $R^{211}$ and $R^{212}$, an alkenyl group having 2 to 10 carbon atoms is preferable.

Examples of the substituent that $R^{201}$ to $R^{207}$ and $R^{210}$ to $R^{212}$ may have include an alkyl group, a halogen atom, a halogenated alkyl group, a carbonyl group, a cyano group, an amino group, an aryl group, and the groups represented by the following general formulae (ca-r-1) to (ca-r-7).

[Chemical formula 41]

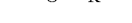 [ca-r-1]

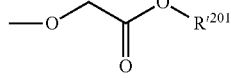 [ca-r-2]

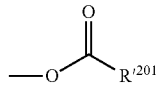 [ca-r-3]

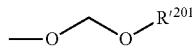 [ca-r-4]

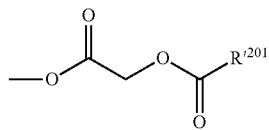 [ca-r-5]

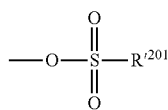 [ca-r-6]

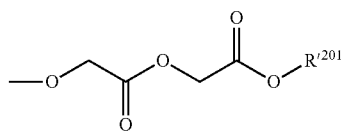 [ca-r-7]

[In the formulae, $R^{'201}$'s each independently represent a hydrogen atom, acyclic group which may have a substituent, a chain-like alkyl group which may have a substituent, or a chain-like alkenyl group which may have a substituent.]

Examples of the cyclic group which may have a substituent, the chain-like alkyl group which may have a substituent, or the chain-like alkenyl group which may have a substituent for $R^{'201}$ include those for $Rd^1$ in the formula (d1), and examples of the cyclic group which may have a substituent or the chain-like alkyl group which may have a substituent also include the same as those for the acid dissociable group represented by the formula (a1-r-2).

In a case where $R^{201}$ to $R^{203}$, $R^{206}$ and $R^{207}$, $R^{211}$ and $R^{212}$ each combination is bonded to each other so as to form a ring together with the sulfur atom in the formula, the bonding may be performed via a heteroatom such as a sulfur atom, an oxygen atom, and a nitrogen atom, or a functional group such as a carbonyl group, —SO—, —$SO_2$—, —$SO_3$—, —COO—, —CONH— and —N($R_N$)— (where $R_N$ is an alkyl group having 1 to 5 carbon atoms). As a ring to be formed, one ring including a sulfur atom in the formula in the ring skeleton is preferably 3- to 10-membered rings including a sulfur atom, and is particularly preferably 5- to 7-membered rings including a sulfur atom. Specific examples of the ring to be formed include a thiophene ring, a thiazole ring, a benzothiophene ring, a thianthrene ring, a benzothiophene ring, a dibenzothiophene ring, a 9H-thioxanthene ring, a thioxanthone ring, a thianthrene ring, a phenoxathiin ring, a tetrahydrothiophenium ring, and a tetrahydrothiopyranium ring.

$R^{208}$ and $R^{209}$ each independently represent a hydrogen atom or an alkyl group having 1 to 5 carbon atoms, and a hydrogen atom or an alkyl group having 1 to 3 carbon atoms is preferable, and in a case of the alkyl group, the alkyl groups may be bonded to each other so as to form a ring.

$R^{210}$ is an aryl group which may have a substituent, an alkyl group which may have a substituent, an alkenyl group which may have a substituent, or a —SO$_2$— containing cyclic group which may have a substituent.

Examples of the aryl group for $R^{210}$ include an unsubstituted aryl group having 6 to 20 carbon atoms, and a phenyl group and a naphthyl group are preferable.

The alkyl group for $R^{210}$ is a chain-like or cyclic alkyl group, and preferably has 1 to 30 carbon atoms.

The alkenyl group for $R^{210}$ preferably has 2 to 10 carbon atoms.

The —SO$_2$— containing cyclic group which may have a substituent for $R^{210}$ is preferably a "—SO$_2$-containing polycyclic group", and further preferably a group represented by the general formula (a5-r-1).

$Y^{201}$'s each independently represent an arylene group, an alkylene group, and an alkenylene group.

Examples of the arylene group for $Y^{201}$ include a group obtained by removing one hydrogen atom from the aryl group exemplified as an aromatic hydrocarbon group for $Rd^1$ in the formula (d1).

Examples of the alkylene group or the alkenylene group for $Y^{201}$ include groups obtained by removing one hydrogen atom from groups exemplified as the chain-like alkyl group or the chain-like alkenyl group for $Rd^1$ in the formula (d1).

In the formula (ca-4), x is 1 or 2.

$W^{201}$ is (x+1)valent, that is, a divalent or trivalent linking group.

The divalent linking group for $W^{201}$ is preferably a divalent hydrocarbon group which may have a substituent, or a divalent hydrocarbon group which may have a substituent, which is the same as that for $Ya^{21}$ in the general formula (a2-1). The divalent linking group for $W^{201}$ may be linear, branched, or cyclic, and is preferably cyclic. Among them, a group in which two carbonyl groups are bonded at both ends of the arylene group is preferable. Examples of the arylene group include a phenylene group and a naphthylene group, and the phenylene group is particularly preferable.

Examples of the trivalent linking group for $W^{201}$ include a group obtained by removing one hydrogen atom from the divalent linking group for $W^{201}$ and a group to which one divalent linking group is further bonded to another divalent linking group. The trivalent linking group in $W^{201}$ is preferably a group in which two carbonyl groups are bonded to the arylene group.

Preferred examples of the cation represented by the formula (ca-1) include cations represented by the following formulae (ca-1-1) to (ca-1-67).

[Chemical formula 42]

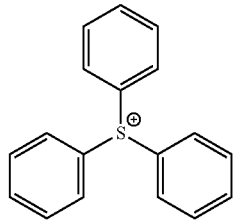
(ca-1-1)

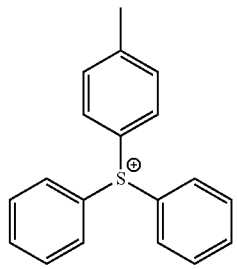
(ca-1-2)

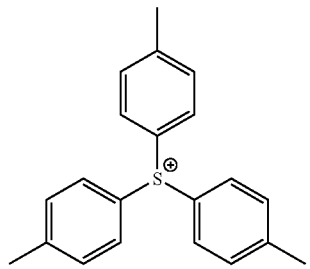
(ca-1-3)

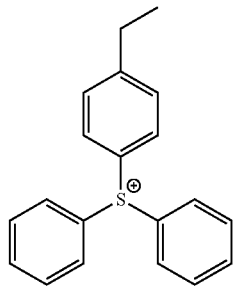
(ca-1-4)

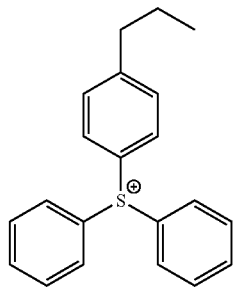
(ca-1-5)

(ca-1-6)
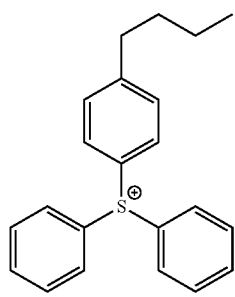
(ca-1-7)
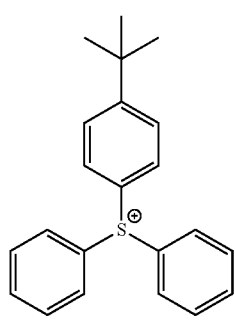
(ca-1-8)
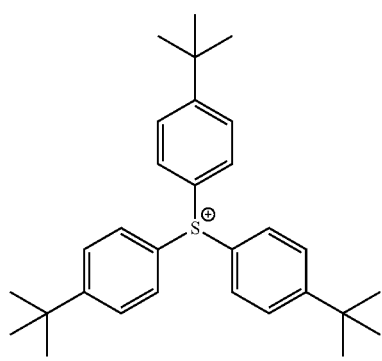
(ca-1-9)
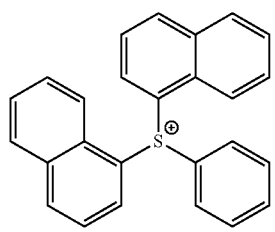
(ca-1-10)
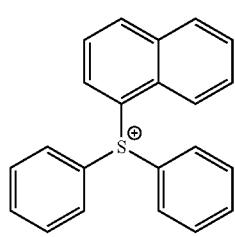
(ca-1-11)
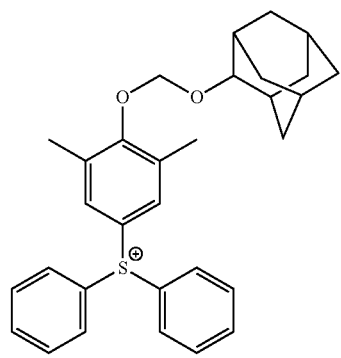
(ca-1-12)
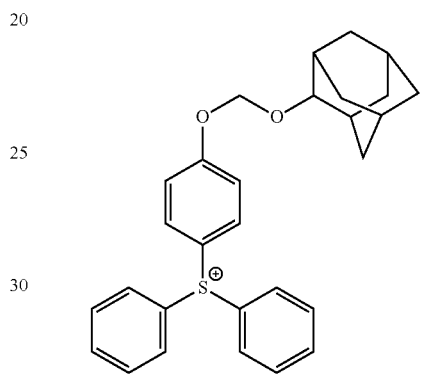
(ca-1-13)
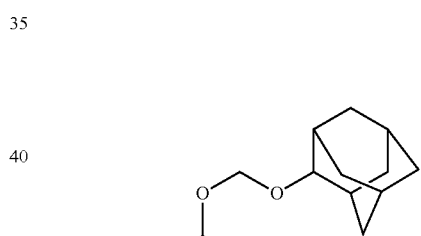
(ca-1-14)
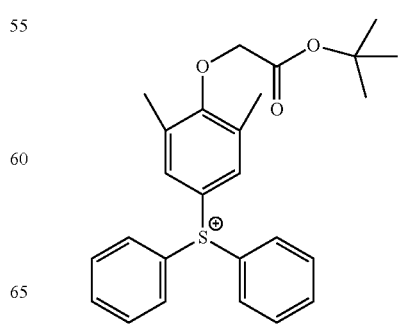

(ca-1-15)
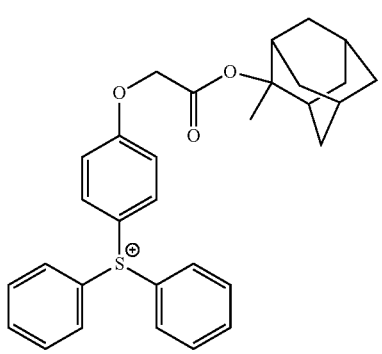
(ca-1-19)
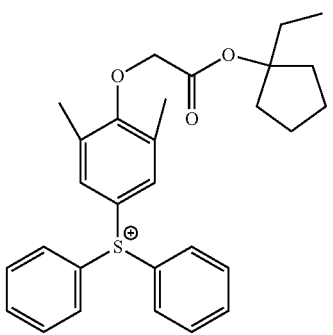
(ca-1-16)
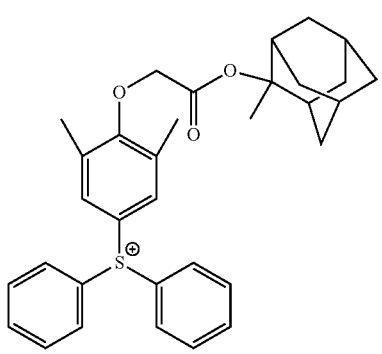
[Chemical formula 43]
(ca-1-20)
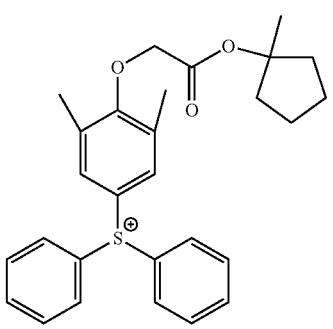
(ca-1-17)
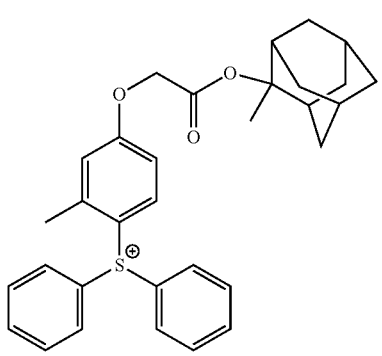
(ca-1-21)
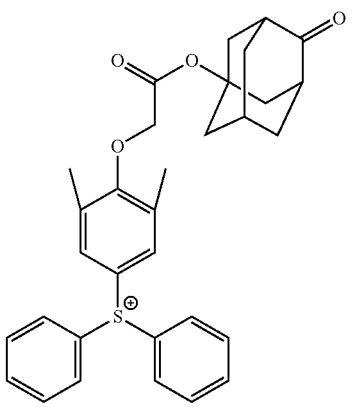
(ca-1-18)
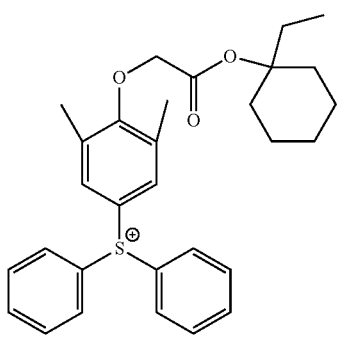
(ca-1-22)
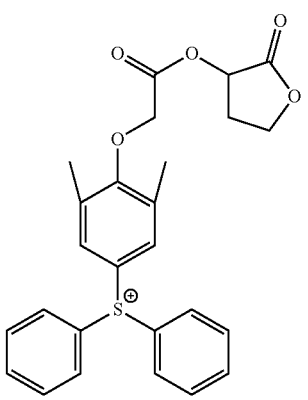

(ca-1-23)
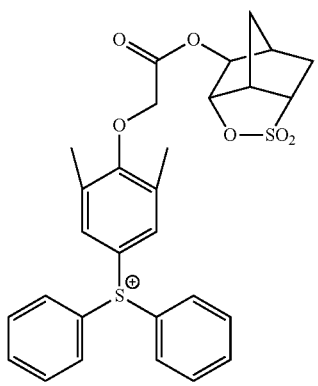
(ca-1-24)
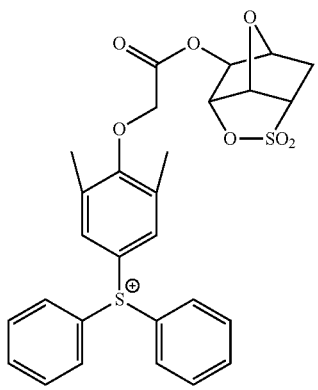
(ca-1-25)
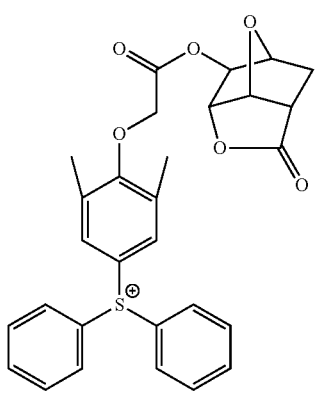
(ca-1-26)
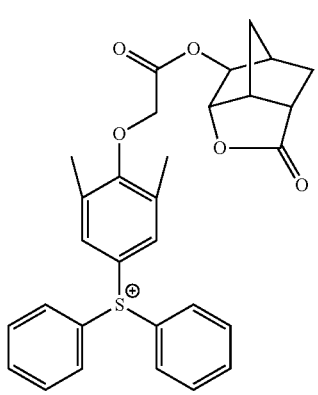
(ca-1-27)
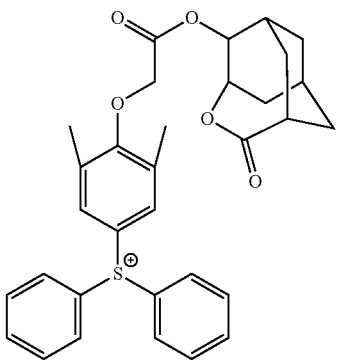
(ca-1-28)
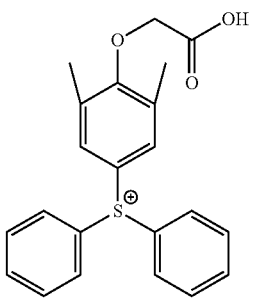
(ca-1-29)
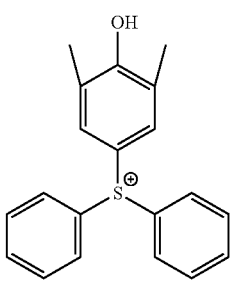
(ca-1-30)
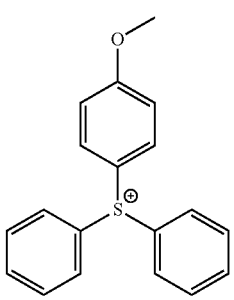
(ca-1-31)
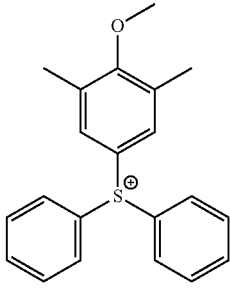

(ca-1-32)
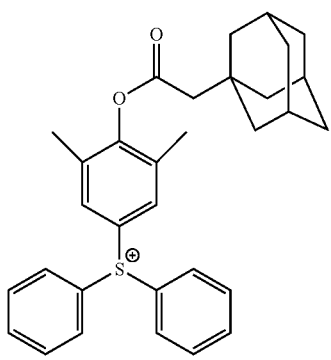
(ca-1-33)
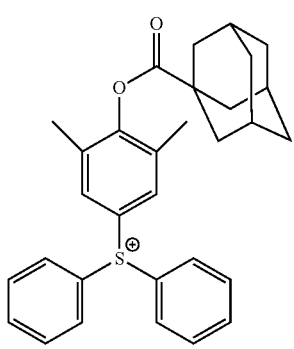
[Chemical formula 44]
(ca-1-34)
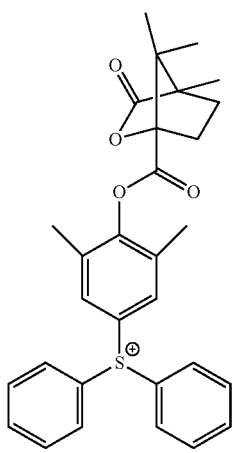
(ca-1-35)
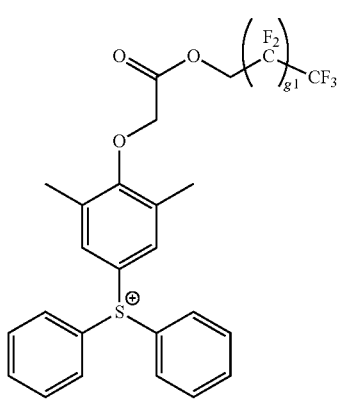
(ca-1-36)
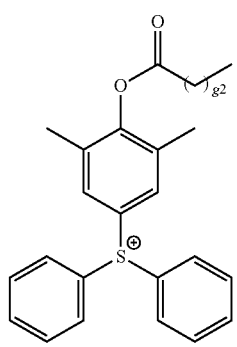
(ca-1-37)
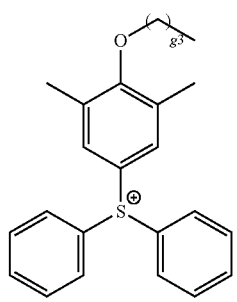
(ca-1-38)
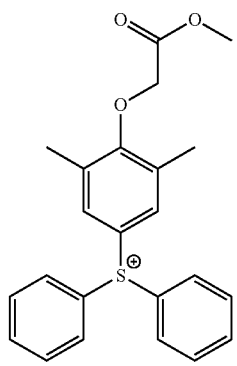
(ca-1-39)
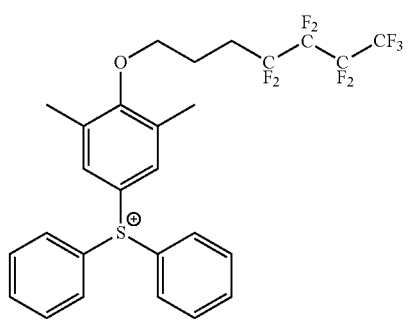

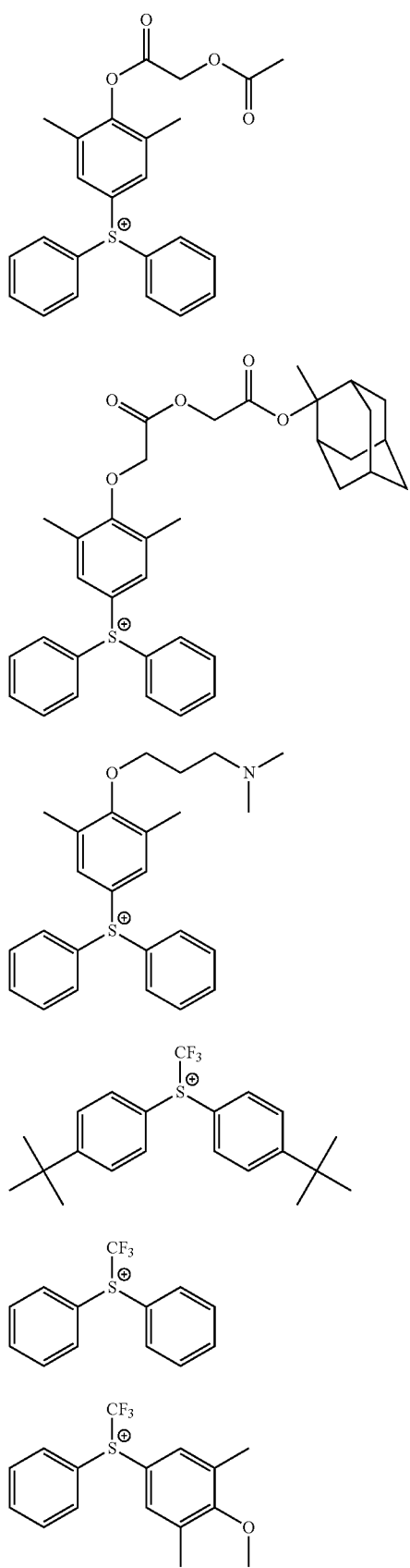
(ca-1-40)
(ca-1-41)
(ca-1-42)
(ca-1-43)
(ca-1-44)
(ca-1-45)
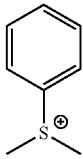
(ca-1-46)
(ca-1-47)
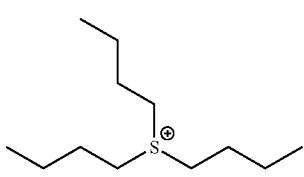
(ca-1-48)
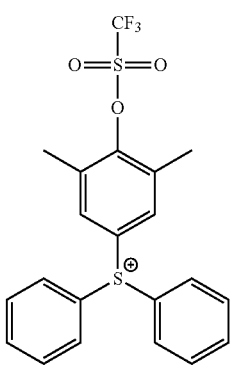
(ca-1-49)
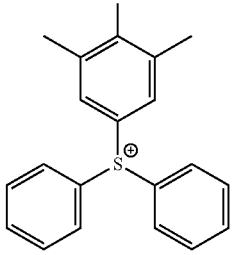
(ca-1-50)
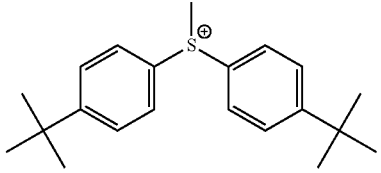
(ca-1-51)
[In the formulae, g1, g2, and g3 represent repeated numbers; g1 is an integer of 1 to 5, g2 is an integer of 0 to 20, and g3 is an integer of 0 to 20.]

[Chemical formula 45]
(ca-1-52)
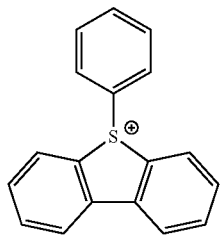
(ca-1-53)
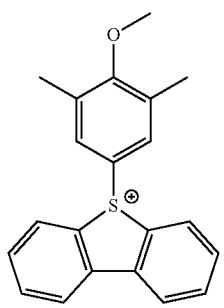
(ca-1-54)
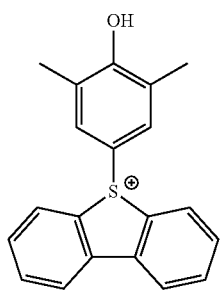
(ca-1-55)
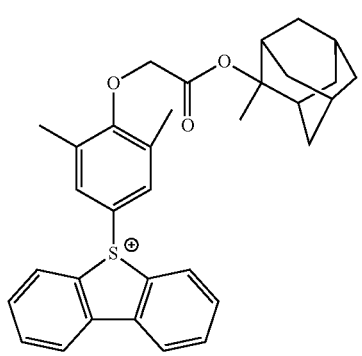
(ca-1-56)
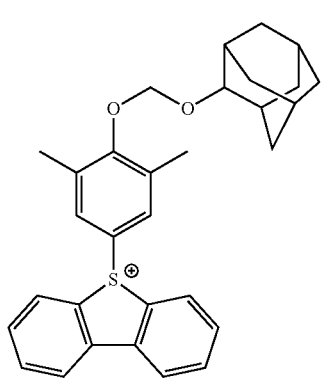
(ca-1-57)
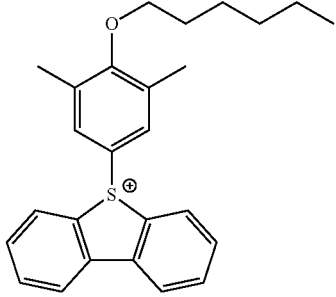
(ca-1-58)
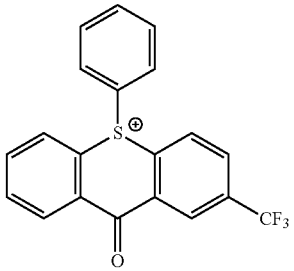
(ca-1-59)
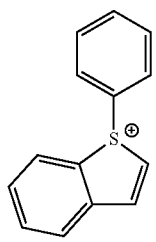
(ca-1-60)
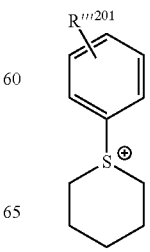
(ca-1-61)

(ca-1-62)
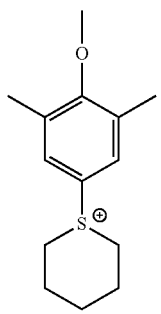

(ca-1-63)
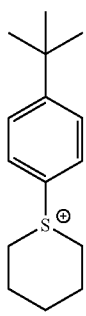

(ca-1-64)
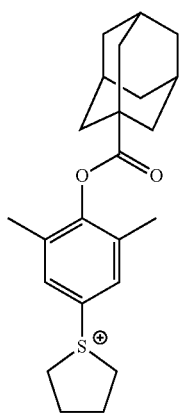

(ca-1-65)
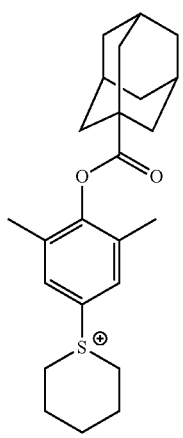

(ca-1-66)
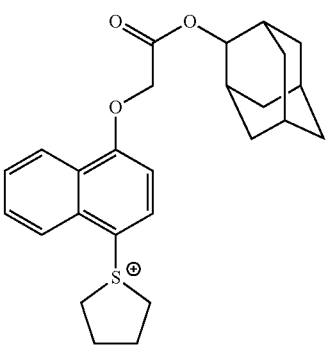

(ca-1-67)
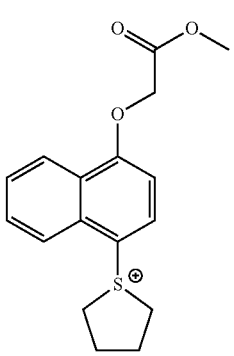

[In the formula, $R''^{201}$ is a hydrogen atom or a substituent, and the substituent is the same as the substituent which $R^{201}$ to $R^{207}$ and $R^{210}$ to $R^{212}$ may have.]

Specifically, preferred examples of the cation represented by the formula (ca-2) include a diphenyl iodonium cation and a bis (4-tert-butylphenyl) iodonium cation.

Specifically, preferred examples of the cation represented by the formula (ca-3) include cations represented by the following formulae (ca-3-1) to (ca-3-6).

[Chemical formula 46]

(ca-3-1)
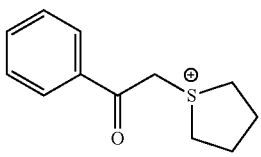

(ca-3-2)
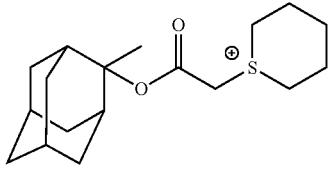

(ca-3-3)

(ca-3-4)
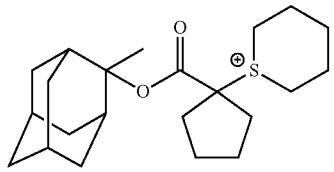

(ca-3-5)
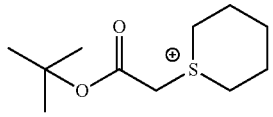

(ca-3-6)
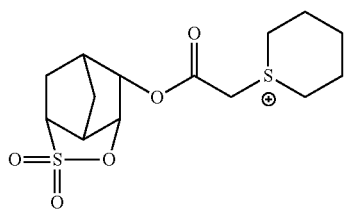

Specifically, preferred examples of the cation represented by the formula (ca-4) include cations represented by the following formulae (ca-4-1) and (ca-4-2).

[Chemical formula 47]

(ca-4-1)
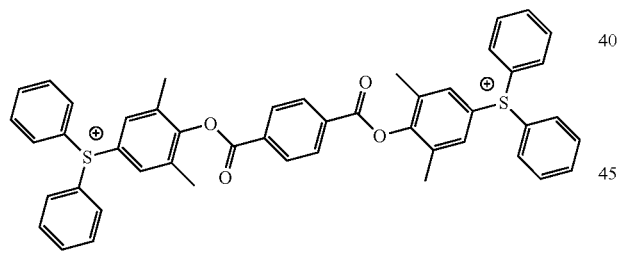

(ca-4-2)
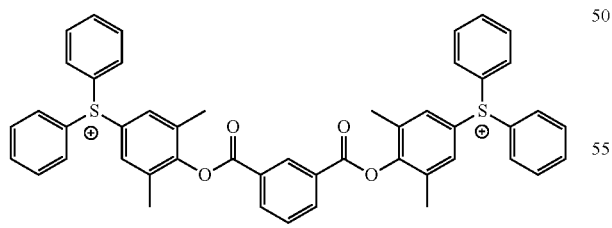

Among the above examples, $(M^{m+})_{1/m}$ (cation part) is preferably cation represented by general formula (ca-1), and is further preferably cations represented by the formulae (ca-1-1) to (ca-1-67).

Particularly preferable examples of the (D1) component include a compound represented by the following general formula (d1-10).

[Chemical formula 48]

(d1-10)
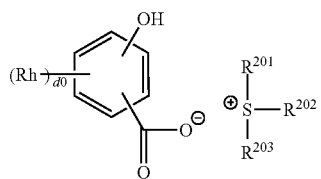

[In the formula, $R^{201}$ to $R^{203}$ are the same as $R^{201}$ to $R^{203}$ in the formula (ca-1). Rh and d0 are the same as Rh and d0 in the formula (d1-a), respectively.]

Preferred examples of the (D1) component are shown below.

In addition, the pKa of each conjugate acid calculated by using "Software V11.02 (1994-2013 ACD/Labs)" (product name, manufactured by Advanced Chemistry Development) is also indicated as follows.

[Chemical formula 49]

(d1-11)
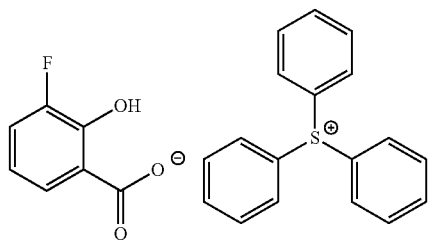

Compound (d1-11): pKa 2.45

(d1-12)
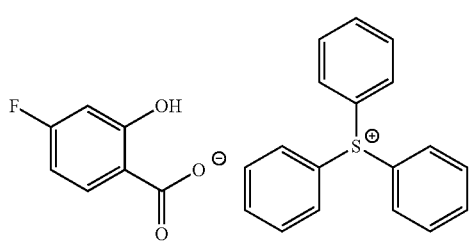

Compound (d1-12): pKa 2.85

[Chemical formula 50]

(d1-13)
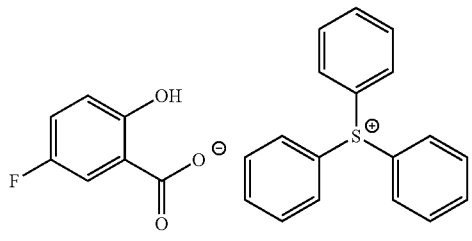

Compound (d1-13): pKa 2.68

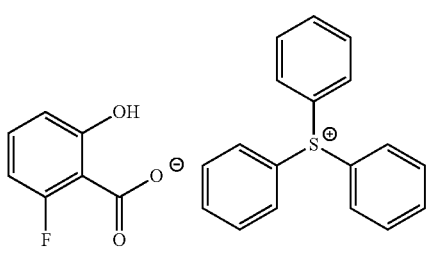

Compound (d1-14): pKa 2.68

[Chemical formula 51]

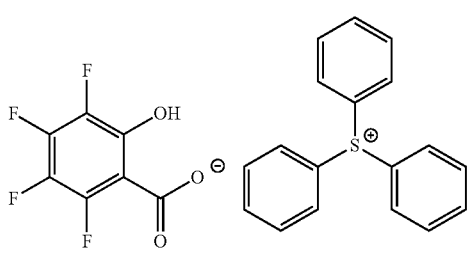

Compound (d1-15): pKa 1.53

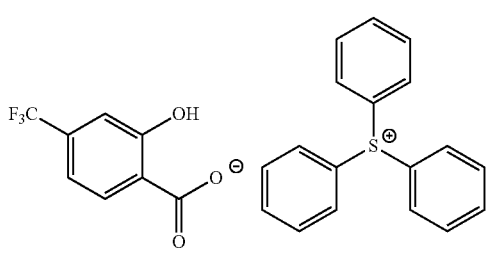

Compound (d1-16): pKa 2.45

In the resist composition of the present aspect, the (D1) component may be used alone or two or more types thereof may be used in combination.

In the resist composition of the present aspect, the content of the (D1) component is preferably 0.5 to 10 parts by mass, further preferably 0.5 to 8 parts by mass, and still further preferably 1 to 8 parts by mass, with respect to 100 parts by mass of the (A) component.

When the content of the (D1) component is equal to or greater than the preferred lower limit, the exposure stability of the resist composition is easily improved. In addition, it is more possible to reduce the roughness and improve the other lithography properties. On the other hand, when the content of the (D1) component is equal to or less than the preferred upper limit, it is possible to maintain the excellent sensitivity, and to obtain excellent throughput.

(D2) Component

The resist composition of the present aspect may contain an acid diffusion control agent component (hereinafter, referred to as a "(D2) component") in addition to the (D1) component as long as the effect of the present invention is not impaired.

Examples of the (D2) component include a photodegradable base (D21) (hereinafter, referred to as a "(D21) component") which is decomposed upon exposure to lose acid diffusion controllability, and a nitrogen-containing organic compound (D22) (hereinafter, referred to as a "(D22) component) which does not correspond to the (D21) component.

Regarding (D21) Component

The (D21) component is preferably one or more of compounds selected from the group consisting of a compound represented by the following general formula (d2-2) (hereinafter, referred to as "(d2-2) component") and a compound represented by the following general formula (d2-3) (hereinafter, referred to as "(d2-3) component").

Since the (d2-2) and (d2-3) components are decomposed in the exposed area of the resist film, the acid diffusion control properties (basicity) are lost. For this reason, the (d2-2) and (d2-3) components do not act as a quencher in the exposed area, but act as a quencher in the unexposed area.

[Chemical formula 52]

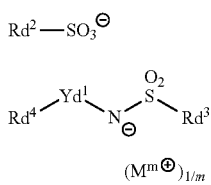

[In the formulae, $Rd^2$ to $Rd^4$ are a cyclic group which may have a substituent, a chain-like alkyl group which may have a substituent, or a chain-like alkenyl group which may have a substituent. Here, a fluorine atom is not bonded to the carbon atom in $Rd^2$ adjacent to the S atom in the formula (d2-2). $Yd^1$ is a single bond or a divalent linking group. m is an integer of 1 or more, and $M^{m+}$'s each independently represent an m-valent organic cation.]

(d2-2) Component

Anion Part

In the formula (d2-2), $Rd^2$ is a cyclic group which may have a substituent, a chain-like alkyl group which may have a substituent, or a chain-like alkenyl group which may have a substituent, and examples thereof include the same as those for $Rd^1$ in the formula (d1).

Here, a fluorine atom is not bonded to the carbon atom in $Rd^2$ adjacent to the S atom (the carbon atom is not substituted with a fluorine atom). With this, the anion of the (d2-2) component becomes an appropriate weak acid anion, and thus the quenching ability as the (D2) component is improved.

$Rd^2$ is preferably a chain-like alkyl group which may have a substituent, or aliphatic cyclic group which may have a substituent. The chain-like alkyl group preferably has 1 to 10 carbon atoms, and further preferably has 3 to 10 carbon atoms. As the aliphatic cyclic group, a group (which may have a substituent) obtained by removing one or more hydrogen atoms from adamantane, norbornane, isobornane, tricyclodecane, and tetracyclododecane, and is further preferably a group obtained by removing one or more hydrogen atoms from the camphor.

The hydrocarbon group for $Rd^2$ may have a substituent, and examples of the substituent include the same as the substituents which the hydrocarbon group (an aromatic hydrocarbon group, an aliphatic cyclic group, a chain-like alkyl group) for $Rd^1$ of the formula (d1) may have.

Preferred examples of the anion part having the (d2-2) component are shown below.

[Chemical formula 53]

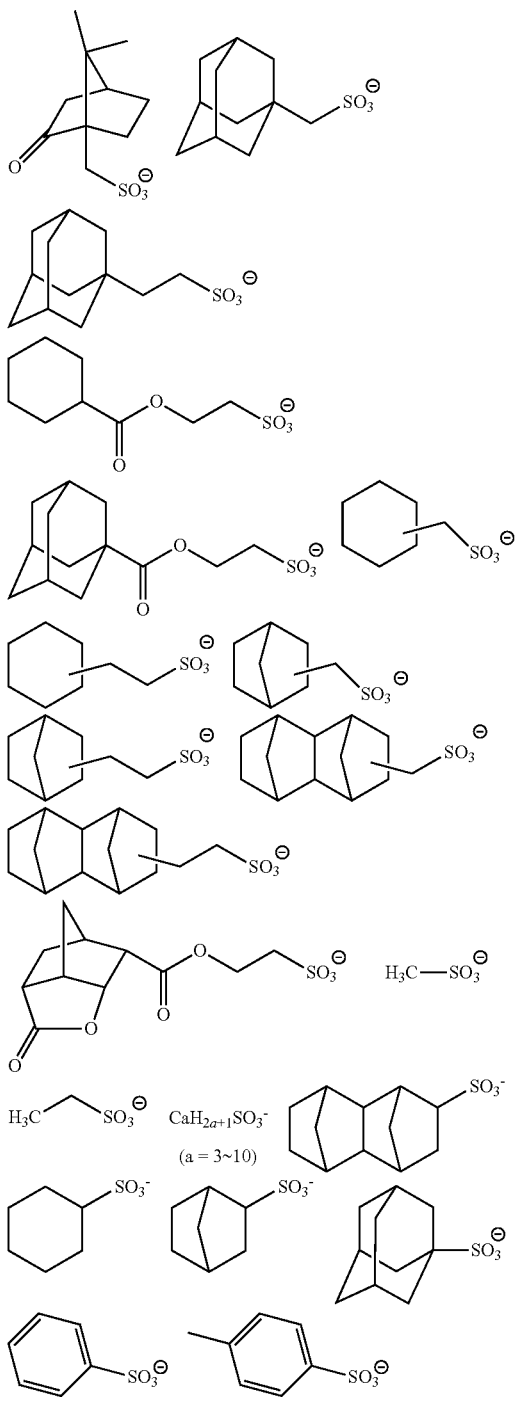

Cation Part

In the formula (d2-2), m is an integer of 1 or more, and $M^{m+}$ is an m-valent organic cation.

As the $M^{m+}$ organic cation, the same cations as those represented by the general formulae (ca-1) to (ca-4) are preferable, the cation represented by the general formula (ca-1) is further preferable, and the cation represented by each of the formulae (ca-1-1) to (ca-1-67) is still further preferable.

The (d2-2) component may be used alone, and two or more types thereof may be used in combination.

(d2-3) Component
Anion Part

In the formula (d2-3), $Rd^3$ is a cyclic group which may have a substituent, a chain-like alkyl group which may have a substituent, or a chain-like alkenyl group which may have a substituent. Examples thereof include the same as those for $Rd^1$ in the formula (d1), and a cyclic group containing a fluorine atom, a chain-like alkyl group, or a chain-like alkenyl group is preferable. Among them, the fluorinated alkyl group is preferable, and the same groups as the fluorinated alkyl groups exemplified for $Rd^1$ are further preferable.

In the formula (d2-3), $Rd^4$ is a cyclic group which may have a substituent, a chain-like alkyl group which may have a substituent, or a chain-like alkenyl group which may have a substituent, and examples thereof include the same as those exemplified for $Rd^1$ in the formula (d1).

Among them, the alkyl group which may have a substituent, the alkoxy group, the alkenyl group, and the cyclic group are preferable.

The alkyl group for $Rd^4$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an iso-pentyl group, and a neopentyl group. At least one hydrogen atom in an alkyl group for $Rd^4$ may be substituted with a hydroxyl group, a cyano group, or the like.

The alkoxy group for $Rd^4$ is preferably an alkoxy group having 1 to 5 carbon atoms, and specific examples of the alkoxy group having 1 to 5 carbon atoms include a methoxy group, an ethoxy group, an n-propoxy group, an iso-propoxy group, an n-butoxy group, and a tert-butoxy group. Among them, the methoxy group and the ethoxy group are preferable.

Examples of the alkenyl group for $Rd^4$ include the same as those exemplified for $Rd^1$ in the formula (d1), and a vinyl group, a propenyl group (an allyl group), a 1-methyl propenyl group, and a 2-methyl propenyl group are preferable. These groups may further have an alkyl group having 1 to 5 carbon atoms or a halogenated alkyl group having 1 to 5 carbon atoms as a substituent.

Examples of the cyclic group for $Rd^4$ include the same as those exemplified for $Rd^1$ in the formula (d1), and preferred examples thereof include an alicyclic group obtained by removing one or more hydrogen atom from cycloalkane such as cyclopentane, cyclohexane, adamantane, norbornane, isobornane, tricyclodecane, and tetracyclododecane; and an aromatic group such as a phenyl group and a naphthyl group. In a case where $Rd^4$ is an alicyclic group, the resist composition is dissolved well in an organic solvent, and thus the lithography properties become excellent. Further, in a case where $Rd^4$ is an aromatic group, in the lithography in which EUV or the like is set as an exposure light source, the resist composition is excellent in the light absorption efficiency, and thus the sensitivity and the lithography properties become excellent.

In the formula (d2-3), $Yd^1$ is a single bond or a divalent linking group.

The divalent linking group for $Yd^1$ is not particularly limited, and examples thereof include a divalent hydrocarbon group which may have a substituent (an aliphatic hydrocarbon group and an aromatic hydrocarbon group), and a divalent linking group containing a heteroatom. Examples thereof include the same as those exemplified for the divalent hydrocarbon group which may have a substituent, and the divalent linking group containing a heteroatom in the description of the divalent linking group for $Ya^{21}$ in the formula (a2-1).

$Yd^1$ is preferably a carbonyl group, an ester bond, an amide bond, an alkylene group, or a combination thereof. The alkylene group is preferably a linear or branched alkylene group, and further preferably a methylene group or an ethylene group.

Preferred examples of the anion part of the (d2-3) component are shown below.

[Chemical formula 54]

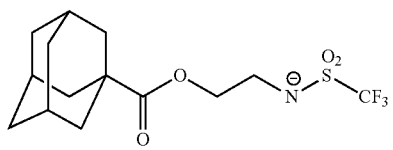
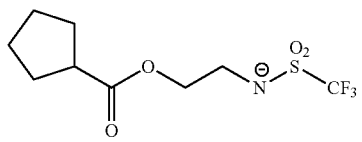
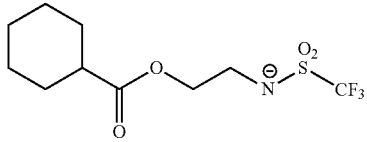
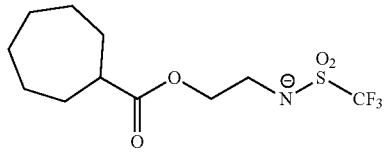
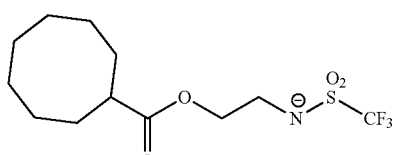
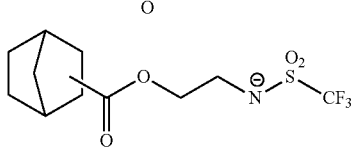
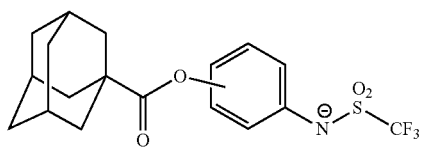
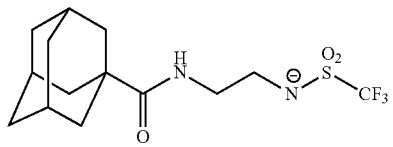
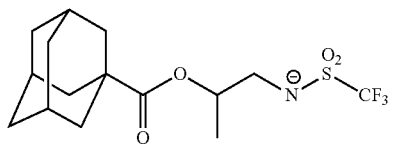

-continued

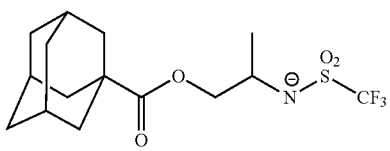
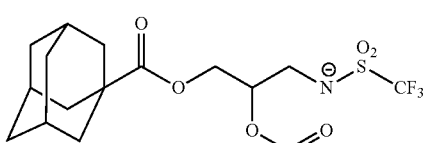
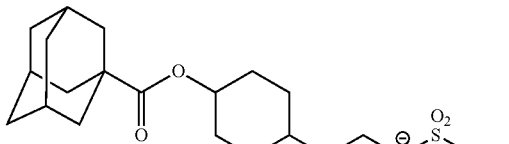
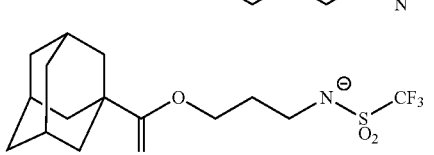
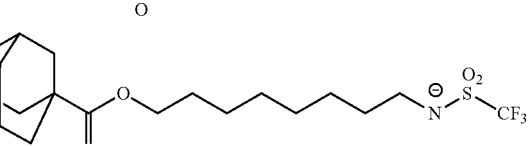
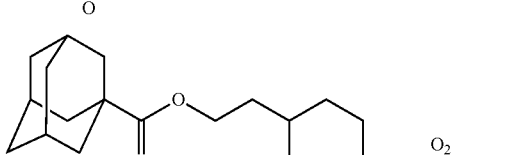
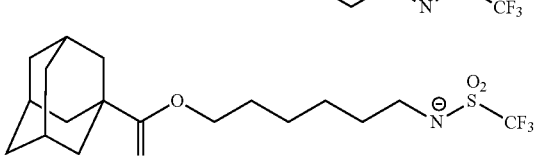

[Chemical formula 55]

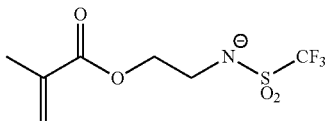
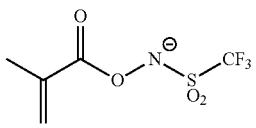
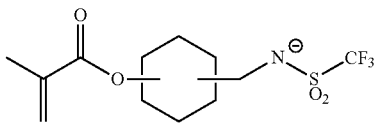

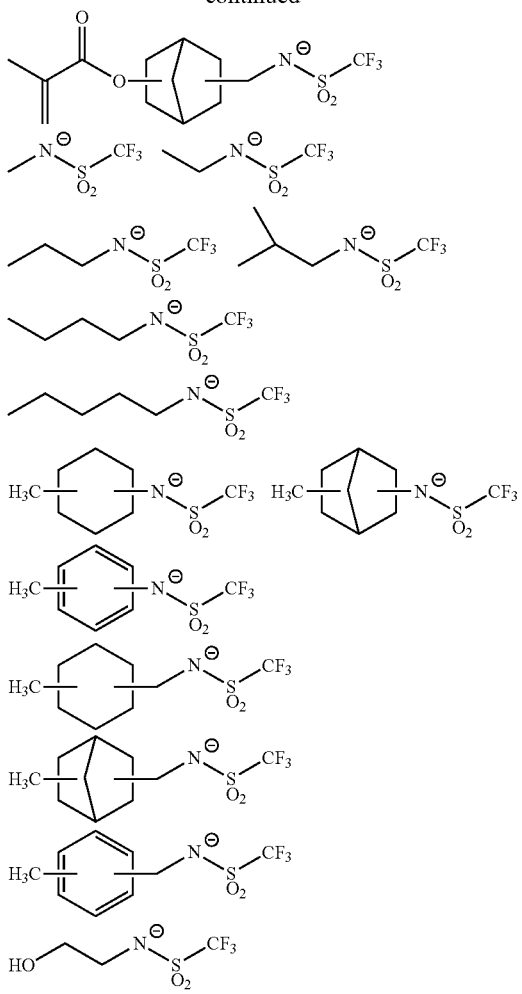

Cation Part

In the formula (d2-3), $M^{m+}$ is an m-valent organic cation, and is the same as $M^{m+}$ in the formula (d2-2).

The (d2-3) component may be used alone, and two or more types thereof may be used in combination.

In the resist composition of the present aspect, the (D21) component may be obtained by using the (d2-2) component or the (d2-3) component, or using two or more types of components in combination.

In a case where the resist composition contains the (D21) component, the content of the (D21) component is preferably 0.5 to 10 parts by mass, further preferably 0.5 to 8 parts by mass, and still further preferably 1 to 8 parts by mass, with respect to 100 parts by mass of the (A) component.

When the (D21) component is equal to or greater than the preferred lower limit, it is easy to obtain particularly preferable lithography properties and resist pattern shape. On the other hand, when the (D21) component is equal to or lower than the upper limit, it is possible to maintain the excellent sensitivity and to obtain excellent throughput.

Method for Preparing (D21) Component:

The method for preparing the (d2-2) component is not particularly limited, and it can be prepared according to the conventional well-known methods.

In addition, the method for preparing the (d2-3) component is not particularly limited, and for example, the method disclosed in US 2012-0149916 can be used.

Regarding (D22) Component

The (D22) component is not particularly limited, and may be optionally used from the well-known components as long as it acts as the acid diffusion control agent and is other than the compounds corresponding to the (D1) component and the (D21) component. Among them, an aliphatic amine is preferable, and particularly, a secondary aliphatic amine and a tertiary aliphatic amine are further preferable.

The aliphatic amine means an amine having one or more aliphatic groups, and the number of carbon atoms of the aliphatic group is preferably 1 to 12.

Examples of the aliphatic amine include an amine (an alkyl amine or an alkyl alcohol amine) in which at least one hydrogen atom of ammonia $NH_3$ is substituted with an alkyl group or a hydroxyalkyl group having 12 carbon atoms or less, or a cyclic amine.

Specific examples of the alkyl amine and the alkyl alcohol amine include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamine such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, and tri-n-dodecylamine; and alkyl alcohol amine such as diethanolamine, triethanolamine, diisopropanolamine, triisopropanolamine, di-n-octanolamine, and tri-n-octanolamine. Among them, trialkylamine having 5 to 10 carbon atoms is further preferable, and tri-n-pentylamine or tri-n-octylamine is particularly preferable.

Examples of the cyclic amine include a heterocyclic compound containing a nitrogen atom as a heteroatom. The heterocyclic compound may be a monocyclic compound (aliphatic monocyclic amine) or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonen, 1,8-diazabicyclo[5.4.0]-7-undecene, hexamethylenetetramine, and 1,4-diazabicyclo[2.2.2] octane.

Examples of other aliphatic amines include tris(2-methoxymethoxyethyl) amine, tris{2-(2-methoxyethoxy) ethyl} amine, tris{2-(2-methoxyethoxymethoxy) ethyl} amine, tris{2-(1-methoxyethoxy) ethyl} amine, tris{2-(1-ethoxyethoxy) ethyl} amine, tris{2-(1-ethoxypropoxy) ethyl} amine, tris[2-{2-(2-hydroxyethoxy) ethoxy} ethyl] amine, and triethanolamine triacetate. Among them, triethanolamine triacetate is preferable.

In addition, aromatic amine may be used as the (D22) component.

Examples of the aromatic amine include 4-dimethyl aminopyridine, pyrrole, indole, pyrazole, imidazole, and derivatives thereof, tribenzylamine, 2,6-diisopropylaniline, and N-tert-butoxycarbonylpyrrolidine.

In the resist composition of the present aspect, the (D22) component may be used alone, or two or more types thereof may be used in combination.

In a case where the resist composition contains the (D22) component, the content of the (D22) component is generally 0.01 to 5 parts by mass with respect to 100 parts by mass of the (A) component. When the content is within the above range, the resist pattern shape, the post exposure stability, and the like are improved.

Other Components

The resist composition of the present aspect may further contain other components (optional components) in addition to the (A) component and (D) component.

Examples of the optional components include a (B) component, an (E) component, an (F) component, and an (S) component as described below.

(B) Component: Acid Generator Component

The resist composition of the present aspect may further contain an acid generator component (B) (here, the compound (D1) and the compound (D2) are excluded) which generates an acid upon exposure, in addition to the (A) component.

The (B) component is not particularly limited, and examples thereof include components proposed as an acid generator for chemically amplified resist compositions so far.

Examples of such an acid generator include various types of acid generators such as an onium salt-based acid generator such as an iodonium salt and a sulfonium salt, an oxime sulfonate-based acid generator; bisalkyl or bisaryl sulfonyl diazomethanes, a diazomethane-based acid generator such as poly (bissulfonyl) diazomethane; a nitrobenzylsulfonate-based acid generator, an iminosulfonate-based acid generator, and a disulfone-based acid generator. Among them, the onium salt-based acid generator is preferably used.

Examples of the onium salt-based acid generator include a compound (hereinafter, also referred to as a "(b-1) component") represented by the following general formula (b-1), a compound (hereinafter, also referred to as a "(b-2) component") represented by following general formula (b-2), or a compound (hereinafter, also referred to as a "(b-3) component") represented by following general formula (b-3).

[Chemical formula 56]

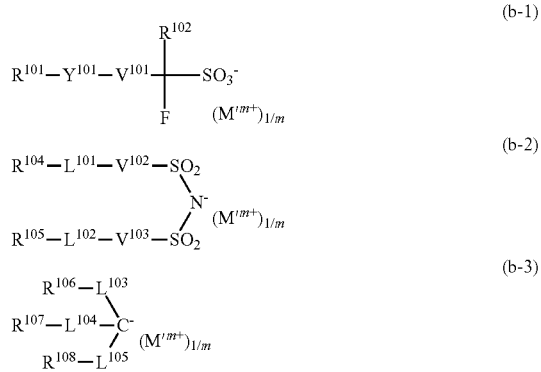

[In the formulae, $R^{101}$, $R^{104}$ to $R^{108}$ each independently represent a cyclic group which may have a substituent, a chain-like alkyl group which may have a substituent, or a chain-like alkenyl group which may have a substituent. $R^{104}$ and $R^{105}$ may be bonded to each other so as to form a ring.

$R^{102}$ is a fluorine atom or a fluorinated alkyl group having 1 to 5 carbon atoms. $Y^{101}$ is a divalent linking group containing a single bond or an oxygen atom. $V^{101}$ to $V^{103}$ each independently represent a single bond, an alkylene group, or a fluorinated alkylene group. $L^{101}$ and $L^{102}$ each independently represent a single bond or an oxygen atom. $L^{103}$ to $L^{105}$ each independently represent a single bond, —CO— or —SO$_2$—. m is an integer of 1 or more, and $M^{m+}$ is an m-valent onium cation.]

Anion Part

Anion Part of (b-1) Component

In the formula (b-1), $R^{101}$ is a cyclic group which may have a substituent, a chain-like alkyl group which may have a substituent, or a chain-like alkenyl group which may have a substituent, which is the same as a cyclic group which may have a substituent, a chain-like alkyl group which may have a substituent, or a chain-like alkenyl group which may have a substituent of $Rd^1$ in the formula (d1).

Among them, $R^{101}$ is preferably the cyclic group which may have a substituent, and further preferably the cyclic hydrocarbon group which may have a substituent. More specific examples thereof include a phenyl group, a naphthyl group, and a group obtained by removing one hydrogen atom from polycycloalkane; lactone-containing cyclic groups represented by the general formulae (a2-r-1), and (a2-r-3) to (a2-r-7); and —SO$_2$— containing cyclic groups represented by the general formulae (a5-r-1) to (a5-r-4).

In the formula (b-1), $Y^{101}$ is a divalent linking group containing a single bond or an oxygen atom.

In a case where $Y^{101}$ is a divalent linking group containing an oxygen atom, $Y^{101}$ may contain atoms other than the oxygen atom. Examples of the atoms other than the oxygen atom include a carbon atom, a hydrogen atom, a sulfur atom, and a nitrogen atom.

Examples of the divalent linking group containing an oxygen atom include a non-hydrocarbon-based oxygen atom-containing linking group such as an oxygen atom (ether bond: —O—), an ester bond (—C(=O)—O—), an oxycarbonyl group (—O—C(=O)—), an amide bond (—C(=O)—NH—), a carbonyl group (—C(=O)—), and a carbonate bond (—O—C(=O)—O—); and a combination of the non-hydrocarbon-based oxygen atom-containing linking group with an alkylene group. A sulfonyl group (—SO$_2$—) may be further linked to the aforementioned combination. Examples of the divalent linking group containing an oxygen atom include linking groups represented by the following general formulae (y-al-1) to (y-al-7).

[Chemical formula 57]

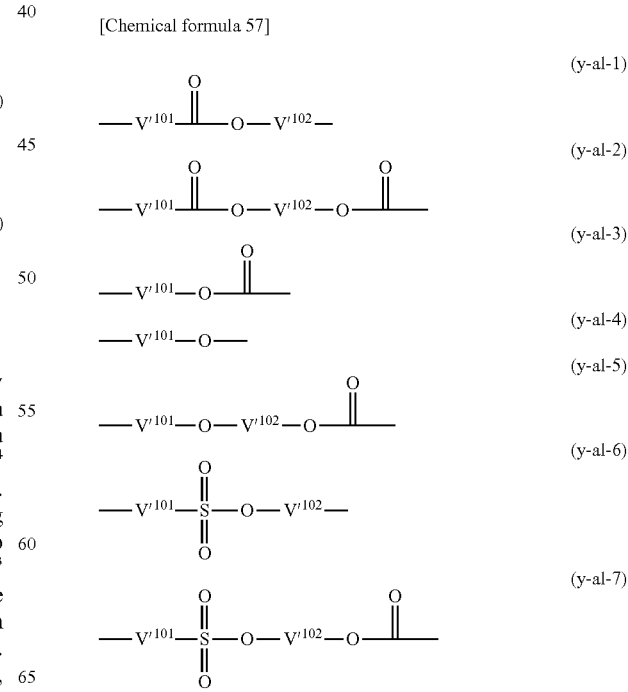

[In the formulae, $V'^{101}$ is a single bond or an alkylene group having 1 to 5 carbon atoms, and $V'^{102}$ is divalent saturated hydrocarbon group having 1 to 30 carbon atoms.]

The divalent saturated hydrocarbon group for $V'^{102}$ is preferably an alkylene group having 1 to 30 carbon atoms, is further preferably an alkylene group having 1 to 10 carbon atoms, and is still further preferably an alkylene group having 1 to 5 carbon atoms.

The alkylene group for $V'^{101}$ and $V'^{102}$ may be a linear alkylene group or a branched alkylene group, and is preferably a linear alkylene group.

Specific examples of the alkylene group for $V'^{101}$ and $V'^{102}$ include a methylene group [—$CH_2$—]; an alkyl methylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; an ethylene group [—$CH_2CH_2$—]; an alkyl ethylene group such as —$CH(CH_3)CH_2$—, —$CH(CH_3)CH(CH_3)$—, —$C(CH_3)_2CH_2$—, and —$CH(CH_2CH_3)CH_2$—; a trimethylene group (an n-propylene group) [—$CH_2CH_2CH_2$—]; alkyl trimethylene group such as —$CH(CH_3)CH_2CH_2$—, and —$CH_2CH(CH_3)CH_2$—; a tetramethylene group [—$CH_2CH_2CH_2CH_2$—]; an alkyl tetramethylene group such as —$CH(CH_3)CH_2CH_2CH_2$— and —$CH_2CH(CH_3)CH_2CH_2$—; and a pentamethylene group [—$CH_2CH_2CH_2CH_2CH_2$—].

Further, at least one of the methylene groups included in the alkylene group for $V'^{101}$ or $V'^{102}$ may be substituted with a divalent aliphatic cyclic group having 5 to 10 carbon atoms. The aliphatic cyclic group is preferably a divalent group obtained by further removing one hydrogen atom from a cyclic aliphatic hydrocarbon group (a monocyclic aliphatic hydrocarbon group and a polycyclic aliphatic hydrocarbon group) of $Ra'^3$ in the formula (a1-r-1), and is further preferably a cyclohexylene group, a 1,5-adamantylene group, or a 2,6-adamantylene group.

As $Y^{101}$, a divalent linking group containing an ester bond, or a divalent linking group containing an ether bond is preferable, and linking groups represented by the general formulae (y-al-1) to (y-al-5) are further preferable.

In the formula (b-1), $V^{101}$ is a single bond, an alkylene group, or a fluorinated alkylene group. The alkylene group and the fluorinated alkylene group for $V^{101}$ preferably have 1 to 4 carbon atoms. Examples of the fluorinated alkylene group for $V^{101}$ include a group in which at least one or all of the hydrogen atoms of the alkylene group for $V^{101}$ is substituted with a fluorine atom. Among them, $V^{101}$ is preferably a single bond or a fluorinated alkylene group having 1 to 4 carbon atoms.

In the formula (b-1), R is a fluorine atom or a fluorinated alkyl group having 1 to 5 carbon atoms. $R^{102}$ is preferably a fluorine atom or a perfluoroalkyl group having 1 to 5 carbon atoms, and further preferably a fluorine atom.

Specific examples of the anion part of the (b-1) component include a fluorinated alkyl sulfonate anion such as trifluoromethanesulfonate anion and perfluorobutanesulfonate anion in a case where $Y^{101}$ is a single bond; and the anion represented by any one of the following formulae (an-1) to (an-3) in a case where $Y^{101}$ is a divalent linking group containing an oxygen atom.

[Chemical formula 58]

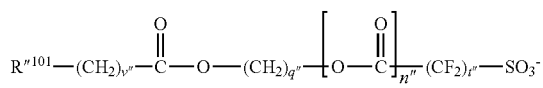
(an-1)

-continued

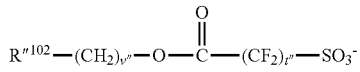
(an-2)

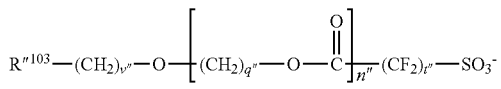
(an-3)

[In the formula, $R'''^{101}$ is an aliphatic cyclic group which may have a substituent, groups represented by the formulae (r-hr-1) to (r-hr-6), or a chain-like alkyl group which may have a substituent; $R'''^{102}$ is an aliphatic cyclic group which may have a substituent, a lactone-containing cyclic group represented by the general formulae (a2-r-1), (a2-r-3) to (a2-r-7), or a —$SO_2$— containing cyclic group represented by the general formulae (a5-r-1) to (a5-r-4); $R'''^{103}$ is an aromatic cyclic group which may have a substituent, an aliphatic cyclic group which may have a substituent, or a chain-like alkenyl group which may have a substituent; $v'''$s are each independently an integer of 0 to 3, $q'''$s are each independently an integer of 1 to 20, $t'''$s are each independently an integer of 1 to 3, and $n''$ is an integer of 0 or 1.]

The aliphatic cyclic groups which may have a substituent for $R'''^{101}$, $R'''^{102}$, and $R'''^{103}$ are preferably those exemplified as the cyclic aliphatic hydrocarbon group for $Rd^1$ in the formula (d1). Examples of the substituents include the same as those which the cyclic aliphatic hydrocarbon group for $Rd^1$ in the formula (d1) may have as a substituent.

The aromatic cyclic group which may have a substituent for $R'''^{103}$ is preferably those exemplified as an aromatic hydrocarbon group of a cyclic hydrocarbon group for $Rd^1$ in the formula (d1). Examples of the substituent include the same as those which the aromatic hydrocarbon group for $Rd^1$ in the formula (d1) may have as a substituent.

The chain-like alkyl group which may have a substituent for $R'''^{101}$ is preferably the groups exemplified as the chain-like alkyl group for $Rd^1$ in the formula (d1). Preferred examples of the chain-like alkenyl group which may have a substituent for $R'''^{103}$ include the groups exemplified as the chain-like alkenyl group of $Rd^1$ in the formula (d1).

Anion Part of (b-2) Component

In the formula (b-2), $R^{104}$ and $R^{105}$ each independently represent a cyclic group which may have a substituent, a chain-like alkyl group which may have a substituent, or a chain-like alkenyl group which may have a substituent, which is the same as a cyclic group which may have a substituent, a chain-like alkyl group which may have a substituent, or a chain-like alkenyl group which may have a substituent for $Rd^1$ in the formula (d1). Here, $R^{104}$ and $R^{105}$ may be bonded to each other so as to form a ring.

$R^{104}$ and $R^{105}$ are preferably a chain-like alkyl group which may have a substituent, and are further preferably a linear or branched alkyl group, or a linear or branched fluorinated alkyl group.

The number of the carbon atoms of the chain-like alkyl group is preferably 1 to 10, further preferably 1 to 7, and still further preferably 1 to 3. The number of the carbon atoms of the chain-like alkyl group of $R^{104}$ and $R^{105}$ is preferably as small as possible within the range of the carbon number from the aspect that the solubility with respect to the resist solvent is improved. In the chain-like alkyl group for $R^{104}$ and $R^{105}$, the large number of the hydrogen atoms which are substituted with a fluorine atom is preferable from the aspect that the strength of the acid becomes stronger and transparency to high energy light of 200 nm or less or an electron beam is improved.

The ratio of a fluorine atom in the chain-like alkyl group, that is, a fluorination rate is preferably 70% to 100%, and further preferably 90% to 100%, and a perfluoroalkyl group in which all hydrogen atoms are substituted with fluorine atoms is most preferable.

In the formula (b-2), $V^{102}$ and $V^{103}$ each independently represent a single bond, an alkylene group, or a fluorinated alkylene group, which are the same as those for $V^{101}$ in the formula (b-1).

In the formula (b-2), $L^{101}$ and $L^{102}$ each independently represent a single bond or an oxygen atom.

Anion Part of (b-3) Component

In the formula (b-3), $R^{106}$ to $R^{108}$ each independently represent a cyclic group which may have a substituent, a chain-like alkyl group which may have a substituent, or a chain-like alkenyl group which may have a substituent, which is the same as the cyclic group which may have a substituent, the chain-like alkyl group which may have a substituent, or the chain-like alkenyl group which may have a substituent for $Rd^1$ in the formula (d1).

$L^{103}$ to $L^{105}$ each independently represent a single bond, —CO—, or —SO$_2$—.

Cation Part

In the formulae (b-1), (b-2), and (b-3), m is an integer of 1 or more, $M'^{m+}$ is an m-valent onium cation, and preferred examples thereof include a sulfonium cation and an iodonium cation. Specific examples thereof include organic cations represented by the general formulae (ca-1) to (ca-4).

Preferred examples of the cation represented by the formula (ca-1) include the cations represented by the formulae (ca-1-1) to (ca-1-67).

Preferred examples of the cation represented by the formula (ca-2) include a diphenyliodonium cation and a bis(4-tert-butylphenyl) iodonium cation.

Preferred examples of the cation represented by the formula (ca-3) include the cations represented by the formulae (ca-3-1) to (ca-3-6).

Preferred examples of the cation represented by the formula (ca-4) include the cations represented by the formulae (ca-4-1) and (ca-4-2).

Among them, the cation part $[(M'^{m+})_{1/m}]$ is preferably a cation represented by general formula (ca-1), and is further preferably cations represented by the formulae (ca-1-1) to (ca-1-67).

In the resist composition of the present aspect, the (B) component may be used alone, or two or more types thereof may be used in combination.

In a case where the resist composition contains the (B) component, the content of the (B) component in the resist composition is preferably 0.5 to 60 parts by mass, further preferably 1 to 50 parts by mass, and still further preferably 1 to 40 parts by mass with respect to 100 parts by mass of the (A) component.

When the content of the (B) component is set in the range, it is sufficient to form a pattern, and when the respective components of the resist composition are dissolved in an organic solvent, it is easy to obtain a uniform solution, whereby the storage stability of the component as a resist composition is improved, and thus the content is preferably in the above-described range.

(E) Component: At Least One Compound Selected from the Group Consisting of an Organic Carboxylic Acid and an Oxo Acid of Phosphorus, and Derivatives Thereof In the resist composition of the present aspect, in order to prevent the sensitivity from being deteriorated and to improve the resist pattern shape and the stability after coating, at least one compound (E) (hereinafter, referred to as "(E) component") selected from the group consisting of an organic carboxylic acid and an oxo acid of phosphorus, and derivatives thereof can be contained as an optional component.

As the organic carboxylic acid, for example, an acetic acid, a malonic acid, a citric acid, a malic acid, a succinic acid, a benzoic acid, and a salicylic acid are preferable.

Examples of the oxo acid of phosphorus include phosphoric acid, phosphonic acid, and phosphinic acid, and among them, phosphonic acid is particularly preferable.

Examples of the derivative of the oxo acid of phosphorus include ester obtained by substituting the hydrogen atom of the oxo acid with a hydrocarbon group, and examples of the hydrocarbon group include an alkyl group having 1 to 5 carbon atoms, and an aryl group having 6 to 15 carbon atoms.

Examples of the derivative of the phosphoric acid include phosphate ester such as phosphoric acid di-n-butyl ester and phosphoric acid diphenyl ester.

Examples of the derivative of the phosphonic acid include phosphonic acid ester such as phosphonic acid dimethyl ester, phosphonic acid-di-n-butyl ester, phenyl phosphonic acid, phosphonic acid diphenyl ester, and phosphonic acid dibenzyl ester.

Examples of the derivative of the phosphinic acid include phosphinic acid ester and a phenyl phosphinic acid.

In the resist composition of the present aspect, the (E) component may be used alone, or two or more types thereof may be used in combination.

In a case where the resist composition contains the (E) component, the content of the (E) component in the resist composition is generally 0.01 to 5 parts by mass with respect to 100 parts by mass of the (A) component.

(F) Component: Fluorine Additive Component

The resist composition of the present aspect may contain a fluorine additive component (hereinafter, referred to as "(F) component") so as to impart water repellency to the resist film.

Examples of the (F) component include fluorine-containing polymer compounds which are disclosed in Japanese Unexamined Patent Application, Publication No. 2010-002870, disclosed in Japanese Unexamined Patent Application, Publication No. 2010-032994, disclosed in Japanese Unexamined Patent Application, Publication No. 2010-277043, disclosed in Japanese Unexamined Patent Application, Publication No. 2011-13569, disclosed in Japanese Unexamined Patent Application, Publication No. 2011-128226.

Specific examples of the (F) component include a polymer having a structural unit (f1) represented by the following formula (f1-1). Preferred examples of the polymer include a polymer (homopolymer) consisting of a structural unit (f1) represented by the following formula (f1-1); a copolymer of the structural unit (f1) and the structural unit (a1); and a copolymer of the structural unit (f1), a structural unit derived from an acrylic acid or a methacrylic acid, and the structural unit (a1). Here, the structural unit (a1) which is copolymerized with the structural unit (f1) is preferably a structural unit derived from 1-ethyl-1-cyclooctyl (meth)acrylate, and a structural unit derived from 1-methyl-1-adamantyl (meth)acrylate.

[Chemical formula 59]

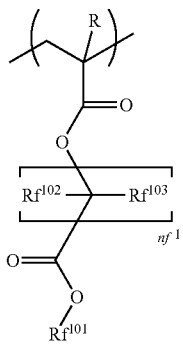

(f1-1)

[In the formula, R is the same as described above, $Rf^{102}$ and $Rf^{103}$ each independently represent a hydrogen atom, a halogen atom, an alkyl group having 1 to 5 carbon atoms, or a halogenated alkyl group having 1 to 5 carbon atoms, $Rf^{102}$ and $Rf^{103}$ may be the same as or different from each other. $nf^1$ is an integer of 1 to 5, $Rf^{101}$ is an organic group containing a fluorine atom.]

In the formula (f1-1), R which is bonded to an α-position carbon atom is the same as described above. R is preferably a hydrogen atom or a methyl group.

In the formula (f1-1), examples of the halogen atom of $Rf^{102}$ and $Rf^{103}$ include a fluorine atom, a chlorine atom, a bromine atom, and an iodine atom, and among them, the fluorine atom is particularly preferable. The alkyl group having 1 to 5 carbon atoms for $Rf^{102}$ and $Rf^{103}$ is the same as the alkyl group having 1 to 5 carbon atoms for R, and is preferably a methyl group or an ethyl group. Specific examples of the halogenated alkyl group having 1 to 5 carbon atoms for $Rf^{102}$ and $Rf^{103}$ include a group in which at least one or all of the hydrogen atoms of an alkyl group having 1 to 5 carbon atoms is substituted with a halogen atom.

Examples of the halogen atom include a fluorine atom, a chlorine atom, a bromine atom, and an iodine atom, and the fluorine atom is particularly preferable. Among them, as $Rf^{102}$ and $Rf^{103}$, a hydrogen atom, a fluorine atom, or an alkyl group having 1 to 5 carbon atoms is preferable, and a hydrogen atom, a fluorine atom, a methyl group, or an ethyl group is further preferable.

In the formula (f1-1), $nf^1$ is an integer of 1 to 5, preferably an integer of 1 to 3, and further preferably an integer of 1 or 2.

In the formula (f1-1), $Rf^{101}$ is an organic group containing a fluorine atom, and is preferably a hydrocarbon group containing a fluorine atom.

The hydrocarbon group containing a fluorine atom may be a linear, branched, or cyclic hydrocarbon group, and the number of carbon atoms of the hydrocarbon group is preferably 1 to 20, further preferably 1 to 15, and particularly preferably 1 to 10.

Further, in the hydrocarbon group containing a fluorine atom, 25% or more of hydrogen atoms in the hydrocarbon group is preferably fluorinated, 50% or more of hydrogen atoms is further preferably fluorinated, and 60% or more of hydrogen atoms is particularly preferably fluorinated from the aspect that the hydrophobicity of the resist film at the time of immersion exposure is enhanced.

Among them, as $Rf^{101}$, a fluorinated hydrocarbon group having 1 to 5 carbon atoms is further preferable, and a trifluoromethyl group, $-CH_2-CF_3$, $-CH_2-CF_2-CF_3$, $-CH(CF_3)_2$, $-CH_2-CH_2-CF_3$, and $-CH_2-CH_2-CF_2-CF_2-CF_2-CF_3$ are particularly preferable.

The mass average molecular weight (Mw) (in terms of the standard polystyrene by gel permeation chromatography) of the (F) component is preferably 1,000 to 50,000, further preferably 5,000 to 40,000, and most preferably 10,000 to 30,000. When the mass average molecular weight is equal to or less than the upper limit of the aforementioned range, the solubility in a resist solvent is sufficient in a case where the (F) component is used as a resist, and when the mass average molecular weight of the (F) component is equal to or greater than the lower limit of the aforementioned range, dry etching resistance and a resist pattern cross-sectional shape are improved.

The dispersivity (Mw/Mn) of the (F) component is preferably 1.0 to 5.0, further preferably 1.0 to 3.0, and most preferably 1.2 to 2.5.

In the resist composition of the present aspect, the (F) component may be used alone, or two or more types thereof may be used in combination.

In a case where the resist composition contains the (F) component, the content of the (F) component in the resist composition is generally 0.5 to 10 parts by mass with respect to 100 parts by mass of the (A) component.

(S) Component: Organic Solvent Component

The resist composition of the present aspect can be prepared by dissolving a resist material into an organic solvent component (hereinafter, referred to as "(S) component").

The (S) component may be a component which can form a homogeneous solution by dissolving the respective components to be used, and any one of well-known conventional solvents for the chemically amplified resist composition is properly selected as the (S) component.

Examples of the (S) component include lactones such as γ-butyrolactone; ketones such as acetone, methyl ethyl ketone, cyclohexanone, methyl-n-pentyl ketone, methyl isopentyl ketone, and 2-heptanone; polyhydric alcohols such as ethylene glycol, diethylene glycol, propylene glycol, and dipropylene glycol; derivatives of polyhydric alcohols such as a compound having an ester bond such as ethylene glycol monoacetate, diethylene glycol monoacetate, propylene glycol monoacetate, or dipropylene glycol monoacetate, and a compound having an ether bond such as monoalkyl ether or monophenyl ether such as monomethyl ether, monoethyl ether, monopropyl ether, and monobutyl ether of the compound having the polyhydric alcohol or the ester bond [among them, propylene glycol monomethyl ether acetate (PGMEA), and propylene glycol monomethyl ether (PGME), are preferable]; cyclic ethers such as dioxane, esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethyl benzyl ether, cresyl methyl ether, diphenyl ether, dibenzyl ether, phenetole, butyl phenyl ether, ethyl benzene, diethyl benzene, pentyl benzene, isopropyl benzene, toluene, xylene, cymene, and mesitylene; and dimethyl sulfoxide (DMSO).

In the resist composition of the present aspect, the (S) component may be used alone or may be used as a mixed solvent of two or more types thereof.

Among them, PGMEA, PGME, γ-butyrolactone, EL, and cyclohexanone are preferable.

In addition, a mixed solvent obtained by mixing PGMEA and a polar solvent is also preferable. The mixing ratio (mass ratio) may be properly determined in consideration of the compatibility of the PGMEA with the polar solvent, and the ratio is preferably 1:9 to 9:1, and further preferably 2:8 to 8:2.

More specifically, in a case of mixing EL or cyclohexane as the polar solvent, the mass ratio of PGMEA to EL or cyclohexane is preferably 1:9 to 9:1, and further preferably 2:8 to 8:2. In addition, in a case of using PGME as a polar solvent, the mass ratio of PGMEA to PGME is preferably 1:9 to 9:1, further preferably 2:8 to 8:2, and still further preferably 3:7 to 7:3. In addition, a mixed solvent obtained by mixing PGMEA, PGME, and cyclohexane is also preferable.

Further, as the (S) component, a mixed solvent obtained by mixing at least one selected from PGMEA and EL with γ-butyrolactone is also preferable. In this case, as the mixing ratio, the mass ratio of the former to the latter is preferably set to be 70:30 to 95:5.

The content of the (S) component used is not particularly limited, and is properly set so as to provide a concentration such that coating on a substrate or the like can be performed depending on the thickness of the coated film. Generally, the (S) component is used such that the concentration of solid contents of the resist composition is 1 to 20% by mass, and preferably 2 to 15% by mass.

It is possible to incorporate a miscible additive into the resist composition of the present aspect as necessary, and for example, an additional resin for improving the performance of the resist film, a dissolution inhibitor, a plasticizer, a stabilizer, a colorant, a halation inhibitor, and a dye can be added and incorporated.

As described above, the resist composition of the present aspect contains a polymer compound (A1) having a structural unit (a0) represented by general formula (a0-1), and thus it is possible to reduce the roughness and improve other lithography properties in the forming of the resist pattern. In addition, the resist composition contains the compound (D1) whose an conjugate acid has an acid dissociation constant (pKa) of less than 3 as an acid diffusion control agent, along with the (A1) component, and thus the excellent exposure stability is obtained, the contrast between the exposed area and the unexposed area of the resist film is easily obtained in the forming of the resist pattern, and the occurrence of defects is suppressed.

Method for Forming Resist Pattern

A method for forming a resist pattern according to the second aspect of the present invention includes a step of forming a resist film on a support by using the resist composition according to the first aspect, a step of exposing the resist film, and a step of developing the exposed resist film to form a resist pattern.

The method for forming a resist pattern of the present aspect can be performed in the following manner.

First, the support is coated with the resist composition according to the first aspect by using a spinner, and the coated film is subjected to a bake (Post Applied Bake (PAB)) treatment at a temperature of 80° C. to 150° C. for 40 to 120 seconds (preferably for 60 to 90 seconds) so as to form a resist film.

Then, the resist film is exposed via a mask (a mask pattern) on which a predetermined pattern is formed, or is selectively exposed without the mask pattern by drawing or the like due to direct irradiation of an electron beam by using an exposure apparatus such as an ArF exposure apparatus, an electron beam drawing apparatus, and an EUV exposure apparatus, and then is subjected to a bake (Post Exposure Bake (PEB)) treatment at a temperature of 80° C. to 150° C. for 40 to 120 seconds (preferably for 60 to 90 seconds).

Subsequently, the resist film is subjected to the developing treatment. In the developing treatment, an alkali developing solution is used in a case of the alkali developing process, and a developing solution (organic developing solution) containing an organic solvent is used in a case of the solvent developing process.

After the developing treatment, a rinse treatment is preferably performed. In the rinse treatment, water rinsing is preferably performed by using pure water in a case of the alkali developing process, and a rinsing liquid containing an organic solvent is preferably used in a case of the solvent developing process.

In the case of the solvent developing process, a treatment of removing the developing solution or the rinsing liquid which is attached on the pattern by a supercritical fluid may be performed after the developing treatment and the rinse treatment.

Drying is performed after the developing treatment and the rinse treatment. In addition, in some cases, a bake (post bake) treatment may be performed after the developing treatment.

In this way, it is possible to form a resist pattern.

The support is not particularly limited, and it is possible to use conventionally well-known supports. Examples thereof include a substrate for electronic parts and a substrate on which a prescribed wiring pattern is formed. More specifically, examples of the support include a metallic substrate such as a silicon wafer, copper, chromium, iron, and aluminum, and a glass substrate. As the wire pattern material, for example, it is possible to use copper, aluminum, nickel, and gold.

In addition, a support obtained by providing an inorganic and/or organic film on the substrate may be used as the support. Examples of the inorganic film include an inorganic antireflection film (inorganic BARC). Examples of the organic film include an organic antireflection film (organic BARC) or a lower layer organic film obtained by using a multilayer resist method.

Here, the multilayer resist method is a method of providing at least one layer of an organic film (lower layer organic film) and at least one layer of a resist film (upper layer resist film) on a substrate, and then patterning the lower layer organic film through the resist pattern formed in the upper layer resist film as a mask. With such a method, it is possible to form a pattern with a high aspect ratio. That is, according to the multilayer resist method, since the required thickness can be secured by the lower layer organic film, the resist film can be thinned and a fine pattern with the high aspect ratio can be formed.

The multilayer resist method basically includes a method (two-layer resist method) of setting a two-layer structure of an upper layer resist film and a lower layer organic film, and a method (three-layer resist method) of setting a multilayer (three or more layers) structure of providing one or more intermediate layers (thin metal film and the like) between the upper layer resist film and the lower layer organic film.

The wavelength for the exposure is not particularly limited, and radiations such as ArF excimer laser, KrF excimer laser, $F_2$ excimer laser, extreme ultraviolet rays (EUV), vacuum ultraviolet rays (VUV), electron beams (EB), X rays, and soft X rays may be used. The resist composition is highly useful when being used for KrF excimer laser, ArF excimer laser, EB or EUV, and is particularly useful when being used for ArF excimer laser, EB, or EUV.

As a method for exposing a resist film, a typical exposure (dry exposure) performed in an inert gas such as air or nitrogen, or liquid immersion lithography may be employed.

The liquid immersion lithography is an exposing method performed in such a manner that a space between a resist film and a lens at the lowermost position of an exposure apparatus is filled with a solvent (liquid immersion medium) having a refractive index larger than the refractive index of air in advance, and exposure (immersion exposure) is performed in that state.

The liquid immersion medium is preferably a solvent having a refractive index which is larger than refractive index of air, and is smaller than the refractive index of the resist film to be exposed. The refractive index of the solvent is not particularly limited as long as it is within the range.

Examples of the solvent having a refractive index, which is larger than refractive index of air and is smaller than the refractive index of the resist film, include water, a fluorinated inert liquid, a silicone solvent, and a hydrocarbon solvent.

Specific examples of the fluorinated inert liquid include a liquid having a fluorine compound as a main component, such as $C_3HCl_2F_5$, $C_4F_9OCH_3$, $C_4F_9OC_2H_5$, and $C_5H_3F_7$, and the boiling point thereof is preferably 70° C. to 180° C., and further preferably 80° C. to 160° C. When the fluorinated inert liquid has the boiling point within the above-described range, after completion of the exposure, the medium used for the liquid immersion can be removed by a simple method.

The fluorinated inert liquid is particularly preferably a perfluoroalkyl compound in which all hydrogen atoms of an alkyl group are substituted with fluorine atoms. Specific examples of the perfluoroalkyl compound include a perfluoroalkyl ether compound and a perfluoroalkylamine compound.

Further, specifically, examples of the perfluoroalkyl ether compound include perfluoro (2-butyl-tetrahydrofuran) (boiling point 102° C.), and examples of the perfluoroalkylamine compound include perfluorotributylamine (boiling point of 174° C.)

As the liquid immersion medium, water is preferably used in terms of cost, safety, environmental problems, and versatility.

Examples of an alkali developing solution used for the developing treatment in the alkali developing process include 0.1 to 10% by mass of tetramethyl ammonium hydroxide (TMAH) aqueous solution.

The organic solvent containing organic developing solution used for the developing treatment in the solvent developing process may be a solvent in which the (A) component ((A) component before exposure) can be dissolved, and can be appropriately selected from well-known organic solvents. Specific examples thereof include a polar solvent such as a ketone-based solvent, an ester-based solvent, an alcohol-based solvent, a nitrile-based solvent, an amide-based solvent, and an ether-based solvent, and a hydrocarbon solvent.

The ketone-based solvent is an organic solvent containing C—C(=O)—C in the structure. The ester-based solvent is an organic solvent containing C—C(=O)—O—C in the structure. The alcohol-based solvent is an organic solvent containing an alcoholic hydroxyl group in the structure. The "alcoholic hydroxyl group" means a hydroxyl group which is bonded to a carbon atom of an aliphatic hydrocarbon group. The nitrile-based solvent is an organic solvent containing a nitrile group in the structure. The amide-based solvent is an organic solvent containing an amide group in the structure. The ether-based solvent is an organic solvent containing C—O—C in the structure.

The organic solvent may contain various types of functional groups characterizing each classified solvent in the structure. In this case, the organic solvent is determined to correspond to plural organic solvents by being classified with respect to each of the functional groups that the organic solvent has. For example, diethylene glycol monomethyl ether corresponds to any one of the alcohol-based solvent and the ether-based solvent among the above-described solvent types.

The hydrocarbon solvent consists of hydrocarbons which may be halogenated, and does not contain a substituent except for a halogen atom. Examples of the halogen atom include a fluorine atom, a chlorine atom, a bromine atom, and an iodine atom, and among them, the fluorine atom is preferable.

Among the above examples, the organic solvent contained in an organic developing solution is preferably a polar solvent, and the ketone-based solvent, the ester-based solvent, and the nitrile-based solvent are preferable.

Examples of the ketone-based solvent include 1-octanone, 2-octanone, 1-nonanone, 2-nonanone, acetone, 4-heptanone, 1-hexanone, 2-hexanone, diisobutyl ketone, cyclohexanone, methyl cyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, propylene carbonate, γ-butyrolactone, and methyl amyl ketone (2-heptanone). Among them, the ketone-based solvent is preferably methyl amyl ketone (2-heptanone).

Examples of ester-based solvent include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate, and propyl-3-methoxypropionate. Among them, the ester-based solvent is preferably butyl acetate.

Examples of the nitrile-based solvent include acetonitrile, propionitrile, valeronitrile, and butyronitrile.

In organic developing solution, well-known additives can be mixed as necessary. Examples of the additives include a surfactant. The surfactant is not particularly limited, and examples thereof include an ionic or nonionic fluorine-based and/or silicon-based surfactant.

The surfactant is preferably a nonionic surfactant, and is further preferably a nonionic fluorine-based surfactant or a nonionic silicon-based surfactant.

In a case of mixing the surfactant, the mixing content is generally 0.001 to 5% by mass, preferably 0.005 to 2% by mass, and further preferably 0.01 to 0.5% by mass, with respect to the entire content of the organic developing solution.

The developing treatment can be implemented by using a well-known developing method, and examples thereof include a method of dipping the support into the developing solution for a certain period of time (a dipping method), a method of raising the developing solution on the surface of the support by surface tension and resting for a certain period of time (a puddle method), a method of spaying the developing solution on the surface of the support (a spray method), and a method of continuously coating a support which rotates at a constant speed with the developing solution while scanning a developing solution coating nozzle at a constant speed (a dynamic dispense method).

As the organic solvent contained in a rinsing liquid used in the rinse treatment after the developing treatment in the solvent developing process, an organic solvent in which a resist pattern is not easily dissolved can be used by appropriately selected from the organic solvents exemplified as the organic solvent used in the organic developing solution. Typically, at least one solvent selected from a hydrocarbon solvent, a ketone-based solvent, an ester-based solvent, an alcohol-based solvent, an amide-based solvent, and an ether-based solvent is used. Among them, at least one selected from the hydrocarbon solvent, the ketone-based solvent, the ester-based solvent, the alcohol-based solvent, and the amide-based solvent is preferably used, at least one selected from the alcohol-based solvent and the ester-based solvent is further preferably used, and the alcohol-based solvent is particularly preferable.

The alcohol-based solvent used in the rinsing liquid is preferably monohydric alcohol having 6 to 8 carbon atoms, and the monohydric alcohol may be linear, branched, or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol, and benzyl alcohol. Among them, 1-hexanol, 2-heptanol, and 2-hexanol are preferable, and 1-hexanol and 2-hexanol are further preferable.

These organic solvents may be used alone, or two or more types thereof may be used in combination. In addition, an organic solvent other than the above-described organic solvents or water may be used in the mixture. Here, when it comes to the developing properties, the mixing content of water in the rinsing liquid is preferably 30% by mass or less, is further preferably 10% by mass or less, is still further preferably 5% by mass or less, and is particularly preferably equal to or less than 3% by mass with respect to the total content of the rinsing liquid.

In the rinsing liquid, well-known additives can be mixed as necessary. Examples of the additives include a surfactant. Examples of the surfactant include the same surfactant as described above, and a nonionic surfactant is preferable, a nonionic fluorine-based surfactant or a nonionic silicon-based surfactant is further preferable.

In a case of mixing the surfactant, the mixing content is generally 0.001 to 5% by mass, preferably 0.005 to 2% by mass, and further preferably 0.01 to 0.5% by mass, with respect to the total content of the rinsing liquid.

The rinse treatment (washing treatment) using a rinsing liquid can be implemented by using a well-known rinsing method. Examples of a method of the rinse treatment include a method of continuously coating a support with the rinsing liquid which rotating the support at a constant speed (a rotary coating method), a method of dipping the support into the rinsing liquid (a dipping method) for a certain period of time, and a method of spraying the rinsing liquid to the surface of the support (a spray method).

According to the method for forming a resist pattern of the present aspect, when the resist composition according to the first aspect is used, the lithography properties can be improved, the occurrence of the defects is suppressed, and a finer pattern can be formed in a good shape.

EXAMPLES

Hereinafter, the present invention will be more specifically described with reference to examples; however, the invention is not limited thereto.

In the present examples, a compound represented by Chemical formula (1) is denoted as a "compound (1)", and the same is applicable to other compounds represented by other chemical formulae.

Preparation of Polymer Compound

A polymer compound (A1-1), a polymer compound (A1-2), a polymer compound (A2-1), and a polymer compound (A2-2) used in the present example were obtained by performing the radical polymerization of the following monomers providing structural units which constitute each of the aforementioned polymer compounds at a predetermined molar ratio.

[Chemical formula 60]

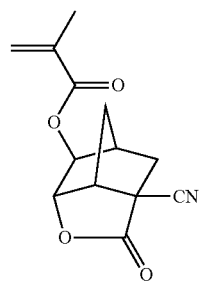

monomer (01)

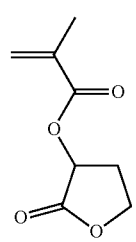

monomer (21)

monomer (22)

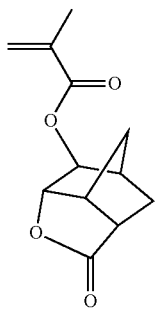

monomer (23)

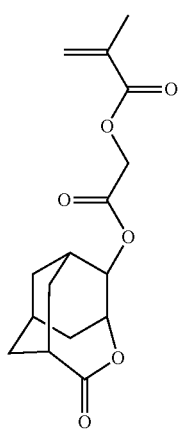

monomer (24)

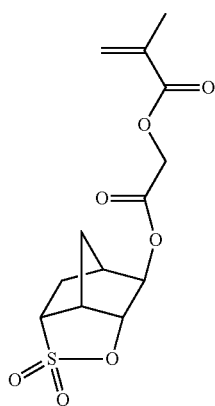

monomer (11)

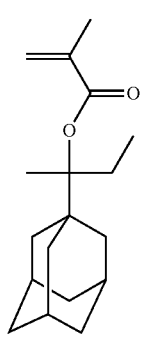

monomer (12)

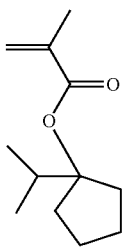

monomer (13)

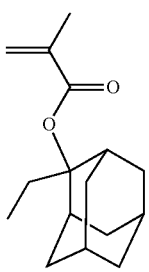

monomer (14)

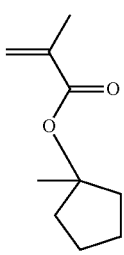

monomer (31)

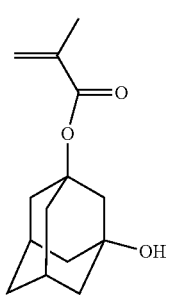

Regarding the obtained polymer compound (A1-1), polymer compound (A1-2), polymer compound (A2-1), and polymer compound (A2-2), the mass average molecular weight (Mw) and the molecular weight dispersivity (Mw/Mn) were obtained by GPC measurement (in terms of standard polystyrene).

In addition, regarding the obtained polymer compounds, the copolymer composition ratio (the ratio of each of the structural units (molar ratio) in the structural formula) was obtained by using carbon 13 nuclear magnetic resonance spectrum (600 MHz-$^{13}$C-NMR).

The obtained polymer compounds are shown below.

[Chemical formula 61]

Polymer compound (A1-1)

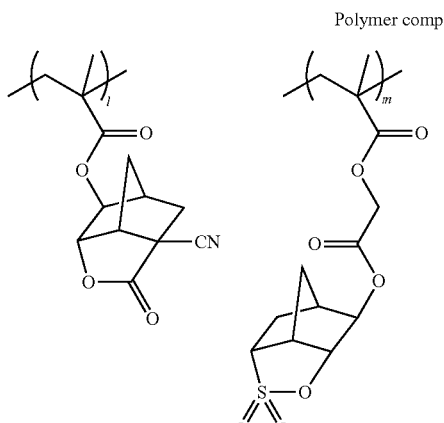

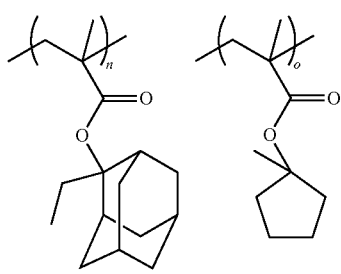

Polymer compound (A1-1): mass average molecular weight (Mw) of 9200, molecular weight dispersivity (Mw/Mn) of 1.55, l/m/n/o=40/10/10/40

[Chemical formula 62]

Polymer compound (A1-2)

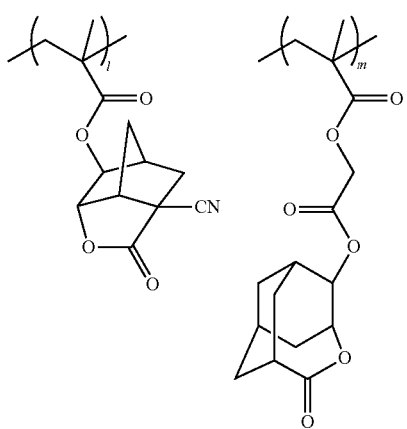

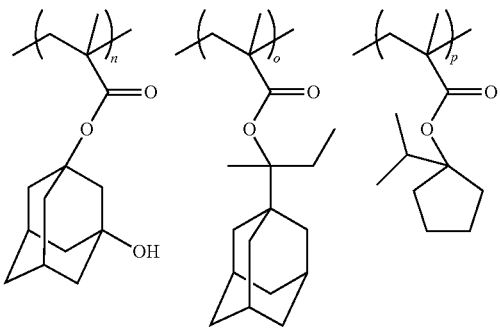

Polymer compound (A1-2): mass average molecular weight (Mw) of 8900, molecular weight dispersivity (Mw/Mn) of 1.61, l/m/n/o/p=30/20/10/10/30

[Chemical formula 63]

Polymer compound (A2-1)

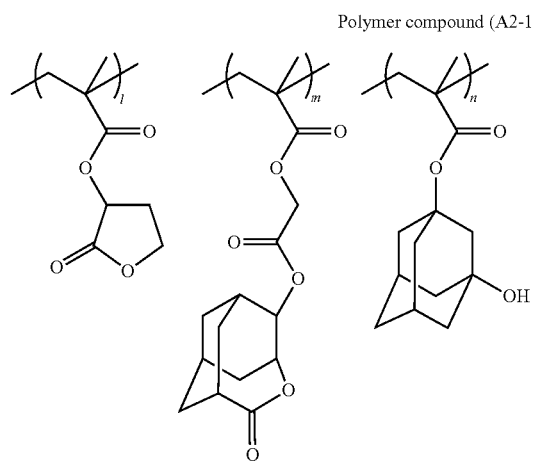

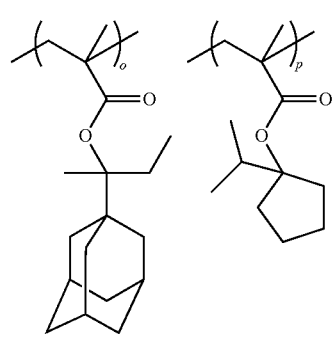

Polymer compound (A2-1): mass average molecular weight (Mw) of 8900, molecular weight dispersivity (Mw/Mn) of 1.61, l/m/n/o/p=30/20/10/10/30

[Chemical formula 64]

Polymer compound (A2-2)

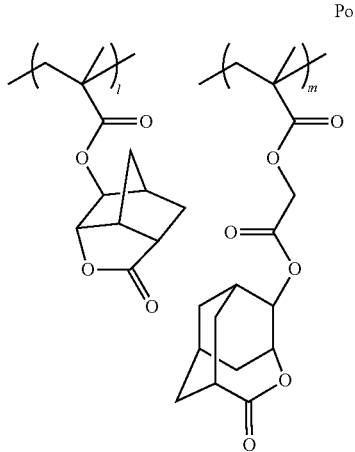

Polymer compound (A2-2): mass average molecular weight (Mw) of 9,000, molecular weight dispersivity (Mw/Mn) of 1.63, l/m/n/o/p=30/20/10/10/30

Preparation of Resist Composition

Examples 1 to 5, Comparative Examples 1 to 6

With respect to the each working example, the components indicated in Table 1 were mixed and dissolved to prepare a resist composition (concentration of solid contents: 3.0% by mass).

TABLE 1

|  | (A) component | | (D) component | | (B) component | (E) component | (F) component | (S) component | |
|---|---|---|---|---|---|---|---|---|---|
| Example 1 | (A1)-1 | — | (D1)-1 | — | (B)-1 | (E)-1 | (F)-1 | (S)-1 | (S)-2 |
|  | [100] |  | [3.66] |  | [10] | [1.5] | [3.0] | [100] | [4000] |
| Example 2 | (A1)-1 | — | (D1)-2 | — | (B)-1 | (E)-1 | (F)-1 | (S)-1 | (S)-2 |
|  | [100] |  | [4.13] |  | [10] | [1.5] | [3.0] | [100] | [4000] |
| Example 3 | (A1)-1 | — | (D1)-3 | — | (B)-1 | (E)-1 | (F)-1 | (S)-1 | (S)-2 |
|  | [100] |  | [4.09] |  | [10] | [1.5] | [3.0] | [100] | [4000] |
| Comparative Example 1 | (A1)-1 | — | — | (D2)-1 | (B)-1 | (E)-1 | (F)-1 | (S)-1 | (S)-2 |
|  | [100] |  |  | [3.50] | [10] | [1.5] | [3.0] | [100] | [4000] |
| Example 4 | (A1)-1 | — | (D1)-4 | — | (B)-1 | (E)-1 | (F)-1 | (S)-1 | (S)-2 |
|  | [100] |  | [4.16] |  | [10] | [1.5] | [3.0] | [100] | [4000] |
| Example 5 | (A1)-2 | — | (D1)-2 | — | (B)-1 | (E)-1 | (F)-1 | (S)-1 | (S)-2 |
|  | [100] |  | [4.13] |  | [10] | [1.5] | [3.0] | [100] | [4000] |
| Comparative Example 2 | — | (A2)-1 | (D1)-2 | — | (B)-1 | (E)-1 | (F)-1 | (S)-1 | (S)-2 |
|  |  | [100] | [4.13] |  | [10] | [1.5] | [3.0] | [100] | [4000] |
| Comparative Example 3 | — | (A2)-2 | (D1)-2 | — | (B)-1 | (E)-1 | (F)-1 | (S)-1 | (S)-2 |
|  |  | [100] | [4.13] |  | [10] | [1.5] | [3.0] | [100] | [4000] |
| Comparative Example 4 | (A1)-2 | — | — | (D2)-1 | (B)-1 | (E)-1 | (F)-1 | (S)-1 | (S)-2 |
|  | [100] |  |  | [3.50] | [10] | [1.5] | [3.0] | [100] | [4000] |
| Comparative Example 5 | — | (A2)-1 | — | (D2)-1 | (B)-1 | (E)-1 | (F)-1 | (S)-1 | (S)-2 |
|  |  | [100] |  | [3.50] | [10] | [1.5] | [3.0] | [100] | [4000] |
| Comparative Example 6 | — | (A2)-2 | — | (D2)-1 | (B)-1 | (E)-1 | (F)-1 | (S)-1 | (S)-2 |
|  |  | [100] |  | [3.50] | [10] | [1.5] | [3.0] | [100] | [4000] |

-continued

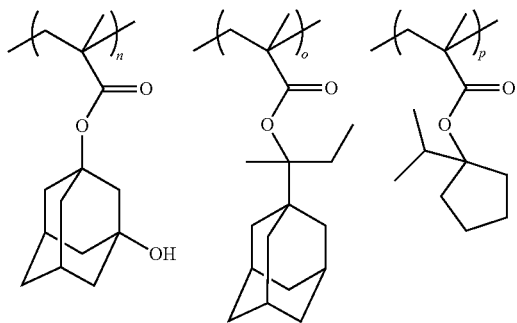

Each abbreviation in Table 1 has the following meaning. In addition, each numerical value in the brackets is the mixing content (parts by mass).
(A1)-1: the polymer compound (A1-1)
(A1)-2: the polymer compound (A1-2)
(A2)-1: the polymer compound (A2-1)
(A2)-2: the polymer compound (A2-2)
(D1)-1: a compound represented by the following Chemical formula (d1-11), whose conjugate acid has a pKa of 2.85
(D1)-2: a compound represented by the following Chemical formula (d1-12), whose conjugate acid has a pKa of 1.53
(D1)-3: a compound represented by the following Chemical formula (d1-13), whose conjugate acid has a pKa of 2.45 pKa
(D1)-4: a compound represented by the following Chemical formula (d1-14), whose conjugate acid has a pKa of 0.37

(D2)-1: a compound represented by Chemical formula (d2-11), whose conjugate acid has a pKa of 3.01

[Chemical formula 65]

(d1-11)

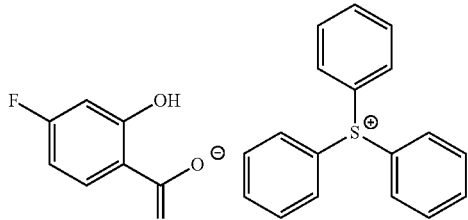

(d1-12)

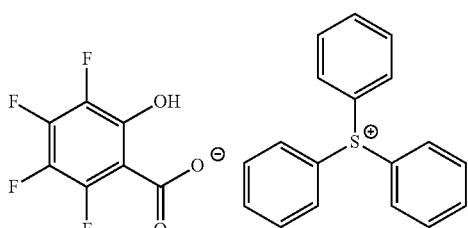

(d1-13)

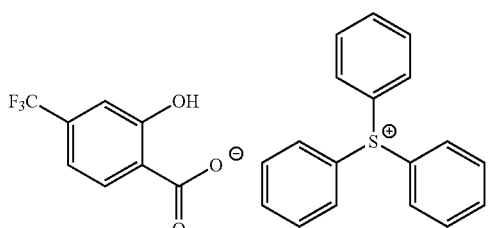

(d1-14)

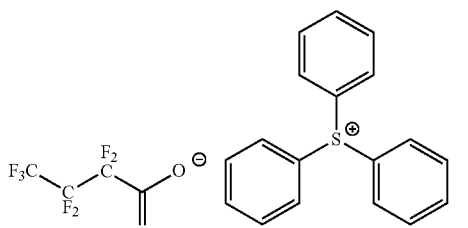

(d2-11)

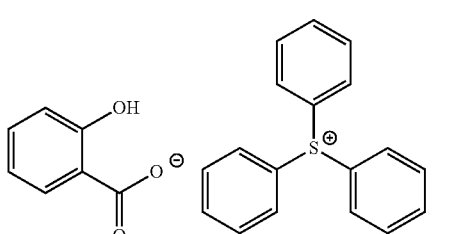

(B)-1: acid generator consisting of a compound represented by the following Chemical formula (B)-1

(E)-1: salicylic acid (F)-1: fluorine-containing polymer compound represented by the following Chemical formula (F)-1; the mass average molecular weight (Mw) in terms of standard polystyrene, which is obtained by GPC measurement, is 26100, the molecular weight dispersivity (Mw/Mn) is 1.50; the copolymer composition ratio (the ratio (molar ratio) of each structural unit in the structural formula) obtained by using $^{13}$C-NMR is l/m=80/20.

(S)-1: γ-butyrolactone (S)-2: mixed solvent of PGMEA/PGME/cyclohexanone (mass ratio 45/30/25)

[Chemical formula 66]

(B)-1

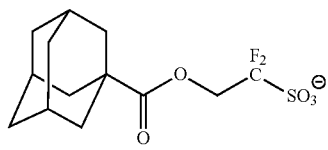

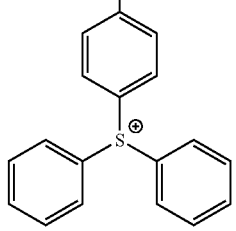

(F)-1

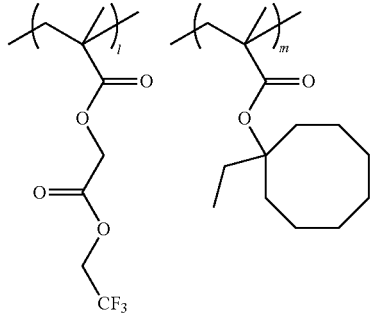

Formation of Resist Pattern

A silicon wafer having a diameter of 12 inches was coated with an organic antireflection film composition "ARC95" (product name, prepared by Brewer Science, Inc.) by using a spinner, was baked at 205° C. for 60 seconds on a hot plate, and was dried so as to form an organic antireflection film having a film thickness of 90 nm.

The organic antireflection film was coated with each of the resist compositions in Examples 1 to 5 and Comparative Examples 1 to 6, was subjected to a pre-baking (PAB) treatment at 110° C. for 60 seconds on the hot plate, and was dried so as to form a resist film having a film thickness of 90 nm.

Then, the resist film was selectively irradiated with ArF excimer laser (193 nm) via a mask for LS using an ArF exposure apparatus for liquid immersion, NSR-S610C [manufactured by Nikon Corporation; Cross-pole (0.78/0.98)w/A-pol. liquid immersion medium: water].

Thereafter, a post exposure bake (PEB) treatment was performed at 95° C. for 60 seconds Then, the resist film was subjected to the alkaline developing at 23° C. for 10 seconds by using 2.38% by mass of tetramethyl ammonium hydroxide (TMAH) aqueous solution "NMD-3" (product name, prepared by Tokyo Ohka Kogyo Co., Ltd.).

As a result, in all examples, a resist pattern with line and space having a line width of 45 nm and a pitch width of 90 nm (hereinafter, referred to as "LS pattern") was formed.

Evaluation of Sensitivity (Eop)

The optimum exposure dose (mJ/cm$^2$) at which the LS pattern having a target size (line width of 45 nm, pitch width of 90 nm) was formed was obtained by the above resist pattern formation. This result is indicated as "Eop (mJ/cm$^2$)" in Tables 2 and 3.

Evaluation of Pattern Shape

Regarding the LS pattern formed by the resist pattern formation, 3σ which is a scale indicating LWR was obtained.

"3σ" indicates three times the value (3σ) (unit: nm) of the standard deviation (σ) obtained from the result of the measurement performed by measuring 400 line positions in the longitudinal direction of the line by using a scanning electron microscope (acceleration voltage of 800V, product name: S-9380, manufactured by Hitachi High-Technologies Corporation).

It means that as the value of 3σ is small, the roughness of the line side wall is small, and thus it is possible to obtain the LS pattern having more uniform width.

Based on the following evaluation criteria with "3σ" as an index, the pattern shape was evaluated. This result is indicated as "LWR (nm)" in Tables 2 and 3.

Evaluation of Defect (Number of Defects)

The respective resist compositions in Examples 1 to 5 and Comparative Examples 1 to 6 were left to stand for three weeks at 25° C. for storage. An LS pattern was formed by using the resist composition after storage in the same way as that used in the "Formation of resist pattern".

Regarding the obtained LS pattern, the total number of defects (total number of defects) in the wafer was measured by using a surface defect observing apparatus (product name: KLA2371, manufactured by KLA-Tencor Corporation). This result is indicated as "Defect (count)" in Tables 2 and 3.

The number of wafers used for such measurement was 2 for each example, and the average value thereof was employed.

TABLE 2

| Resist composition | PAB (° C.) | PEB (° C.) | Eop (mJ/cm$^2$) | LWR (nm) | Defect (count) |
|---|---|---|---|---|---|
| Example 1 | 110 | 95 | 18.0 | 4.05 | 48 |
| Example 2 | 110 | 95 | 19.4 | 3.70 | 167 |
| Example 3 | 110 | 95 | 17.4 | 3.96 | 128 |
| Comparative Example 1 | 110 | 95 | 17.5 | 4.14 | 3717 |
| Example 4 | 110 | 95 | 17.3 | 4.75 | 226 |

From the result indicated in Table 2, it is possible to confirm that the resist composition of Examples 1 to 4 to which the present invention is applied has a clearly smaller value of the defect than the resist composition of Comparative Example 1 which is outside the scope of the present invention, and the exposure stability is improved.

TABLE 3

| Resist composition | PAB (° C.) | PEB (° C.) | Eop (mJ/cm$^2$) | LWR (nm) | Defect (count) |
|---|---|---|---|---|---|
| Example 5 | 110 | 95 | 19.4 | 3.70 | 162 |
| Comparative Example 2 | 110 | 95 | 20.4 | 4.80 | 183 |
| Comparative Example 3 | 110 | 95 | 21.6 | 5.08 | 245 |

TABLE 3-continued

| Resist composition | PAB (° C.) | PEB (° C.) | Eop (mJ/cm$^2$) | LWR (nm) | Defect (count) |
|---|---|---|---|---|---|
| Comparative Example 4 | 110 | 95 | 20.0 | 3.90 | 4127 |
| Comparative Example 5 | 110 | 95 | 20.2 | 4.91 | 177 |
| Comparative Example 6 | 110 | 95 | 22.1 | 4.98 | 129 |

From the result indicated in Table 3, it is possible to confirm that the resist composition of Example 5 to which the present invention is applied has a clearly smaller value of "LWR (nm)" than the resist composition of Comparative Examples 2 and 3 which is outside the scope of the present invention, and the lithography properties are improved.

From the comparison of Example 5 with Comparative Examples 2 and 3, and the comparison of Comparative Example 4 with Comparative Examples 5 and 6, it is possible to confirm that the lithography properties are further improved by the combining the structural unit (a0) with the compound (D1).

What is claimed is:

1. A resist composition which generates an acid upon exposure and whose solubility in a developing solution changes under the action of the acid, the resist composition comprising:

a base material component (A) whose solubility in the developing solution changes under the action of the acid and which contains a polymer compound (A1) consisting of a structural unit (a0) represented by the following general formula (a0-1) and a structural unit (a1) containing an acid-decomposable group which increases the polarity under action of the acid;

an acid generator component (B) which generates acid upon exposure;

an organic solvent component (S); and an acid diffusion control agent component (D) which contains a compound (D1) whose a conjugate acid has an acid dissociation constant (pKa) of less than 3, provided that the compound (D1) is excluded from the acid generator component (B):

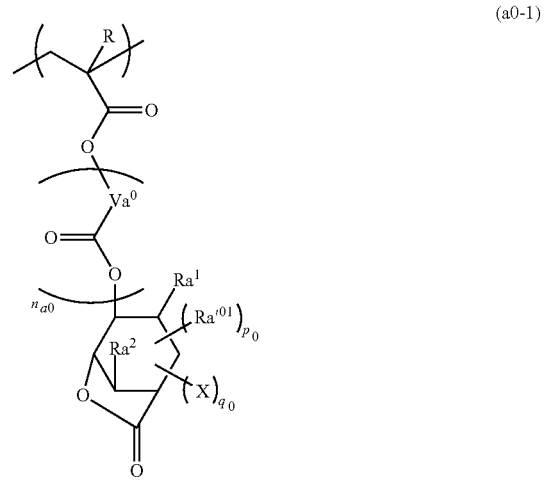

(a0-1)

wherein R is a hydrogen atom, an alkyl group having 1 to 5 carbon atoms, or a halogenated alkyl group having 1 to 5 carbon atoms;

$Va^0$ is a divalent hydrocarbon group which may have a substituent;

$n_{a0}$ is an integer of 0 to 2;

$Ra^1$ and $Ra^2$ each independently represent a hydrogen atom, an alkyl group having 1 to 5 carbon atoms, an alkoxy group, or an alkylthio group, or $Ra^1$ and $Ra^2$ may be bonded to each other so as to form an alkylene group having 1 to 6 carbon atoms, which may contain an oxygen atom or a sulfur atom, an ether bond, or a thioether bond;

$Ra^{\prime 01}$ is a halogen atom, an alkyl group having 1 to 6 carbon atoms which may have a halogen atom, a hydroxyalkyl group having 1 to 6 carbon atoms, of which the hydroxy group may be protected by a protective group and which may have a halogen atom, a carboxy group which may form a salt, or a substituted oxycarbonyl group;

$p_0$ is an integer of 0 to 8, and in a case where two or more $Ra^{\prime 01}$'s are present, the plural $Ra^{\prime 01}$'s may be the same as or different from each other;

X is a cyano group; and $q_0$ is an integer of 1 to 9, and in a case where two or more X's are present, the plural X's may be the same as or different from each other.

2. The resist composition according to claim 1, wherein the compound (D1) is a compound represented by the following general formula (d1):

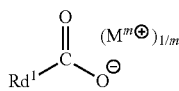
(d1)

wherein $Rd^1$ is a cyclic group which may have a substituent, a chain-like alkyl group which may have a substituent, or a chain-like alkenyl group which may have a substituent, m is an integer of 1 or more, and $M^{m+}$ represents an m-valent organic cation.

3. The resist composition according to claim 1, wherein the content of the compound (D1) is 0.5 to 10 parts by mass with respect to 100 parts by mass of the base material component (A).

4. The resist composition according to claim 2, wherein $Rd^1$ is an aromatic ring including a hydroxybenzoic acid skeleton and at least one hydrogen atom of the aromatic ring is substituted with a group having a halogen atom, or a linear alkyl group and at least one hydrogen atom of the alkyl group is substituted with a group having a halogen atom.

5. The resist composition according to claim 2, wherein $Rd^1$ is an aromatic ring including a hydroxybenzoic acid skeleton and at least one hydrogen atom of the aromatic ring is substituted with a group having a halogen atom.

6. A method for forming a resist pattern, comprising:
applying the resist composition according to claim 1 on a support to form a resist film;
exposing the resist film; and
developing the exposed resist film to form a resist pattern.

7. A resist composition which generates an acid upon exposure and whose solubility in a developing solution changes under the action of the acid,
the resist composition comprising:
a base material component (A) whose solubility in the developing solution changes under the action of the acid and which contains a polymer compound (A1) consisting of a structural unit (a0) represented by the following general formula (a0-1), a structural unit (a1) containing an acid-decomposable group, which increases the polarity under the action of the acid, and a structural unit (a2) containing a lactone-containing cyclic group, a —$SO_2$— containing cyclic group or a carbonate-containing cyclic group;
an acid generator component (B) which generates an acid upon exposure;
an organic solvent component (S); and
an acid diffusion control agent component (D) which contains a compound (D1) whose a conjugate acid has an acid dissociation constant (pKa) of less than 3, provided that the compound (D1) is excluded from the acid generator component (B):

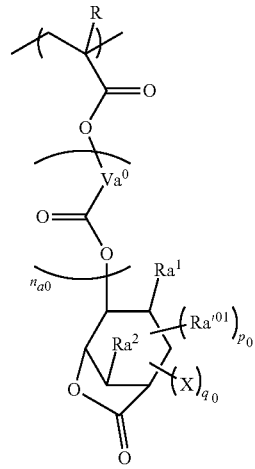
(a0-1)

wherein R is a hydrogen atom, an alkyl group having 1 to 5 carbon atoms, or a halogenated alkyl group having 1 to 5 carbon atoms;

$Va^0$ is a divalent hydrocarbon group which may have a substituent;

$n_{a0}$ is an integer of 0 to 2;

$Ra^1$ and $Ra^2$ each independently represent a hydrogen atom, an alkyl group having 1 to 5 carbon atoms, an alkoxy group, or an alkylthio group, or $Ra^1$ and $Ra^2$ may be bonded to each other so as to form an alkylene group having 1 to 6 carbon atoms, which may contain an oxygen atom or a sulfur atom, an ether bond, or a thioether bond;

$Ra^{\prime 01}$ is a halogen atom, an alkyl group having 1 to 6 carbon atoms which may have a halogen atom, a hydroxyalkyl group having 1 to 6 carbon atoms, of which the hydroxy group may be protected by a protective group and which may have a halogen atom, a carboxy group which may form a salt, or a substituted oxycarbonyl group;

$p_0$ is an integer of 0 to 8, and in a case where two or more $Ra^{\prime 01}$'s are present, the plural $Ra^{\prime 01}$'s may be the same as or different from each other;

X is a cyano group; and $q_0$ is an integer of 1 to 9, and in a case where two or more X's are present, the plural X's may be the same as or different from each other.

8. The resist composition according to claim 7, wherein the compound (D1) is a compound represented by the following general formula (d1):

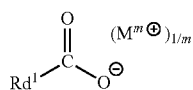
(d1)

wherein $Rd^1$ is a cyclic group which may have a substituent, a chain-like alkyl group which may have a substituent, or a chain-like alkenyl group which may have a substituent, m is an integer of 1 or more, and $M^{m+}$ represents an m-valent organic cation.

9. The resist composition according to claim 7, wherein the content of the compound (D1) is 0.5 to 10 parts by mass with respect to 100 parts by mass of the base material component (A).

10. The resist composition according to claim 8, wherein $Rd^1$ is an aromatic ring including a hydroxybenzoic acid skeleton and at least one hydrogen atom of the aromatic ring is substituted with a group having a halogen atom, or a linear alkyl group and at least one hydrogen atom of the alkyl group is substituted with a group having a halogen atom.

11. The resist composition according to claim 8, wherein $Rd^1$ is an aromatic ring including a hydroxybenzoic acid skeleton and at least one hydrogen atom of the aromatic ring is substituted with a group having a halogen atom.

12. A method for forming a resist pattern, comprising:
applying the resist composition according to claim 7 on a support to form a resist film;
exposing the resist film; and
developing the exposed resist film to form a resist pattern.

13. A resist composition which generates an acid upon exposure and whose solubility in a developing solution changes under the action of the acid, the resist composition comprising:
a base material component (A) whose solubility in the developing solution changes under the action of the acid and which contains a polymer compound (A1) consisting of a structural unit (a0) represented by the following general formula (a0-1), a structural unit (a1) containing an acid-decomposable group, which increases the polarity under the action of the acid, a structural unit (a2) containing a lactone-containing cyclic group, a —SO$_2$— containing cyclic group or a carbonate-containing cyclic group, and a structural unit (a3) containing a polar group-containing aliphatic hydrocarbon group;
an acid generator component (B) which generates an acid upon exposure;
an organic solvent component (S); and
an acid diffusion control agent component (D) which contains a compound (D1) whose a conjugate acid has an acid dissociation constant (pKa) of less than 3, provided that the compound (D1) is excluded from the acid generator component (B):

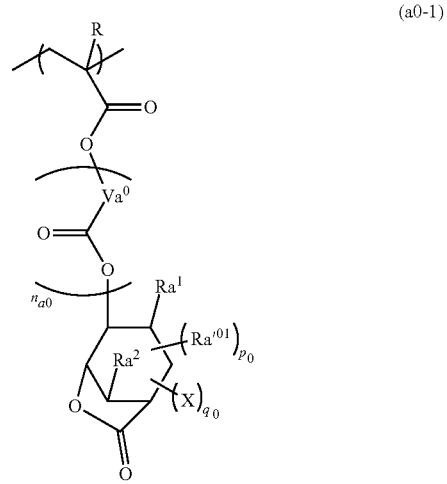
(a0-1)

wherein R is a hydrogen atom, an alkyl group having 1 to 5 carbon atoms, or a halogenated alkyl group having 1 to 5 carbon atoms;
$Va^0$ is a divalent hydrocarbon group which may have a substituent;
$n_{a0}$ is an integer of 0 to 2;
$Ra^1$ and $Ra^2$ each independently represent a hydrogen atom, an alkyl group having 1 to 5 carbon atoms, an alkoxy group, or an alkylthio group, or $Ra^1$ and $Ra^2$ may be bonded to each other so as to form an alkylene group having 1 to 6 carbon atoms, which may contain an oxygen atom or a sulfur atom, an ether bond, or a thioether bond;
$Ra^{'01}$ is a halogen atom, an alkyl group having 1 to 6 carbon atoms which may have a halogen atom, a hydroxyalkyl group having 1 to 6 carbon atoms, of which the hydroxy group may be protected by a protective group and which may have a halogen atom, a carboxy group which may form a salt, or a substituted oxycarbonyl group;
$p_0$ is an integer of 0 to 8, and in a case where two or more $Ra^{'01}$'s are present, the plural $Ra^{'01}$'s may be the same as or different from each other;
X is a cyano group; and
$q_0$ is an integer of 1 to 9, and in a case where two or more X's are present, the plural X's may be the same as or different from each other.

14. The resist composition according to claim 13, wherein the compound (D1) is a compound represented by the following general formula (d1):

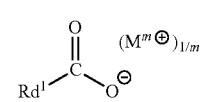
(d1)

wherein $Rd^1$ is a cyclic group which may have a substituent, a chain-like alkyl group which may have a substituent, or a chain-like alkenyl group which may have a substituent, m is an integer of 1 or more, and $M^{m+}$ represents an m-valent organic cation.

15. The resist composition according to claim 13, wherein the content of the compound (D1) is 0.5 to 10 parts by mass with respect to 100 parts by mass of the base material component (A).

16. The resist composition according to claim 14, wherein $Rd^1$ is an aromatic ring including a hydroxybenzoic acid skeleton and at least one hydrogen atom of the aromatic ring is substituted with a group having a halogen atom, or a linear alkyl group and at least one hydrogen atom of the alkyl group is substituted with a group having a halogen atom.

17. The resist composition according to claim 14, wherein $Rd^1$ is an aromatic ring including a hydroxybenzoic acid skeleton and at least one hydrogen atom of the aromatic ring is substituted with a group having a halogen atom.

18. A method for forming a resist pattern, comprising:
applying the resist composition according to claim 13 on a support to form a resist film;
exposing the resist film; and
developing the exposed resist film to form a resist pattern.

* * * * *